United States Patent
Hakonarson et al.

(10) Patent No.: US 9,783,851 B2
(45) Date of Patent: Oct. 10, 2017

(54) GENETIC ALTERATIONS ASSOCIATED WITH AUTISM AND THE AUTISTIC PHENOTYPE AND METHODS OF USE THEREOF FOR THE DIAGNOSIS AND TREATMENT OF AUTISM

(75) Inventors: Hakon Hakonarson, Malvern, PA (US); Joseph Glessner, Turnersville, NJ (US); Jonathan Bradfield, Philadelphia, PA (US); Struan Grant, Philadelphia, PA (US); Haitao Zhang, Philadelphia, PA (US); Kai Wang, Lansdale, PA (US)

(73) Assignee: The Children's Hospital of Philadelphia, Philadelphia, PA (US)

( * ) Notice: Subject to any disclaimer, the term of this patent is extended or adjusted under 35 U.S.C. 154(b) by 348 days.

(21) Appl. No.: 12/918,508

(22) PCT Filed: Feb. 20, 2009

(86) PCT No.: PCT/US2009/034784
§ 371 (c)(1),
(2), (4) Date: May 6, 2011

(87) PCT Pub. No.: WO2009/105718
PCT Pub. Date: Aug. 27, 2009

(65) Prior Publication Data
US 2011/0207124 A1 Aug. 25, 2011

Related U.S. Application Data

(60) Provisional application No. 61/030,136, filed on Feb. 20, 2008, provisional application No. 61/107,163, filed on Oct. 21, 2008.

(51) Int. Cl.
*C07H 21/02* (2006.01)
*C07H 21/04* (2006.01)
*C12Q 1/68* (2006.01)

(52) U.S. Cl.
CPC ..... *C12Q 1/6883* (2013.01); *C12Q 2600/136* (2013.01); *C12Q 2600/156* (2013.01); *C12Q 2600/158* (2013.01); *C12Q 2600/16* (2013.01)

(58) Field of Classification Search
CPC ............ C12Q 1/6883; C12Q 2600/156; C12Q 2600/16
See application file for complete search history.

(56) References Cited

U.S. PATENT DOCUMENTS

2003/0170690 A1 9/2003 Shatz et al.
2006/0194201 A1 8/2006 Fryns et al.

OTHER PUBLICATIONS

Database of Genomic Variants, Variation_8713, from http://projects.tcag.ca, Aug. 2, 2012, p. 1.*
Database of Genomic Variants, Variation_9092, from http://projects.tcag.ca, Aug. 2, 2012, p. 1.*
Pinto D. et al. Human Molecular Genetics, 2007, vol. 16, Review Issue 2 R168-R173.*
dbSNP Submitted SNP (ss) Details: ss5709216, from www.ncbi.nlm.nih.gov, p. 1.*
Steinberg J.J. Nucleic Acids and Their Derivatives. Chapter 25—Handbook of Thin-Layer Chromatography. Edited by Joseph Sherma and Bernard Fried. CRC Press 2003, 15 printed pages.*
Reference SNP(refSNP) Cluster Report: rs4327572, from http://www.ncbi.nlm.nih.gov, Oct. 30, 2012, pp. 1-4.*
Reference SNP(refSNP) Cluster Report: rs149151326, from http://www.ncbi.nlm.nih.gov, Oct. 30, 2012, pp. 1-2.*
Submitted SNP(ss) Details: ss84254499 (Dec. 4, 2007), from www.ncbi.nlm.nih.gov, 1 printed page.*
Craddock N. et al. The Wellcome Trust Case Control Consortium "Genome-wide association study of copy number variation in 16,000 cases of eight common diseases and 3,000 shared controls" Nature 464, 713-720 (Apr. 1, 2010).*
Autism Genome Project Consortium. "Mapping autism risk loci using genetic linkage and chromosomal rearrangements." Nature Genetics, Mar. 2007;39(3):319-328.
NCBI SNP database (rs4971724_chr2; rs7497239_chr15; rs9860992_nlgn1), May 25, 2006.
NCBI SNP database (rs10038113_chr5), May 25, 2006.
Sebat, J., et al. "Strong association of de novo copy number mutations with autism." Science. Apr. 20, 2007;316(5823):445-9. Epub Mar. 15, 2007.
Yu, C.E., et al. "Presence of large deletions in kindreds with autism." Am J Hum Genet. Jul. 2002;71(1):100-15. Epub Jun. 7, 2002.
Spence, S.J., et al. "The genetics of autism." Semin Pediatr Neurol. Sep. 2004;11(3):196-204.
Marshall, C.R., et al. "Structural variation of chromosomes in autism spectrum disorder." Am J Hum Genet. Feb. 2008;82(2):477-88. Epub Jan. 17, 2008.
Jacob, S., et al. "Association of the oxytocin receptor gene (OXTR) in Caucasian children and adolescents with autism." Neurosci Lett. Apr. 24, 2007;417(1):6-9. Epub Feb. 3, 2007.

* cited by examiner

*Primary Examiner* — Stephen Kapushoc
(74) *Attorney, Agent, or Firm* — Kathleen D. Rigaut; Dann, Dorfman, Herrell & Skillman

(57) ABSTRACT

Compositions and methods for the detection and treatment of autism and autistic spectrum disorder are provided.

3 Claims, 13 Drawing Sheets

Panel (a):

CNV Range: chr5:24597380-24629650.

The CNV has been previously described in HapMap subjects (Redon et al). We attempted experimental validation using the MLPA assay (a representative series is shown below, with error bars indicating standard error).

Panel (b):

Range: chr5:25426837-25464318. We validated the CNV by both QPCR and MLPA.

QPCR results: The CNV is detected in only one family (Red circle: subject carrying the deletions; Star: DNA not available).

MLPA results (two probes were used and both validate the CNV, a representative series is shown)

Panel (c):

Region: chr5:26041000-26069708

This CNV is validate by MLPA (two probes were used and both validate the CNV, a representative series is shown).

Figure 4 (continued)

Panel (d):

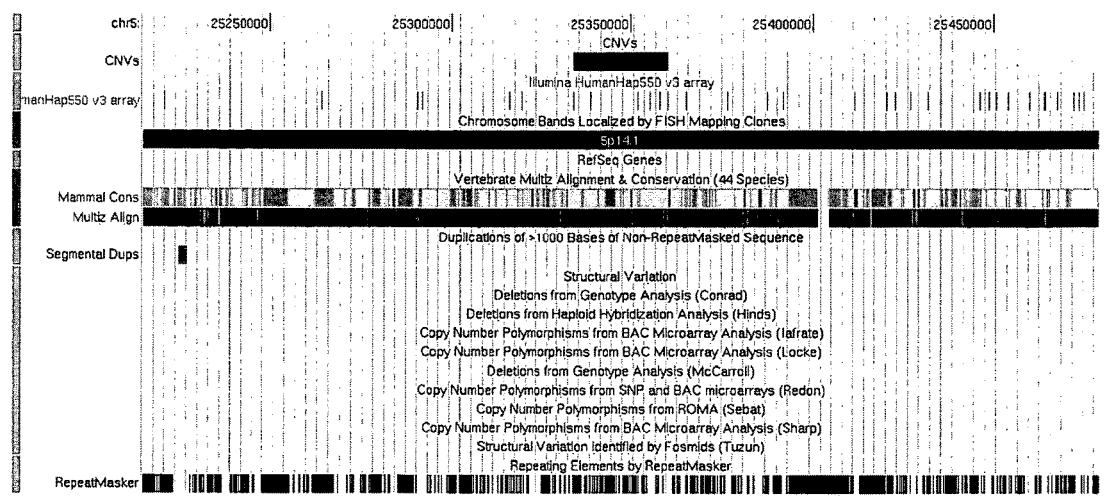

Region: chr5:25333737-25360219

This CNV is detected in two related subjects (AU0915301, AU0915202). We attempted experimental validation by TaqMan QPCR on 31 subjects, but all CN estimates have very large variations from 1.8 to over 30 (the CN for four subjects in this family were between 2.3 to 2.7), indicating a potential assay error. Nevertheless, since it is detected in two related subjects, we list the CNV information here, but caution that it failed validation.

Panel (e):

Region: chr5:26955104-26963260

The CNV has been previously described in HapMap subjects (Redon et al).

GENETIC ALTERATIONS ASSOCIATED WITH AUTISM AND THE AUTISTIC PHENOTYPE AND METHODS OF USE THEREOF FOR THE DIAGNOSIS AND TREATMENT OF AUTISM

CROSS REFERENCE TO RELATED APPLICATIONS

This application is a §371 national phase entry of PCT/US2009/034784 filed Feb. 20, 2009, which claims priority to U.S. Provisional Application Nos. 61/030,136 and 61/107,163 filed Feb. 20, 2008 and Oct. 21, 2008, respectively, each of which is incorporated by reference herein.

FIELD OF THE INVENTION

This invention relates to the fields of genetics and the diagnosis and treatment of autism and autism spectrum disorders.

BACKGROUND OF THE INVENTION

Several publications and patent documents are cited throughout the specification in order to describe the state of the art to which this invention pertains. Each of these citations is incorporated herein by reference as though set forth in full.

Autism (MIM [209850]) is a severe and relatively common neuropsychiatric disorder characterized by abnormalities in social behavior and communication skills, with tendencies towards patterns of abnormal repetitive movements and other behavior disturbances. Current prevalence estimates are 0.1-0.2% of the population for autism and 0.6% of the population for ASDs[1]. Globally, males are affected four times as often as females[2]. As such, autism poses a major public health concern of unknown cause that extends into adulthood and places an immense economic burden on society. The most prominent features of autism are social and communication deficits. The former are manifested in reduced sociability (reduced tendency to seek or pay attention to social interactions), a lack of awareness of social rules, difficulties in social imitation and symbolic play, impairments in giving and seeking comfort and forming social relationships with other individuals, failure to use nonverbal communication such as eye contact, deficits in perception of others' mental and emotional states, lack of reciprocity, and failure to share experience with others. Communication deficits are manifested as a delay in or lack of language, impaired ability to initiate or sustain a conversation with others, and stereotyped or repetitive use of language. Autistic children have been shown to engage in free play much less frequently and at a much lower developmental level than peers of similar intellectual abilities. Markers of social deficits in affected children appear as early as 12-18 months of age, suggesting that autism is a neurodevelopmental disorder. It has been suggested that autism originates in developmental failure of neural systems governing social and emotional functioning. Although social and cognitive development are highly correlated in the general population, the degree of social impairment does not correlate well with IQ in individuals with autism. The opposite is seen in Down's syndrome and Williams syndrome, where social development is superior to cognitive function. Both examples point to a complex source of sociability.

The etiology of the most common forms of autism is still unknown. In the first description of the disease, Kanner suggested an influence of child-rearing practices on the development of autism, after observing similar traits in parents of the affected children. While experimental data fail to support several environmental hypotheses, there has been growing evidence for a strong genetic influence on this disorder. The rate of autism in siblings of affected individuals was shown to be a 2-6%, two orders of magnitude higher than in the general population. Twin studies have demonstrated significant differences in monozygotic and dizygotic twin concordance rates, the former concordant in 60% of twin pairs, with most of the non-autistic monozygotic co-twins displaying milder related social and communicative abnormalities. Social, language and cognitive difficulties have also been found among relatives of autistic individuals in comparison to the relatives of controls. The heritability of autism has been estimated to be >90%.

The genetic basis of autism has been extensively studied in the past decade using three complementary approaches: cytogenetic studies; linkage analysis, and candidate gene analysis see for a review Vorstman et al., (2006) Mol. Psychiatry 11:18-28; Veenstra-VanderWeele and Cook, (2004) Mol. Psychiatry 9: 819-32). Searches for chromosomal abnormalities in autism have revealed terminal and interstitial deletions, balanced and unbalanced translocations, and inversions on a large number of chromosomes, with abnormalities on chromosomes 15, 7, and X being most frequently reported. The importance of the regions indicated by cytogenetic studies was evaluated by several whole genome screens in the multiplex autistic families (International Molecular Genetic Study of Autism Consortium, 1998). Strong and concordant evidence for the presence of an autism susceptibility locus was obtained for chromosome 7q; moderate evidence was obtained for loci on chromosomes 15q, 16p, 19p, and 2q; and the majority of the studies find no support for linkage to the X chromosome (Lamb et al, (2005) Med Genet. 42: 132-137; Lord et al, (2000) Autism Dev Disord. 30:205-223. The AGRE sample provided the strongest evidence for loci on 17q and 5p (Yonan et al., (2003) Am J Hum Genet. 73:886-97). Numerous candidate gene studies in autism have focused on a few major candidates with respect to their location or function (reviewed in Veenstra-VanderWeele et al 2004, supra). Jamain et al (2003) Nat Genet. 34:27-9, reported rare nonsynonymous mutations in the X-linked genes encoding neuroligins, specifically NLGN3 and NLGN4, in linkage regions associated with ASD. Other evidence for a genetic basis of autistic endophenotypes comes from the study of disorders that share phenotypic features that overlap with autism such as Fragile X and Rett syndrome.

Many emerging theories of autism focus on changes in neuronal connectivity as the potential underlying cause of these disorders. Imaging studies reveal changes in local and global connectivity and developmental studies of activity-dependent cortical development suggest that autism might result from an imbalance of inhibitory and excitatory synaptic connections during development. The fundamental unit of neuronal connectivity is the synapse; thus, if autism is a disorder of neuronal connectivity, then it can likely be understood in neuronal terms as a disorder of synaptic connections. Indeed, genetic studies reveal that mutations in key proteins involved in synaptic development and plasticity, such as neuroligins, FMRP and MeCP2 are found in individuals with autism and in two forms of mental retardation with autistic features, specifically Fragile-X and Rett's syndrome (Jamain et al, 2003, supra). Thus the pursuit of linkage between genetic anomalies and (endo)phenotypes at the neuronal level appears both warranted and fruitful. Furthermore, such neuronal connectivity anomalies, revealed, for example, by direct white matter tractography, or by observable delays in characteristic electrical activity, can be directly linked to behavioral and clinical manifestations of ASD, allowing these neuron-level phenotypes to be interpreted as neural correlates of behavior.

Overall, the linkage analysis studies conducted to date and discussed above have achieved only limited success in identifying genetic determinants of autism due to numerous reasons, among others the generic problem that the linkage analysis approach is generally poor in identifying common genetic variants that have modest effects. This problem is highlighted in autism, a spectrum disorder wherein the varied phenotypes are determined by the net result of interactions between multiple genetic and environmental factors and, in which, any particular genetic variant that is identified is likely to contribute little to the overall risk for disease.

In a recent study, Sebat and colleagues reported association of de novo copy number variations (CNVs) with autism[8], suggesting that CNVs may underlie the disease. Indeed, their results suggest that CNVs at four loci account for a small % of ASD[8].

However, these association results remain to be replicated in independent studies, and collectively only explain a small proportion of the genetic risk for autism, thus suggesting the existence of additional genetic loci but with unknown frequency and effect size. In an effort to systematically search for the remaining loci, we performed a GWA study in 1200 Caucasian children with autism and over 2000 disease-free controls of European decent.

SUMMARY OF THE INVENTION

In accordance with the present invention, compositions and methods are provided for diagnosis and treatment of autism and autistic spectrum disorder. An exemplary method entails detecting the presence of at least one deletion containing CNV in a target polynucleotide wherein if said CNV is present, said patient has an increased risk for developing autism and/or autistic spectrum disorder, wherein said deletion containing CNV is selected from the group of CNVs consisting of chr8:43765570-43776595, chr2:51120644-51147600, chr3:1915190-1915922, chr3:4199731-4236304, chr10:87941666-87949029, chr6:162584576-162587001, chr2:78268199-78311249 and chr16:45834321-45887745. The method may optionally include detection of at least one single nucleotide polymorphism selected from the group consisting of rs8185771 on chromosome 8, rs4971724 on chromosome 2, rs10510221 on chromosome 3, rs1444056 on chromosome 3, rs12411971 on chromosome 10, rs12214788 on chromosome 6, rs2164850 on chromosome 2, and rs174642 on chromosome 16.

In yet another embodiment of the invention, a method for detecting a propensity for developing autism or autistic spectrum disorder entails detecting the presence of at least one duplication containing CNV in a target polynucleotide wherein if said CNV is present, said patient has an increased risk for developing autism and/or autistic spectrum disorder, wherein said duplication containing CNV is selected from the group of CNVs consisting of chr2:13119667-13165898, chr15:22393833-22532309, chr12:31300846-31302088, chr6:69291821-69294028, chr3:2548148-2548531, chr3:174754378-174771975, chr4:144847402-144854579, chr1:145658465-145807358, chr2:237486328-237497105; chr6:168091860-168339100, chr19:22431189-22431397, chr15:22393833-22532309, chr22:19351264-19358946, chr7:32667087-32770713, chr20:55426961-55430874, chr1:174500555-174543675, chr8:55021047-55070134, and chr3:122826190-122870474. The method may optionally entail detection of at least one single nucleotide polymorphism selected from the group consisting of rs4346352 on chromosome 2, rs7497239 on chromosome 15, rs617372 on chromosome 12, rs9342717 on chromosome 6, rs17015816 on chromosome 3, rs9860992 on chromosome 3, rs7681914 on chromosome 4, rs12408178 on chromosome 1, rs1107194 on chromosome 2, rs9346649 on chromosome 6, rs1230300 on chromosome 19, rs7497239 on chromosome 15, rs674478 on chromosome 22, rs13225132 on chromosome 7, rs6025553 on chromosome 20, rs10798450 on chromosome 1, rs10435634 on chromosome 8 and rs2070180 on chromosome 3.

In another aspect of the invention, a method for detecting a propensity for developing autism or autistic spectrum disorder in a patient in need thereof is provided. An exemplary method entails detecting the presence of at least one SNP containing nucleic acid in a target polynucleotide wherein if said SNP is present, said patient has an increased risk for developing autism and/or autistic spectrum disorder, wherein said SNP containing nucleic acid is selected from the group of SNPs consisting of rs4307059, rs7704909, rs12518194, rs4327572, rs1896731, and rs10038113 on chromosome 5.

In another embodiment of the invention a method for identifying agents which alter neuronal signaling and/or morphology is provided. Such a method comprises providing cells expressing at least one of the CNVs or SNPs listed above (step a); providing cells which express the cognate wild type sequences corresponding to the CNV or SNP containing nucleic acids (step b); contacting the cells from each sample with a test agent and analyzing whether said agent alters neuronal signaling and/or morphology of cells of step a) relative to those of step b), thereby identifying agents which alter neuronal signaling and morphology. In a preferred embodiment the test agent modulates cadherin-mediated cellular adhesion. Methods of treating autistic patients via administration of test agents identified using the methods described herein in patients in need thereof are also encompassed by the present invention.

The invention also provides at least one isolated autism related SNP-containing nucleic acid selected from the group consisting of rs4307059, rs7704909, rs12518194, rs4327572, rs1896731 and rs10038113. Such SNP containing nucleic acids may optionally be contained in a suitable expression vector for expression in neuronal cells.

In another aspect of the invention, nucleic acids comprising the CNVs and SNPs set forth above are provided. In a preferred embodiment, the nucleic acids are affixed to a solid support.

Also provided are transgenic mice comprising the CNV and/or SNP containing nucleic acid molecules described herein. Such mice provide a superior in vivo screening tool to identify agents which modulate the progression and development of autism.

DETAILED DESCRIPTION OF THE INVENTION

Figure 1:
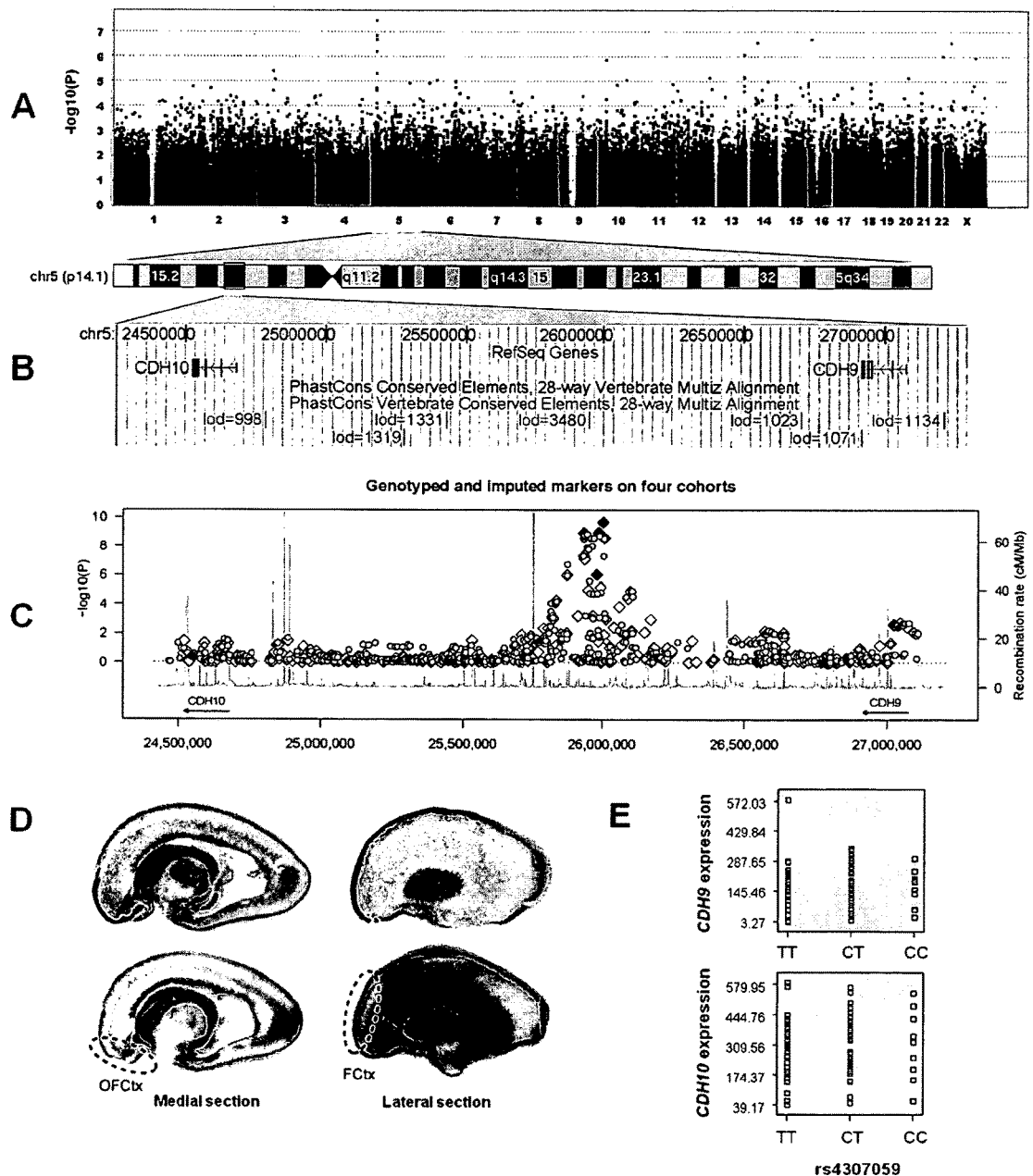
FIG. 1. (A) A Manhattan plot showing the $-\log_{10}(P)$ values of SNPs from the genome-wide association meta-analysis of the AGRE and ACC cohorts. (B) The genomic region containing the most significant SNPs is displayed in UCSC Genome Browser, and the conserved genomic elements are displayed in the PhastCons track with LOD scores. (C) Both genotyped (diamonds) and imputed SNPs (grey circles) are plotted with their P-values (as −log 10 values) as a function of genomic position (NCBI Build 36). Genotyped SNPs were colored based on their correlation with rs4307059 (red: $r^2>0.8$; orange: $0.5<r^2<0.8$; yellow: $0.2<r^2<0.5$; white: $r^2<0.2$). Estimated recombination rates from HapMap data are plotted to reflect the local LD structure. (D) The in situ hybridization of CDH10 in human fetal brain, above corresponding cresyl violet stained marker slides. Orbitofronto Cortex (OFCtx) and Frontal Cortex (FCtx) are highlighted, with dramatic expression enrichment in anterior cortex. (E) The SNP genotypes of rs4307059 are not associated with CDH9 or CDH10 transcript levels in 93 cortical brain tissues.

Epidemiologic studies have convincingly implicated genetic factors in the pathogenesis of autism, a common neuropsychiatric disorder in children, which presents with variable phenotype expression that extends into adulthood. Several genetic determinants have already been reported, including de novo copy number variations (CNVs) that may account for a small subset of autism spectrum disorder (ASD). Implicated genomic regions appear to be highly heterogeneous with variations reported in several genes, including NRXN1, NLGN3, SHANK3 and AUTS2. In order to identify novel genetic factors that contribute to the pathogenesis of autism, we performed a genome-wide association (GWA) study in a cohort of 1200 autism cases (ADI-R and/or ADOS positive) from a mixture of simplex and multiplex families and 2000 disease-free control children of European decent. Following our association analysis, it became clear that there were no genome wide significant signals ($P>X\times10-7$). However, we identified several novel CNVs that associate with autism, totaling 12 deleted and 9 duplicated loci that met a pre-specified significance threshold ($P<1\times10^{-5}$). A subset of these CNVs replicated in an independent autism cohort from the Autism Genetic Research Exchange (AGRE) consortium, including TRPS1 and HCN1, and could be tagged using a single SNP. Taken together, these results suggest that the genetic landscape in autism involves both common and rare CNVs which associate with the autistic phenotypes. These CNVs are highly heterogeneous, in most instances unique to individual families and cluster around genes that are enriched in the class of neuronal signaling and development.

Additional genetic risk factors underlying autism spectrum disorders (ASDs), were also identified in these genome-wide association studies. Six SNPs that reside between two genes encoding membrane cell-adhesion molecules, namely cadherin 10 (CDH10) and cadherin 9 (CDH9), revealed strong association signals, with the most significant SNP being rs4307059 ($P=3.4\times10^{-8}$; OR=1.19). These association signals were replicated in two independent cohorts, including 487 autism families (1,537 subjects) and a cohort of 108 ASD cases and 540 controls, with combined P-values ranging from $7.9\times10^{-8}$ to $2.1\times10^{-10}$ for the entire data set of over 10,000 subjects. Our results implicate neuronal cell-adhesion molecules in the pathogenesis of ASDs, and represent the first demonstration of genome-wide significant association of common variants with susceptibility to ASDs.

Definitions

A "copy number variation (CNV)" refers to the number of copies of a particular gene in the genotype of an individual. CNVs represent a major genetic component of human phenotypic diversity. Susceptibility to genetic disorders is known to be associated not only with single nucleotide polymorphisms (SNP), but also with structural and other genetic variations, including CNVs. A CNV represents a copy number change involving a DNA fragment that is ~1 kilobases (kb) or larger (Feuk et al. 2006a). CNVs described herein do not include those variants that arise from the insertion/deletion of transposable elements (e.g., ~6-kb KpnI repeats) to minimize the complexity of future CNV analyses. The term CNV therefore encompasses previously introduced terms such as large-scale copy number variants (LCVs; Iafrate et al. 2004), copy number polymorphisms (CNPs; Sebat et al. 2004), and intermediate-sized variants (ISVs; Tuzun et al. 2005), but not retroposon insertions.

A "single nucleotide polymorphism (SNP)" refers to a change in which a single base in the DNA differs from the usual base at that position. These single base changes are called SNPs or "snips." Millions of SNP's have been cataloged in the human genome. Some SNPs such as that which causes sickle cell are responsible for disease. Other SNPs are normal variations in the genome.

The term "genetic alteration" as used herein refers to a change from the wild-type or reference sequence of one or more nucleic acid molecules. Genetic alterations include without limitation, base pair substitutions, additions and deletions of at least one nucleotide from a nucleic acid molecule of known sequence.

The term "solid matrix" as used herein refers to any format, such as beads, microparticles, a microarray, the surface of a microtitration well or a test tube, a dipstick or a filter. The material of the matrix may be polystyrene, cellulose, latex, nitrocellulose, nylon, polyacrylamide, dextran or agarose.

The phrase "consisting essentially of" when referring to a particular nucleotide or amino acid means a sequence having the properties of a given SEQ ID NO. For example, when used in reference to an amino acid sequence, the phrase includes the sequence per se and molecular modifications that would not affect the functional and novel characteristics of the sequence.

"Target nucleic acid" as used herein refers to a previously defined region of a nucleic acid present in a complex nucleic acid mixture wherein the defined wild-type region contains at least one known nucleotide variation which may or may not be associated with autism. The nucleic acid molecule may be isolated from a natural source by cDNA cloning or subtractive hybridization or synthesized manually. The nucleic acid molecule may be synthesized manually by the triester synthetic method or by using an automated DNA synthesizer.

With regard to nucleic acids used in the invention, the term "isolated nucleic acid" is sometimes employed. This term, when applied to DNA, refers to a DNA molecule that is separated from sequences with which it is immediately contiguous (in the 5' and 3' directions) in the naturally occurring genome of the organism from which it was derived. For example, the "isolated nucleic acid" may comprise a DNA molecule inserted into a vector, such as a plasmid or virus vector, or integrated into the genomic DNA of a prokaryote or eukaryote. An "isolated nucleic acid molecule" may also comprise a cDNA molecule. An isolated nucleic acid molecule inserted into a vector is also sometimes referred to herein as a recombinant nucleic acid molecule.

With respect to RNA molecules, the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form.

By the use of the term "enriched" in reference to nucleic acid it is meant that the specific DNA or RNA sequence constitutes a significantly higher fraction (2-5 fold) of the total DNA or RNA present in the cells or solution of interest than in normal cells or in the cells from which the sequence was taken. This could be caused by a person by preferential reduction in the amount of other DNA or RNA present, or by a preferential increase in the amount of the specific DNA or RNA sequence, or by a combination of the two. However, it should be noted that "enriched" does not imply that there are no other DNA or RNA sequences present, just that the relative amount of the sequence of interest has been significantly increased.

It is also advantageous for some purposes that a nucleotide sequence be in purified form. The term "purified" in reference to nucleic acid does not require absolute purity (such as a homogeneous preparation); instead, it represents an indication that the sequence is relatively purer than in the natural environment (compared to the natural level, this level should be at least 2-5 fold greater, e.g., in terms of mg/ml). Individual clones isolated from a cDNA library may be purified to electrophoretic homogeneity. The claimed DNA molecules obtained from these clones can be obtained directly from total DNA or from total RNA. The cDNA clones are not naturally occurring, but rather are preferably obtained via manipulation of a partially purified naturally occurring substance (messenger RNA). The construction of a cDNA library from mRNA involves the creation of a synthetic substance (cDNA) and pure individual cDNA clones can be isolated from the synthetic library by clonal selection of the cells carrying the cDNA library. Thus, the process which includes the construction of a cDNA library from mRNA and isolation of distinct cDNA clones yields an approximately $10^{-6}$-fold purification of the native message. Thus, purification of at least one order of magnitude, preferably two or three orders, and more preferably four or five orders of magnitude is expressly contemplated.

The term "substantially pure" refers to a preparation comprising at least 50-60% by weight the compound of interest (e.g., nucleic acid, oligonucleotide, etc.). More preferably, the preparation comprises at least 75% by weight, and most preferably 90-99% by weight, the compound of interest. Purity is measured by methods appropriate for the compound of interest.

The term "complementary" describes two nucleotides that can form multiple favorable interactions with one another. For example, adenine is complementary to thymine as they can form two hydrogen bonds. Similarly, guanine and cytosine are complementary since they can form three hydrogen bonds. Thus if a nucleic acid sequence contains the following sequence of bases, thymine, adenine, guanine and cytosine, a "complement" of this nucleic acid molecule would be a molecule containing adenine in the place of thymine, thymine in the place of adenine, cytosine in the place of guanine, and guanine in the place of cytosine. Because the complement can contain a nucleic acid sequence that forms optimal interactions with the parent nucleic acid molecule, such a complement can bind with high affinity to its parent molecule.

With respect to single stranded nucleic acids, particularly oligonucleotides, the term "specifically hybridizing" refers to the association between two single-stranded nucleotide molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence. For example, specific hybridization can refer to a sequence which hybridizes to any autism specific marker gene or nucleic acid, but does not hybridize to other nucleotides. Also polynucleotide which "specifically hybridizes" may hybridize only to a neurospecific specific marker, such an autism-specific marker shown in the Tables contained herein. Appropriate conditions enabling specific hybridization of single stranded nucleic acid molecules of varying complementarity are well known in the art.

For instance, one common formula for calculating the stringency conditions required to achieve hybridization between nucleic acid molecules of a specified sequence homology is set forth below (Sambrook et al., *Molecular Cloning*, Cold Spring Harbor Laboratory (1989):

$$T_m = 81.5°C + 16.6 \log [Na+] + 0.41 (\% G+C) - 0.63 (\% \text{formamide}) - 600/\#bp \text{ in duplex}$$

As an illustration of the above formula, using [Na+]= [0.368] and 50% formamide, with GC content of 42% and an average probe size of 200 bases, the $T_m$ is 57° C. The $T_m$ of a DNA duplex decreases by 1-1.5" C with every 1% decrease in homology. Thus, targets with greater than about 75% sequence identity would be observed using a hybridization temperature of 42" C.

The stringency of the hybridization and wash depend primarily on the salt concentration and temperature of the solutions. In general, to maximize the rate of annealing of the probe with its target, the hybridization is usually carried out at salt and temperature conditions that are 20-25° C. below the calculated $T_m$ of the hybrid. Wash conditions should be as stringent as possible for the degree of identity of the probe for the target. In general, wash conditions are selected to be approximately 12-20° C. below the $T_m$ of the hybrid. In regards to the nucleic acids of the current invention, a moderate stringency hybridization is defined as hybridization in 6×SSC, 5×Denhardt's solution, 0.5% SDS and 100 µg/ml denatured salmon sperm DNA at 42° C., and washed in 2×SSC and 0.5% SDS at 55° C. for 15 minutes. A high stringency hybridization is defined as hybridization in 6×SSC, 5×Denhardt's solution, 0.5% SDS and 100 µg/ml denatured salmon sperm DNA at 42° C., and washed in 1×SSC and 0.5% SDS at 65° C. for 15 minutes. A very high stringency hybridization is defined as hybridization in 6×SSC, 5×Denhardt's solution, 0.5% SDS and 100 µg/ml denatured salmon sperm DNA at 42° C., and washed in 0.1×SSC and 0.5% SDS at 65° C. for 15 minutes.

The term "oligonucleotide," as used herein is defined as a nucleic acid molecule comprised of two or more ribo- or deoxyribonucleotides, preferably more than three. The exact size of the oligonucleotide will depend on various factors and on the particular application and use of the oligonucleotide. Oligonucleotides, which include probes and primers, can be any length from 3 nucleotides to the full length of the nucleic acid molecule, and explicitly include every possible number of contiguous nucleic acids from 3 through the full length of the polynucleotide. Preferably, oligonucleotides are at least about 10 nucleotides in length, more preferably at least 15 nucleotides in length, more preferably at least about 20 nucleotides in length.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and use of the method. For example, for diagnostic applications, depending on the complexity of the target sequence, the oligonucleotide probe typically contains 15-25 or more nucleotides, although it may contain fewer nucleotides. The probes herein are selected to be complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically 15-25 or more nucleotides in length. The primer must be of sufficient complementarity to the desired template to prime the synthesis of the desired extension product, that is, to be able anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

Polymerase chain reaction (PCR) has been described in U.S. Pat. Nos. 4,683,195, 4,800,195, and 4,965,188, the entire disclosures of which are incorporated by reference herein.

The term "vector" relates to a single or double stranded circular nucleic acid molecule that can be infected, transfected or transformed into cells and replicate independently or within the host cell genome. A circular double stranded nucleic acid molecule can be cut and thereby linearized upon treatment with restriction enzymes. An assortment of vectors, restriction enzymes, and the knowledge of the nucleotide sequences that are targeted by restriction enzymes are readily available to those skilled in the art, and include any replicon, such as a plasmid, cosmid, bacmid, phage or virus, to which another genetic sequence or element (either DNA or RNA) may be attached so as to bring about the replication of the attached sequence or element. A nucleic acid molecule of the invention can be inserted into a vector by cutting the vector with restriction enzymes and ligating the two pieces together.

Many techniques are available to those skilled in the art to facilitate transformation, transfection, or transduction of the expression construct into a prokaryotic or eukaryotic organism. The terms "transformation", "transfection", and "transduction" refer to methods of inserting a nucleic acid and/or expression construct into a cell or host organism. These methods involve a variety of techniques, such as treating the cells with high concentrations of salt, an electric field, or detergent, to render the host cell outer membrane or wall permeable to nucleic acid molecules of interest, microinjection, PEG-fusion, and the like.

The term "promoter element" describes a nucleotide sequence that is incorporated into a vector that, once inside an appropriate cell, can facilitate transcription factor and/or polymerase binding and subsequent transcription of portions of the vector DNA into mRNA. In one embodiment, the promoter element of the present invention precedes the 5' end of the Autism specific marker nucleic acid molecule such that the latter is transcribed into mRNA. Host cell machinery then translates mRNA into a polypeptide.

Those skilled in the art will recognize that a nucleic acid vector can contain nucleic acid elements other than the promoter element and the autism specific marker gene nucleic acid molecule. These other nucleic acid elements include, but are not limited to, origins of replication, ribosomal binding sites, nucleic acid sequences encoding drug resistance enzymes or amino acid metabolic enzymes, and nucleic acid sequences encoding secretion signals, localization signals, or signals useful for polypeptide purification.

A "replicon" is any genetic element, for example, a plasmid, cosmid, bacmid, plastid, phage or virus, that is capable of replication largely under its own control. A replicon may be either RNA or DNA and may be single or double stranded.

An "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the expression of a polypeptide coding sequence in a host cell or organism.

As used herein, the terms "reporter," "reporter system", "reporter gene," or "reporter gene product" shall mean an operative genetic system in which a nucleic acid comprises a gene that encodes a product that when expressed produces a reporter signal that is a readily measurable, e.g., by biological assay, immunoassay, radio immunoassay, or by colorimetric, fluorogenic, chemiluminescent or other methods. The nucleic acid may be either RNA or DNA, linear or circular, single or double stranded, antisense or sense polarity, and is operatively linked to the necessary control elements for the expression of the reporter gene product. The required control elements will vary according to the nature of the reporter system and whether the reporter gene is in the form of DNA or RNA, but may include, but not be limited to, such elements as promoters, enhancers, translational control sequences, poly A addition signals, transcriptional termination signals and the like.

The introduced nucleic acid may or may not be integrated (covalently linked) into nucleic acid of the recipient cell or organism. In bacterial, yeast, plant and mammalian cells, for example, the introduced nucleic acid may be maintained as an episomal element or independent replicon such as a plasmid. Alternatively, the introduced nucleic acid may become integrated into the nucleic acid of the recipient cell or organism and be stably maintained in that cell or organism and further passed on or inherited to progeny cells or organisms of the recipient cell or organism. Finally, the introduced nucleic acid may exist in the recipient cell or host organism only transiently.

The term "selectable marker gene" refers to a gene that when expressed confers a selectable phenotype, such as antibiotic resistance, on a transformed cell.

The term "operably linked" means that the regulatory sequences necessary for expression of the coding sequence are placed in the DNA molecule in the appropriate positions relative to the coding sequence so as to effect expression of the coding sequence. This same definition is sometimes applied to the arrangement of transcription units and other transcription control elements (e.g. enhancers) in an expression vector.

The terms "recombinant organism," or "transgenic organism" refer to organisms which have a new combination of genes or nucleic acid molecules. A new combination of genes or nucleic acid molecules can be introduced into an organism using a wide array of nucleic acid manipulation techniques available to those skilled in the art. The term "organism" relates to any living being comprised of a least one cell. An organism can be as simple as one eukaryotic cell or as complex as a mammal. Therefore, the phrase "a recombinant organism" encompasses a recombinant cell, as well as eukaryotic and prokaryotic organism.

The term "isolated protein" or "isolated and purified protein" is sometimes used herein. This term refers primarily to a protein produced by expression of an isolated nucleic acid molecule of the invention. Alternatively, this term may refer to a protein that has been sufficiently separated from other proteins with which it would naturally be associated, so as to exist in "substantially pure" form. "Isolated" is not meant to exclude artificial or synthetic mixtures with other compounds or materials, or the presence of impurities that do not interfere with the fundamental activity, and that may be present, for example, due to incomplete purification, addition of stabilizers, or compounding into, for example, immunogenic preparations or pharmaceutically acceptable preparations.

A "specific binding pair" comprises a specific binding member (sbm) and a binding partner (bp) which have a particular specificity for each other and which in normal conditions bind to each other in preference to other molecules. Examples of specific binding pairs are antigens and antibodies, ligands and receptors and complementary nucleotide sequences. The skilled person is aware of many other examples. Further, the term "specific binding pair" is also applicable where either or both of the specific binding member and the binding partner comprise a part of a large molecule. In embodiments in which the specific binding pair comprises nucleic acid sequences, they will be of a length to hybridize to each other under conditions of the assay, preferably greater than 10 nucleotides long, more preferably greater than 15 or 20 nucleotides long.

"Sample" or "patient sample" or "biological sample" generally refers to a sample which may be tested for a particular molecule, preferably an autism specific marker molecule, such as a marker shown in the tables provided below. Samples may include but are not limited to cells, body fluids, including blood, serum, plasma, urine, saliva, cerebral spinal fluid, tears, pleural fluid and the like.

The terms "agent" and "test compound" are used interchangeably herein and denote a chemical compound, a mixture of chemical compounds, a biological macromolecule, or an extract made from biological materials such as bacteria, plants, fungi, or animal (particularly mammalian) cells or tissues. Biological macromolecules include siRNA, shRNA, antisense oligonucleotides, peptides, peptide/DNA complexes, and any nucleic acid based molecule which exhibits the capacity to modulate the activity of the SNP and/or CNV containing nucleic acids described herein or their encoded proteins. Agents are evaluated for potential biological activity by inclusion in screening assays described hereinbelow.

Methods of Using Autism-Associated CNVS and/or SNPS for Diagnosing a Propensity for the Development of Autism and Autistic Spectrum Disorders Autism-related-CNV and/or SNP containing nucleic acids, including but not limited to those listed in the Tables provided below may be used for a variety of purposes in accordance with the present invention. Autism-associated CNV/SNP containing DNA, RNA, or fragments thereof may be used as probes to detect the presence of and/or expression of autism specific markers. Methods in which autism specific marker nucleic acids may be utilized as probes for such assays include, but are not limited to: (1) in situ hybridization; (2) Southern hybridization (3) northern hybridization; and (4) assorted amplification reactions such as polymerase chain reactions (PCR).

Further, assays for detecting autism-associated CNVs/SNPs may be conducted on any type of biological sample, including but not limited to body fluids (including blood, urine, serum, cerebral spinal fluid, gastric lavage), any type of cell (such as brain cells, white blood cells, mononuclear cells) or body tissue.

From the foregoing discussion, it can be seen that autism-associated CNV/SNP containing nucleic acids, vectors expressing the same, autism CNV/SNP containing marker proteins and anti-Autism specific marker antibodies of the invention can be used to detect autism associated CNVs/SNPs in body tissue, cells, or fluid, and alter autism SNP containing marker protein expression for purposes of assessing the genetic and protein interactions involved in the development of autism.

In most embodiments for screening for autism-associated CNVs/SNPs, the autism-associated CNV/SNP containing nucleic acid in the sample will initially be amplified, e.g. using PCR, to increase the amount of the templates as compared to other sequences present in the sample. This allows the target sequences to be detected with a high degree of sensitivity if they are present in the sample. This initial step may be avoided by using highly sensitive array techniques that are becoming increasingly important in the art. Alternatively, new detection technologies can overcome this limitation and enable analysis of small samples containing as little as 1 µg of total RNA. Using Resonance Light Scattering (RLS) technology, as opposed to traditional fluorescence techniques, multiple reads can detect low quantities of mRNAs using biotin labeled hybridized targets and anti-biotin antibodies. Another alternative to PCR amplification involves planar wave guide technology (PWG) to increase signal-to-noise ratios and reduce background interference. Both techniques are commercially available from Qiagen Inc. (USA).

Thus any of the aforementioned techniques may be used to detect or quantify autism-associated CNV/SNP marker expression and accordingly, diagnose autism.

Kits and Articles of Manufacture

Any of the aforementioned products can be incorporated into a kit which may contain a autism-associated CNV/SNP specific marker polynucleotide or one or more such markers immobilized on a Gene Chip, an oligonucleotide, a polypeptide, a peptide, an antibody, a label, marker, or reporter, a pharmaceutically acceptable carrier, a physiologically acceptable carrier, instructions for use, a container, a vessel for administration, an assay substrate, or any combination thereof.

Methods of Using Autism-Associated CNVS/SNPS for Development of Therapeutic Agents Since the CNVs and SNPs identified herein have been associated with the etiology of autism, methods for identifying agents that modulate the activity of the genes and their encoded products containing such CNVs/SNPs should result in the generation of efficacious therapeutic agents for the treatment of a variety of disorders associated with this condition.

As can be seen from the data provided in the Tables, several chromosomes contain regions which provide suitable targets for the rational design of therapeutic agents which modulate their activity. Small peptide molecules corresponding to these regions may be used to advantage in the design of therapeutic agents which effectively modulate the activity of the encoded proteins.

Molecular modeling should facilitate the identification of specific organic molecules with capacity to bind to the active site of the proteins encoded by the CNV/SNP containing nucleic acids based on conformation or key amino acid residues required for function. A combinatorial chemistry approach will be used to identify molecules with greatest activity and then iterations of these molecules will be developed for further cycles of screening.

The polypeptides or fragments employed in drug screening assays may either be free in solution, affixed to a solid support or within a cell. One method of drug screening utilizes eukaryotic or prokaryotic host cells which are stably transformed with recombinant polynucleotides expressing the polypeptide or fragment, preferably in competitive binding assays. Such cells, either in viable or fixed form, can be used for standard binding assays. One may determine, for example, formation of complexes between the polypeptide or fragment and the agent being tested, or examine the degree to which the formation of a complex between the polypeptide or fragment and a known substrate is interfered with by the agent being tested.

Another technique for drug screening provides high throughput screening for compounds having suitable binding affinity for the encoded polypeptides and is described in detail in Geysen, PCT published application WO 84/03564, published on Sep. 13, 1984. Briefly stated, large numbers of different, small peptide test compounds, such as those described above, are synthesized on a solid substrate, such as plastic pins or some other surface. The peptide test compounds are reacted with the target polypeptide and washed. Bound polypeptide is then detected by methods well known in the art.

A further technique for drug screening involves the use of host eukaryotic cell lines or cells (such as described above)

which have a nonfunctional or altered autism associated gene. These host cell lines or cells are defective at the polypeptide level. The host cell lines or cells are grown in the presence of drug compound. The rate of cellular metabolism of the host cells is measured to determine if the compound is capable of regulating the cellular metabolism in the defective cells. Host cells contemplated for use in the present invention include but are not limited to bacterial cells, fungal cells, insect cells, mammalian cells, and plant cells. The autism-associated CNV/SNP encoding DNA molecules may be introduced singly into such host cells or in combination to assess the phenotype of cells conferred by such expression. Methods for introducing DNA molecules are also well known to those of ordinary skill in the art. Such methods are set forth in Ausubel et al. eds., Current Protocols in Molecular Biology, John Wiley & Sons, NY, N.Y. 1995, the disclosure of which is incorporated by reference herein.

A wide variety of expression vectors are available that can be modified to express the novel DNA sequences of this invention. The specific vectors exemplified herein are merely illustrative, and are not intended to limit the scope of the invention. Expression methods are described by Sambrook et al. Molecular Cloning: A Laboratory Manual or Current Protocols in Molecular Biology 16.3-17.44 (1989). Expression methods in *Saccharomyces* are also described in Current Protocols in Molecular Biology (1989).

Suitable vectors for use in practicing the invention include prokaryotic vectors such as the pNH vectors (Stratagene Inc., 11099 N. Torrey Pines Rd., La Jolla, Calif. 92037), pET vectors (Novogen Inc., 565 Science Dr., Madison, Wis. 53711) and the pGEX vectors (Pharmacia LKB Biotechnology Inc., Piscataway, N.J. 08854). Examples of eukaryotic vectors useful in practicing the present invention include the vectors pRc/CMV, pRc/RSV, and pREP (Invitrogen, 11588 Sorrento Valley Rd., San Diego, Calif. 92121); pcDNA3.1N5&His (Invitrogen); baculovirus vectors such as pVL1392, pVL1393, or pAC360 (Invitrogen); and yeast vectors such as YRP17, YIPS, and YEP24 (New England Biolabs, Beverly, Mass.), as well as pRS403 and pRS413 Stratagene Inc.); Picchia vectors such as pHIL-D1 (Phillips Petroleum Co., Bartlesville, Okla. 74004); retroviral vectors such as PLNCX and pLPCX (Clontech); and adenoviral and adeno-associated viral vectors.

Promoters for use in expression vectors of this invention include promoters that are operable in prokaryotic or eukaryotic cells. Promoters that are operable in prokaryotic cells include lactose (lac) control elements, bacteriophage lambda (pL) control elements, arabinose control elements, tryptophan (trp) control elements, bacteriophage T7 control elements, and hybrids thereof. Promoters that are operable in eukaryotic cells include Epstein Barr virus promoters, adenovirus promoters, SV40 promoters, Rous Sarcoma Virus promoters, cytomegalovirus (CMV) promoters, baculovirus promoters such as AcMNPV polyhedrin promoter, Picchia promoters such as the alcohol oxidase promoter, and *Saccharomyces* promoters such as the gal4 inducible promoter and the PGK constitutive promoter, as well as neuronal-specific platelet-derived growth factor promoter (PDGF), the Thy-1 promoter, the hamster and mouse Prion promoter (MoPrP), and the Glial fibrillar acidic protein (GFAP) for the expression of transgenes in glial cells.

In addition, a vector of this invention may contain any one of a number of various markers facilitating the selection of a transformed host cell. Such markers include genes associated with temperature sensitivity, drug resistance, or enzymes associated with phenotypic characteristics of the host organisms.

Host cells expressing the autism-associated CNVs/SNPs of the present invention or functional fragments thereof provide a system in which to screen potential compounds or agents for the ability to modulate the development of autism. Thus, in one embodiment, the nucleic acid molecules of the invention may be used to create recombinant cell lines for use in assays to identify agents which modulate aspects of cellular metabolism associated with neuronal signaling and neuronal cell communication and structure. Also provided herein are methods to screen for compounds capable of modulating the function of proteins encoded by CNV/SNP containing nucleic acids.

Another approach entails the use of phage display libraries engineered to express fragment of the polypeptides encoded by the CNV/SNP containing nucleic acids on the phage surface. Such libraries are then contacted with a combinatorial chemical library under conditions wherein binding affinity between the expressed peptide and the components of the chemical library may be detected. U.S. Pat. Nos. 6,057,098 and 5,965,456 provide methods and apparatus for performing such assays. Such compound libraries are commercially available from a number of companies including but not limited to Maybridge Chemical Co., (Trevillet, Cornwall, UK), Comgenex (Princeton, N.J.), Microsour (New Milford, Conn.) Aldrich (Milwaukee, Wis.) Akos Consulting and Solutions GmbH (Basel, Switzerland), Ambinter (Paris, France), Asinex (Moscow, Russia) Aurora (Graz, Austria), BioFocus DPI (Switzerland), Bionet (Camelford, UK), Chembridge (San Diego, Calif.), Chem Div (San Diego, Calif.). The skilled person is aware of other sources and can readily purchase the same. Once therapeutically efficacious compounds are identified in the screening assays described herein, the can be formulated in to pharmaceutical compositions and utilized for the treatment of autism.

The goal of rational drug design is to produce structural analogs of biologically active polypeptides of interest or of small molecules with which they interact (e.g., agonists, antagonists, inhibitors) in order to fashion drugs which are, for example, more active or stable forms of the polypeptide, or which, e.g., enhance or interfere with the function of a polypeptide in vivo. See, e.g., Hodgson, (1991) Bio/Technology 9:19-21. In one approach, discussed above, the three-dimensional structure of a protein of interest or, for example, of the protein-substrate complex, is solved by x-ray crystallography, by nuclear magnetic resonance, by computer modeling or most typically, by a combination of approaches. Less often, useful information regarding the structure of a polypeptide may be gained by modeling based on the structure of homologous proteins. An example of rational drug design is the development of HIV protease inhibitors (Erickson et al., (1990) Science 249:527-533). In addition, peptides may be analyzed by an alanine scan (Wells, (1991) Meth. Enzym. 202:390-411). In this technique, an amino acid residue is replaced by Ala, and its effect on the peptide's activity is determined. Each of the amino acid residues of the peptide is analyzed in this manner to determine the important regions of the peptide.

It is also possible to isolate a target-specific antibody, selected by a functional assay, and then to solve its crystal structure. In principle, this approach yields a pharmacore upon which subsequent drug design can be based.

One can bypass protein crystallography altogether by generating anti-idiotypic antibodies (anti-ids) to a functional, pharmacologically active antibody. As a mirror image of a mirror image, the binding site of the anti-ids would be expected to be an analog of the original molecule. The anti-id could then be used to identify and isolate peptides from banks of chemically or biologically produced banks of peptides. Selected peptides would then act as the pharmacore.

Thus, one may design drugs which have, e.g., improved polypeptide activity or stability or which act as inhibitors, agonists, antagonists, etc. of polypeptide activity. By virtue of the availability of CNV/SNP containing nucleic acid sequences described herein, sufficient amounts of the encoded polypeptide may be made available to perform such analytical studies as x-ray crystallography. In addition, the knowledge of the protein sequence provided herein will guide those employing computer modeling techniques in place of, or in addition to x-ray crystallography.

In another embodiment, the availability of autism-associated CNV/SNP containing nucleic acids enables the production of strains of laboratory mice carrying the autism-associated CNVs/SNPs of the invention. Transgenic mice expressing the autism-associated CNV/SNP of the invention provide a model system in which to examine the role of the protein encoded by the SNP containing nucleic acid in the development and progression towards autism. Methods of introducing transgenes in laboratory mice are known to those of skill in the art. Three common methods include: 1. integration of retroviral vectors encoding the foreign gene of interest into an early embryo; 2. injection of DNA into the pronucleus of a newly fertilized egg; and 3. the incorporation of genetically manipulated embryonic stem cells into an early embryo. Production of the transgenic mice described above will facilitate the molecular elucidation of the role that a target protein plays in various cellular metabolic and neuronal processes. Such mice provide an in vivo screening tool to study putative therapeutic drugs in a whole animal model and are encompassed by the present invention.

The term "animal" is used herein to include all vertebrate animals, except humans. It also includes an individual animal in all stages of development, including embryonic and fetal stages. A "transgenic animal" is any animal containing one or more cells bearing genetic information altered or received, directly or indirectly, by deliberate genetic manipulation at the subcellular level, such as by targeted recombination or microinjection or infection with recombinant virus. The term "transgenic animal" is not meant to encompass classical cross-breeding or in vitro fertilization, but rather is meant to encompass animals in which one or more cells are altered by or receive a recombinant DNA molecule. This molecule may be specifically targeted to a defined genetic locus, be randomly integrated within a chromosome, or it may be extrachromosomally replicating DNA. The term "germ cell line transgenic animal" refers to a transgenic animal in which the genetic alteration or genetic information was introduced into a germ line cell, thereby conferring the ability to transfer the genetic information to offspring. If such offspring, in fact, possess some or all of that alteration or genetic information, then they, too, are transgenic animals.

The alteration of genetic information may be foreign to the species of animal to which the recipient belongs, or foreign only to the particular individual recipient, or may be genetic information already possessed by the recipient. In the last case, the altered or introduced gene may be expressed differently than the native gene. Such altered or foreign genetic information would encompass the introduction of autism-associated CNV/SNP containing nucleotide sequences.

The DNA used for altering a target gene may be obtained by a wide variety of techniques that include, but are not limited to, isolation from genomic sources, preparation of cDNAs from isolated mRNA templates, direct synthesis, or a combination thereof.

A preferred type of target cell for transgene introduction is the embryonal stem cell (ES). ES cells may be obtained from pre-implantation embryos cultured in vitro (Evans et al., (1981) Nature 292:154-156; Bradley et al., (1984) Nature 309:255-258; Gossler et al., (1986) Proc. Natl. Acad. Sci. 83:9065-9069). Transgenes can be efficiently introduced into the ES cells by standard techniques such as DNA transfection or by retrovirus-mediated transduction. The resultant transformed ES cells can thereafter be combined with blastocysts from a non-human animal. The introduced ES cells thereafter colonize the embryo and contribute to the germ line of the resulting chimeric animal.

One approach to the problem of determining the contributions of individual genes and their expression products is to use isolated autism-associated CNV/SNP genes as insertional cassettes to selectively inactivate a wild-type gene in totipotent ES cells (such as those described above) and then generate transgenic mice. The use of gene-targeted ES cells in the generation of gene-targeted transgenic mice was described, and is reviewed elsewhere (Frohman et al., (1989) Cell 56:145-147; Bradley et al., (1992) Bio/Technology 10:534-539).

Techniques are available to inactivate or alter any genetic region to a mutation desired by using targeted homologous recombination to insert specific changes into chromosomal alleles. However, in comparison with homologous extrachromosomal recombination, which occurs at a frequency approaching 100%, homologous plasmid-chromosome recombination was originally reported to only be detected at frequencies between $10^{-6}$ and $10^{-3}$. Nonhomologous plasmid-chromosome interactions are more frequent occurring at levels $10^5$-fold to $10^2$ fold greater than comparable homologous insertion.

To overcome this low proportion of targeted recombination in murine ES cells, various strategies have been developed to detect or select rare homologous recombinants. One approach for detecting homologous alteration events uses the polymerase chain reaction (PCR) to screen pools of transformant cells for homologous insertion, followed by screening of individual clones. Alternatively, a positive genetic selection approach has been developed in which a marker gene is constructed which will only be active if homologous insertion occurs, allowing these recombinants to be selected directly. One of the most powerful approaches developed for selecting homologous recombinants is the positive-negative selection (PNS) method developed for genes for which no direct selection of the alteration exists. The PNS method is more efficient for targeting genes which are not expressed at high levels because the marker gene has its own promoter. Non-homologous recombinants are selected against by using the Herpes Simplex virus thymidine kinase (HSV-TK) gene and selecting against its non-homologous insertion with effective herpes drugs such as gancyclovir (GANC) or (1-(2-deoxy-2-fluoro-B-D arabinofluranosyl)-5-iodou-racil, (FIAU). By this counter selection, the number of homologous recombinants in the surviving transformants can be increased. Utilizing autism-associated SNP containing nucleic acid as a targeted insertional cassette provides means to detect a successful insertion as visualized, for example, by acquisition of immunoreactivity to an antibody immunologically specific for the polypeptide encoded by autism-associated SNP nucleic acid and, therefore, facilitates screening/selection of ES cells with the desired genotype.

As used herein, a knock-in animal is one in which the endogenous murine gene, for example, has been replaced with human autism-associated CNV/SNP containing gene of the invention. Such knock-in animals provide an ideal model system for studying the development of autism.

As used herein, the expression of a autism-associated CNV/SNP containing nucleic acid, fragment thereof, or an autism-associated CNV/SNP fusion protein can be targeted in a "tissue specific manner" or "cell type specific manner" using a vector in which nucleic acid sequences encoding all or a portion of autism-associated CNV/SNP are operably linked to regulatory sequences (e.g., promoters and/or enhancers) that direct expression of the encoded protein in a particular tissue or cell type. Such regulatory elements may be used to advantage for both in vitro and in vivo applications. Promoters for directing tissue specific proteins are well known in the art and described herein.

The nucleic acid sequence encoding the autism-associated CNV/SNP of the invention may be operably linked to a variety of different promoter sequences for expression in transgenic animals. Such promoters include, but are not limited to a prion gene promoter such as hamster and mouse Prion promoter (MoPrP), described in U.S. Pat. No. 5,877,399 and in Borchelt et al., Genet. Anal. 13 (6) (1996) pages 159-163; a rat neuronal specific enolase promoter, described in U.S. Pat. Nos. 5,612,486, and 5,387,742; a platelet-derived growth factor B gene promoter, described in U.S. Pat. No. 5,811,633; a brain specific dystrophin promoter, described in U.S. Pat. No. 5,849,999; a Thy-1 promoter; a PGK promoter; a CMV promoter; a neuronal-specific platelet-derived growth factor B gene promoter; and Glial fibrillar acidic protein (GFAP) promoter for the expression of transgenes in glial cells.

Methods of use for the transgenic mice of the invention are also provided herein. Transgenic mice into which a nucleic acid containing the autism-associated CNV/SNP or its encoded protein have been introduced are useful, for example, to develop screening methods to screen therapeutic agents to identify those capable of modulating the development of autism.

Pharmaceuticals and Peptide Therapies

The elucidation of the role played by the autism associated CNVs/SNPs described herein in neuronal signaling and brain structure facilitates the development of pharmaceutical compositions useful for treatment and diagnosis of autism. These compositions may comprise, in addition to one of the above substances, a pharmaceutically acceptable excipient, carrier, buffer, stabilizer or other materials well known to those skilled in the art. Such materials should be non-toxic and should not interfere with the efficacy of the active ingredient. The precise nature of the carrier or other material may depend on the route of administration, e.g. oral, intravenous, cutaneous or subcutaneous, nasal, intramuscular, intraperitoneal routes.

Whether it is a polypeptide, antibody, peptide, nucleic acid molecule, small molecule or other pharmaceutically useful compound according to the present invention that is to be given to an individual, administration is preferably in a "prophylactically effective amount" or a "therapeutically effective amount" (as the case may be, although prophylaxis may be considered therapy), this being sufficient to show benefit to the individual.

The following examples are provided to illustrate certain embodiments of the invention. They are not intended to limit the invention in any way.

The following materials and methods are provided to facilitate the practice of the present invention.

The Autism cohort consisted of 1200 autism cases who belonged to either nuclear family trios (one affected child and two parents) or multiplex families, where only one affected individual was randomly selected for genotyping. All patients were diagnosed under the age of 12 years and fulfilled the standard ADI-R and/or ADOS criteria. Ethnic backgrounds were mixed with the largest single subset of European descent (n=900). Only subjects of European ancestry were used in the analysis. The Research Ethics Board of the respective Hospitals and other participating centers approved the study, and written informed consent was obtained from all subjects.

Detailed information about the study replication cohort is available on the AGRE website. AGRE samples were also collected in the United States and most subjects were of European ancestry; only subjects of European ancestry were used in the replication analysis.

The control group included 2000 children with self reported Caucasian status, mean age 9.42 years; 53.05% male and 46.95% female, who did not have autism or ASD. These individual were recruited by CHOP's clinicians and nursing staff within the CHOP's Health Care Network, including four primary care clinics and several group practices and outpatient practices that included well child visits. The Research Ethics Board of CHOP approved the study, and written informed consent was obtained from all subjects.

We performed high throughput genome-wide SNP genotyping, using the Illumina Infinium™ II HumanHap550 BeadChip technology[9,10] (Illumina, San Diego), at the Center for Applied Genomics at CHOP, as previously described[11].

Example I

For the case-control comparison, we genotyped 1200 autism probands, most of which came from sporadic/simplex autism families and 2000 unrelated controls of European ancestry (based on self report with approximately 561,466 single nucleotide polymorphisms (SNPs) using the Illumina Human Hap550 Genotyping BeadChip platform[9]. All patients had clinically proven autism based on standard ADI-R and/or ADOS criteria. Of the 561,466 SNPs, 5254 failed to meet a call frequency of 90%, 16,391 SNPs had less than 1% MAF and 15,264 SNPs failed Hardy-Weinberg Equilibrium (HWE) and were discarded. This results in a set of 524,557 SNPs being used for GWA analysis. We genotyped 5,975 samples obtained from autistic children, unaffected siblings, and parents. Of those, 316 fell below a call rate threshold of 98.0% and were excluded. Thus, 5,659 samples had genotyping call rate above 97.5%. The autism patients and control subjects came from two separate sample sets. I: A mixture of simplex and multiplex families from CHOP/Seattle, that included 1,057 autism cases, 582 parents and 2518 unaffected controls. II: Multiplex families from AGRE that included 1697 autism cases and 2323 unaffected siblings or parents from 932 unique families. In the case-control analysis, single-marker allele frequencies were compared using $\chi^2$ statistics for all markers. As shown in Table 1, we identified one SNP (rs2381595) that met genome-wide significance at the 0.05 level after Bonferroni correction. Upon further examination, the allelic frequency of the rare allele was rare, at 2% in cases and 0.6% in the controls and the SNP showed signal only in the case-control analysis (negative in the PDT analysis) and it was the only SNP in the region that showed signal suggesting it may be spurious. Table 1 lists SNPs with suggestive P values (nominal P<1×10$^{-5}$).

We also performed a genome-wide search for CNV association to the autism phenotype. The data quality was strictly filtered based on a call rate above 98%, populations of cases and controls which closely stratified based on Ancestry Informative Markers (AIMs) clustering, a standard deviation of normalized intensity below 0.35, low waviness of intensity corresponding with GC content, and a maximum count of 40 CNVs per individual. This resulted in 2072 autism cases and 2518 controls. Utilizing a Hidden Markov Model (HMM) approach, the most probable CNV state is reported for a contiguous sequence of SNPs for each individual sample. We first searched for replication of CNVs previously reported to associate with the autism or ASD phenotypes, including but not limited to NRXN1, SHANK3, AUTS2 and NLGN3. As shown in Table 2, NRXN1 was the only previously reported gene that we could confirm through CNV association (P=0.017). There was no evidence for association to the remaining genes. SNP based whole genome CNV association was preformed to capture the most significant points in complex CNV overlap between case and control populations. A chi square statistic is applied to the CNV observance of deletion and duplication for each SNP. To present results in a non-redundant manner, statistical local minimums are reported in reference to a region of nominal significance including SNPs residing within 1 MB. We identified regions of novel (Table 3) and overrepresented (Table 4) CNVs in Autism using this approach. The majority of CNVs have replication between blood derived samples form a Seattle/CHOP consortium and cell line samples from Autism Genetic Research Exchange (AGRE). The most significant association is POTE8 (protein expressed in prostate, ovary, and testis) (p=1.36$^{-11}$).

To focus on gene content for direct functional confirmation of relation to autism, analysis was preformed for only CNVs directly impacting gene content. The gene based approach is more flexible to capture imperfect overlap of CNVs which may be impacting the same gene at different positions. Individual CNV calls were annotated with gene content to establish top candidate genes for autism. We identified regions of novel (Table 5) and overrepresented (Table 6) CNVs in autism using this approach. Table 7 lists other nominally significant CNVs. One of the highly significant result from this approach (p=4.5$^{-15}$) includes a CNV that results in a deletion of the MGAM (maltase-glucoamylase) gene, a brush border membrane enzyme that plays a role in the final steps of digestion of starch. The gene is primarily expressed in the microvilli lining of the intestine and is involved with the digestion of starch; when starch is not digested the intestine serves as a breeding ground for bacteria which create D-lactic acid and dermorphin as products of their metabolism. These metabolites have been shown to be transmitted through the blood brain barrier of the central nervous system (CNS) into the brain and have been associated with bizarre behavior. 41% of AGRE cases have reported GI problems and indigestion, which is s consistent with reports from others showing that 44% of autistic children have GI symptoms compared to 10% for controls.

To address the potential biological role of some of the other genes we identified that included CNVs that were either associated with or overrepresented in autism, we performed Functional Annotation Clustering (FAC) of all the genes listed using the DAVID Bioinformatics Database. We observed that genes that were classified as having synaptic transmission function had the highest enrichment among these autism candidate genes (p=7.1$^{-3}$), and thus have a striking biological relevance to autism. These genes include CNTN4 (Contactin 4), which is involved in formation of axon connections in the developing nervous system; NLGN1 (neuroligin 1), involved in the formation and remodeling of central nervous system synapses; GRID1 (glutamate receptor, ionotropic), L-glutamate acts as an excitatory neurotransmitter; DBH (dopamine beta-hydroxylase) expressed in synaptic vesicles of postganglionic sympathetic neurons, converts dopamine to norepinephrine and has been associated with ADHD; PRIMA1 (proline rich membrane anchor), required to anchor acetylcholinesterase (ACHE) to the basal lamina of the neuromuscular junction and to the membrane of neuronal synapses in brain; DLGAP1 (discs large homolog-associated protein), Part of the postsynaptic scaffold in neuronal cells and interacts with DLG1-4 and SHANK1-3. These genes are novel with respect to autism with the exception of NLGN1. Direct functional relevance with CNVs in these genes to the development of autism is compelling. Several other genes are affected by the CNVs we have observed and while their roles in autism may not be clear at this time, the strength of the association signals suggests that these genes and their neighboring regions predispose to the autism phenotype.

Taken together, these results suggest that the genetic landscape in the pathogenesis of autism involves both common and rare CNVs, which associate with the autism phenotypes, where the rare CNVs are highly heterogeneous and unique to the individual families and cluster on genes that are involved with neuronal signaling and development.

TABLE 1

| CHR | SNP | POSITION | Frequency Affected | Frequency Controls | Eigenstrat CHISQ | Eigenstrat CHISQ P | OR Case-Control | AGRE triads | AGRE dissibs | AGRE families | AGRE PDT CHI2_P | P_COMBINED |
|---|---|---|---|---|---|---|---|---|---|---|---|---|
| 9 | rs2381595 | 37007666 | 0.02769 | 0.006877 | 44.5322 | 2.72E1−12 | 4.112 | 511 | 433 | 409 | 0.799495339 | 6.05E−11 |
| 5 | rs4128686 | 104892450 | 0.03955 | 0.06741 | 6.8618 | 0.014394545 | 0.6761 | 597 | 477 | 457 | 7.93E−06 | 1.94E−06 |
| X | rs6529461 | 129991328 | 0.06377 | 0.1179 | 17.7688 | 1.68E−06 | 0.5097 | 532 | 442 | 429 | 0.076875985 | 2.17E−06 |
| 1 | rs1934496 | 160237735 | 0.4161 | 0.3323 | 33.9684 | 3.61E−07 | 1.432 | 554 | 442 | 442 | 0.630224705 | 3.71E−06 |
| 12 | rs4764776 | 99874597 | 0.4064 | 0.3708 | 6.0213 | 8.37E−04 | 1.162 | 604 | 477 | 460 | 2.76E−04 | 3.76E−06 |
| 14 | rs49133522 | 104217624 | 0.2931 | 0.2276 | 24.1091 | 1.35E−06 | 1.407 | 563 | 470 | 448 | 0.232212007 | 5.00E−06 |
| 20 | rs6089151 | 30080496 | 0 | 0.01698 | 20.7516 | 1.46E−06 | 0 | 514 | 414 | 409 | 0.248213053 | 5.73E−06 |
| X | rs5918959 | 64810327 | 0.01548 | 0.04404 | 21.3576 | 3.17E−05 | 0.3414 | 565 | 459 | 436 | 0.016351223 | 8.02E−06 |
| 1 | rs12023591 | 159638187 | 0.06388 | 0.03885 | 16.3262 | 9.06E−06 | 1.688 | 575 | 468 | 446 | 0.059598446 | 8.33E−06 |
| 7 | rs4722551 | 25765066 | 0.103 | 0.1534 | 20.8667 | 2.35E−06 | 0.6334 | 588 | 469 | 456 | 0.456056535 | 1.58E−05 |
| 5 | rs603015 | 89860791 | 0.419 | 0.4163 | 0.0324 | 0.459751333 | 1.011 | 604 | 483 | 462 | 2.50E−06 | 1.69E−05 |

TABLE 1-continued

| CHR | SNP | POSITION | Frequency Affected | Frequency Controls | Eigenstrat CHISQ | Eigenstrat CHISQ P | OR Case-Control | AGRE triads | AGRE dissibs | AGRE families | AGRE PDT CHI2_P | P_COM-BINED |
|---|---|---|---|---|---|---|---|---|---|---|---|---|
| 5 | rs316738 | 41681308 | 0.2278 | 0.2796 | 15.4596 | 0.002313282 | 0.7601 | 608 | 482 | 463 | 6.38E−04 | 2.19E−05 |
| 5 | rs10942597 | 89843151 | 0.4199 | 0.4183 | 0.0122 | 0.457909386 | 1.007 | 609 | 483 | 463 | 3.46E−06 | 2.27E−05 |
| 11 | rs589916 | 113568572 | 0.3819 | 0.4352 | 11.531 | 2.89E−05 | 0.8019 | 494 | 422 | 415 | 0.056014717 | 2.32E−05 |
| 12 | rs11109986 | 98565778 | 0.3435 | 0.4001 | 15.1472 | 3.77E−04 | 0.7847 | 609 | 483 | 463 | 0.004419684 | 2.38E−05 |
| 7 | rs10229764 | 118338401 | 0.1565 | 0.1191 | 14.5086 | 3.67E−05 | 1.371 | 609 | 483 | 463 | 0.046087623 | 2.42E−05 |
| 5 | rs499148 | 89862482 | 0.4192 | 0.4161 | 0.0464 | 0.464053525 | 1.013 | 607 | 483 | 462 | 3.70E−06 | 2.45E−05 |
| 9 | rs10974293 | 4024589 | 0.3848 | 0.4473 | 17.9842 | 2.54E−06 | 0.773 | 606 | 478 | 461 | 0.717018604 | 2.59E−05 |
| 6 | rs12173338 | 164505661 | 0.0663 | 0.1128 | 24.7814 | 3.14E−05 | 0.5587 | 590 | 477 | 458 | 0.058471143 | 2.61E−05 |
| X | rs2074098 | 13585024 | 0.1272 | 0.1855 | 16.5121 | 1.37E−05 | 0.6397 | 603 | 483 | 461 | 0.098255336 | 2.74E−05 |
| 14 | rs4982398 | 20699037 | 0.1485 | 0.1051 | 21.8249 | 1.58E−05 | 1.485 | 608 | 483 | 462 | 0.123479903 | 2.76E−05 |
| 5 | rs2366773 | 89974343 | 0.3265 | 0.3232 | 0.0572 | 0.666098325 | 1.015 | 607 | 482 | 462 | 3.04E−06 | 2.86E−05 |
| 2 | rs11899300 | 148998705 | 0.2409 | 0.1877 | 20.7578 | 2.55E−05 | 1.373 | 604 | 483 | 459 | 0.084362268 | 3.02E−05 |
| 7 | rs2538971 | 147033577 | 0.1834 | 0.1466 | 12.0134 | 0.005082633 | 1.308 | 609 | 483 | 463 | 4.27E−04 | 3.05E−05 |
| 1 | rs7539958 | 175644925 | 0.3108 | 0.2875 | 3.0286 | 0.052254571 | 1.118 | 609 | 482 | 463 | 4.99E−05 | 3.61E−05 |
| 11 | rs10793345 | 78104970 | 0.1885 | 0.2046 | 1.8018 | 0.22068688 | 0.9033 | 608 | 482 | 463 | 1.28E−06 | 3.90E−05 |
| 2 | rs1524370 | 149032007 | 0.2402 | 0.189 | 19.1812 | 3.17E−05 | 1.356 | 608 | 483 | 462 | 0.092607617 | 4.03E−05 |
| 4 | rs6818194 | 12676567 | 0.04148 | 0.02189 | 18.0316 | 4.96E−05 | 1.934 | 608 | 483 | 462 | 0.061739504 | 4.19E−05 |
| 2 | rs4666334 | 19723523 | 0.1456 | 0.1017 | 22.6216 | 5.01E−05 | 1.504 | 608 | 483 | 461 | 0.06264931 | 4.29E−05 |
| 5 | rs4257797 | 166801773 | 0.4337 | 0.378 | 15.111 | 2.48E−04 | 1.26 | 606 | 481 | 462 | 0.012754679 | 4.32E−05 |
| X | rs7050617 | 115692778 | 0.1229 | 0.1903 | 22.0051 | 7.59E−06 | 0.5962 | 568 | 458 | 448 | 0.419615507 | 4.35E−05 |
| 11 | rs4944214 | 78079887 | 0.1664 | 0.1875 | 3.2755 | 0.085622914 | 0.8654 | 601 | 477 | 459 | 3.83E−05 | 4.47E−05 |
| 6 | rs10872715 | 155605595 | 0.3328 | 0.3045 | 4.0959 | 0.074394356 | 1.139 | 597 | 476 | 458 | 4.51E−05 | 4.56E−05 |
| 7 | rs10275972 | 118363317 | 0.1566 | 0.1194 | 13.925 | 4.90E−05 | 1.369 | 599 | 477 | 458 | 0.069950044 | 4.66E−05 |
| 15 | rs4778719 | 77762687 | 0.2671 | 0.224 | 11.8707 | 6.54E−05 | 1.262 | 608 | 483 | 463 | 0.052769721 | 4.69E−05 |
| 5 | rs11743030 | 89834629 | 0.4817 | 0.4713 | 0.5088 | 0.952155635 | 1.043 | 602 | 478 | 461 | 3.64E−06 | 4.70E−05 |
| 17 | rs9907506 | 36802688 | 0.3197 | 0.28 | 8.4469 | 0.004952781 | 1.209 | 603 | 479 | 459 | 7.16E−04 | 4.80E−05 |
| 2 | rs4432408 | 20321328 | 0.3819 | 0.4529 | 23.147 | 9.99E−06 | 0.7465 | 606 | 480 | 462 | 0.356905699 | 4.83E−05 |
| 2 | r16749689 | 20317750 | 0.3857 | 0.4597 | 25.0781 | 7.68E−06 | 0.7381 | 609 | 483 | 463 | 0.495122135 | 5.13E−05 |
| 13 | rs9318554 | 23918863 | 0.0245 | 0.0511 | 17.6361 | 2.94E−04 | 0.4664 | 560 | 460 | 442 | 0.012986541 | 5.14E−05 |
| 17 | rs2106853 | 36815436 | 0.3239 | 0.285 | 8.1567 | 0.005454287 | 1.202 | 608 | 483 | 462 | 7.02E−05 | 5.16E−05 |
| 10 | rs4935035 | 53806205 | 0.3273 | 0.4111 | 31.3909 | 6.01E−06 | 0.6968 | 591 | 479 | 452 | 0.669815362 | 5.41E−05 |
| 3 | rs688523 | 8909518 | 0.1827 | 0.1848 | 0.031 | 0.60179307 | 0.9864 | 540 | 441 | 432 | 6.85E−06 | 5.52E−05 |
| 20 | rs7267210 | 48923004 | 0.1055 | 0.08137 | 8.5003 | 0.001787773 | 1.332 | 609 | 483 | 463 | 0.002331793 | 5.58E−05 |
| 18 | rs674617 | 9691782 | 0.05641 | 0.08262 | 10.0505 | 0.003062758 | 0.6639 | 523 | 418 | 422 | 0.00141573 | 5.79E−05 |
| 8 | rs10088698 | 48817337 | 0.05053 | 0.09464 | 26.0441 | 6.78E−06 | 0.5091 | 605 | 479 | 460 | 0.644695282 | 5.83E−05 |
| 12 | rs7306259 | 99863543 | 0.2292 | 0.2049 | 4.0372 | 0.00968465 | 1.154 | 590 | 477 | 460 | 4.73E−04 | 6.09E−05 |
| 8 | rs930991 | 9240511 | 0.2074 | 0.2659 | 19.927 | 1.73E−05 | 0.7227 | 609 | 483 | 463 | 0.266975105 | 6.12E−05 |
| 14 | rs7149898 | 37822503 | 0.1702 | 0.213 | 12.8466 | 7.14E−04 | 0.7579 | 565 | 465 | 448 | 0.00658226 | 6.24E−05 |
| 7 | rs13312787 | 11994001 | 0.05969 | 0.08827 | 12.5779 | 9.95E−05 | 0.6239 | 502 | 431 | 413 | 0.048193514 | 6.35E−05 |
| 8 | rs13279614 | 25671940 | 0.2227 | 0.2088 | 1.3223 | 0.156564405 | 1.085 | 609 | 483 | 463 | 3.11E−05 | 6.44E−05 |
| 15 | rs7167802 | 40904198 | 0.3093 | 0.2645 | 11.5732 | 1.46E−04 | 1.245 | 605 | 478 | 462 | 0.033666551 | 6.48E−05 |
| 3 | rs9812475 | 171144788 | 0.007109 | 0.0242 | 14.5362 | 8.37E−04 | 0.2887 | 525 | 420 | 409 | 0.00603956 | 6.67E−05 |
| 20 | rs17296246 | 15143572 | 0.1618 | 0.1213 | 16.5616 | 1.67E−05 | 1.398 | 607 | 483 | 461 | 0.30971241 | 6.81E−05 |
| 20 | rs16995401 | 15098730 | 0.2604 | 0.2071 | 18.1703 | 3.99E−05 | 1.348 | 592 | 472 | 459 | 0.138606906 | 7.25E−05 |
| 15 | rs30951321 | 55363208 | 0.417 | 0.4935 | 27.3995 | 8.40E−06 | 0.7342 | 607 | 483 | 462 | 0.6637398 | 7.31E−05 |
| 8 | rs16917029 | 53060106 | 0.03638 | 0.06472 | 15.0204 | 6.29E−05 | 0.5456 | 594 | 469 | 452 | 0.092507482 | 7.60E−05 |
| 19 | rs2287863 | 8485011 | 0.1635 | 0.1877 | 4.4257 | 0.012971448 | 0.846 | 606 | 482 | 462 | 4.54E−04 | 7.67E−05 |
| 17 | r12191377 | 36662596 | 0.3039 | 0.265 | 8.5962 | 0.006937422 | 1.211 | 609 | 483 | 463 | 8.53E−04 | 7.71E−05 |
| 5 | rs624097 | 41721101 | 0.2424 | 0.2884 | 11.9184 | 0.008207634 | 0.7892 | 609 | 483 | 463 | 7.25E−04 | 7.75E−05 |
| 2 | rs10183349 | 50744486 | 0.2921 | 0.3479 | 15.8459 | 3.38E−04 | 0.7733 | 608 | 483 | 462 | 0.017622113 | 7.75E−05 |
| 15 | rs935326 | 55354536 | 0.4185 | 0.4958 | 27.9029 | 7.69E−06 | 0.7319 | 609 | 482 | 463 | 0.776468515 | 7.78E−05 |
| 7 | rs6969710 | 118498680 | 0.1572 | 0.1233 | 11.5961 | 2.94E−04 | 1.326 | 609 | 483 | 463 | 0.020487607 | 723E−05 |
| 1 | rs6701187 | 178582437 | 0.1601 | 0.1221 | 14.4242 | 8.69E−05 | 1.37 | 606 | 483 | 461 | 0.070460856 | 7.96E−05 |
| 8 | rs10957132 | 61442000 | 0.3486 | 0.3953 | 10.3938 | 2.14E−04 | 0.8187 | 603 | 475 | 459 | 0.029336452 | 8.15E−05 |
| X | rs12392447 | 153288055 | 0.0769 | 0.1243 | 24.1178 | 1.16E−04 | 0.5062 | 533 | 457 | 437 | 0.054254711 | 8.18E−05 |
| 5 | rs10069803 | 101392599 | 0.1507 | 0.1732 | 3.9422 | 0.188717776 | 0.8471 | 579 | 473 | 444 | 339E−05 | 8.29E−05 |
| 5 | rs648166 | 32500173 | 0.2515 | 0.2489 | 0.0413 | 0.421726157 | 1.014 | 599 | 479 | 457 | 1.53E−05 | 8.36E05 |
| 3 | rs2526388 | 50149890 | 0.2285 | 0.2724 | 11.0876 | 7.28E−05 | 0.7914 | 609 | 483 | 463 | 0.089526057 | 8.44E−05 |
| X | rs5980109 | 14872437 | 0.2328 | 0.2683 | 5.4183 | 0.087395761 | 0.8276 | 601 | 482 | 458 | 7.51E−05 | 8.49E−05 |
| 7 | rs4606009 | 48459354 | 0.03566 | 0.05873 | 11.3638 | 2.26E−04 | 0.5927 | 609 | 483 | 463 | 0.030210972 | 8.79E−05 |
| 7 | rs4723021 | 30707899 | 0.08423 | 0.06041 | 10.5439 | 1.67E−04 | 1.431 | 566 | 461 | 442 | 0.043813467 | 9.41E−05 |
| 5 | rs316762 | 41752150 | 0.2434 | 0.288 | 11.1833 | 0.011262 | 0.7953 | 609 | 483 | 463 | 6.57E−04 | 9.48E−05 |
| 1 | rs1467662 | 153878247 | 0.09729 | 0.1436 | 18.2157 | 1.02E−04 | 0.6428 | 578 | 467 | 451 | 0.074199319 | 9.67E−05 |
| 12 | rs4764773 | 99837118 | 0.2318 | 0.2091 | 3.5054 | 0.013016251 | 1.142 | 604 | 480 | 459 | 5.89E−04 | 9.80E−05 |
| 6 | rs11753215 | 75313286 | 0.06934 | 0.07147 | 0.0779 | 0.433998217 | 0.968 | 605 | 480 | 462 | 1.78E−05 | 9.87E−05 |
| 5 | rs3805483 | 89839343 | 0.4782 | 0.4684 | 0.4411 | 0.972365995 | 1.04 | 609 | 483 | 463 | 954E−06 | 1.00E−04 |
| 19 | rs2420416 | 14159442 | 0.2482 | 0.2532 | 0.1523 | 0.401275749 | 0.9734 | 609 | 481 | 462 | 2.85E−05 | 1.00E−04 |
| 12 | rs11610061 | 98552616 | 0.246 | 0.2989 | 15.4287 | 9.13E−05 | 0.7652 | 609 | 483 | 463 | 0.120894492 | 1.00E−04 |
| 7 | rs6973591 | 92805322 | 0.5211 | 0.466 | 13.8415 | 5.46E−05 | 1.247 | 607 | 483 | 462 | 0.166614056 | 1.00E−04 |
| 14 | rs17123938 | 50997181 | 0.09548 | 0.06388 | 17.5278 | 5.05E−05 | 1.547 | 605 | 481 | 460 | 0.179573178 | 1.00E−04 |
| 7 | rs2158044 | 92813050 | 0.5211 | 0.4668 | 13.4826 | 6.38E−05 | 1.243 | 609 | 483 | 463 | 0.184954286 | 1.00E−04 |
| 14 | rs7147817 | 39901754 | 0.516 | 0.46 | 14.4499 | 5.40E−05 | 1.251 | 603 | 482 | 460 | 0.205387771 | 1.00E−04 |
| 15 | rs16963122 | 34539761 | 0.4602 | 0.4003 | 16.3864 | 4.35E−05 | 1.277 | 586 | 478 | 451 | 0.212212205 | 1.00E−04 |
| 11 | rs11221335 | 127891116 | 0.1756 | 0.2293 | 18.6272 | 3.73E−05 | 0.7158 | 599 | 478 | 458 | 0.254241467 | 1.00E−04 |
| 4 | rs8192049 | 140954657 | 0.06186 | 0.03972 | 13.5356 | 4.70E−05 | 1.594 | 609 | 483 | 463 | 0.258720517 | 1.00E−04 |
| 6 | rs454563 | 13403515 | 0.07619 | 0.1168 | 17.1167 | 315E−05 | 0.6236 | 535 | 432 | 433 | 0.356615538 | 1.00E−04 |
| 16 | rs16971464 | 71573644 | 0.05102 | 0.07854 | 13.0532 | 3.21E−05 | 0.6308 | 605 | 475 | 460 | 0.373562157 | 1.00E−04 |

TABLE 1-continued

| CHR | SNP | POSITION | Frequency Affected | Frequency Controls | Eigenstrat CHISQ | Eigenstrat CHISQ P | OR Case-Control | AGRE triads | AGRE dissibs | AGRE families | AGRE PDT CHI2_P | P_COMBINED |
|---|---|---|---|---|---|---|---|---|---|---|---|---|
| 7 | rs984468 | 13660589 | 0.3934 | 0.4445 | 11.8384 | 2.50E−05 | 0.8106 | 529 | 444 | 421 | 0.431317449 | 1.00E−04 |
| 15 | rs2733332 | 55175641 | 0.373 | 0.4425 | 22.8135 | 1.47E−05 | 0.7493 | 595 | 479 | 455 | 0.613328695 | 1.00E−04 |
| 5 | rs490812 | 89942772 | 0.4201 | 0.4103 | 0.4481 | 0.982160245 | 1.041 | 582 | 475 | 450 | 1.75E−05 | 2.00E−04 |
| 3 | rs3804765 | 113188682 | 0.24 | 0.2342 | 0.2146 | 0.424981047 | 1.032 | 581 | 470 | 450 | 4.78E−05 | 2.00E−44 |
| 14 | rs10139298 | 87078008 | 0.3865 | 0.4571 | 22.781 | 9.11E−05 | 0.7482 | 609 | 483 | 463 | 0.146715403 | 2.00E−04 |
| 2 | rs4436949 | 233874392 | 0.2657 | 0.2209 | 12.8911 | 9.61E−05 | 1.277 | 605 | 480 | 461 | 0.174114883 | 2.00E−04 |
| 6 | rs1022249 | 4600281 | 0.2598 | 0.2005 | 23.7764 | 9.49E−05 | 1.399 | 609 | 483 | 463 | 0.204781532 | 2.00E−04 |
| 7 | rs6951952 | 57206491 | 0.2829 | 0.3355 | 13.563 | 8.04E−05 | 0.7816 | 553 | 452 | 438 | 0.975780845 | 8.00E−04 |
| 15 | rs2414491 | 55253067 | 0.4332 | 0.5023 | 21.9837 | 8.95E−05 | 0.7573 | 606 | 478 | 461 | 0.93966645 | 9.00E−04 |
| 1 | rs6426503 | 224957746 | 0.217 | 0.1723 | 15.3069 | 9.44E−05 | 1.332 | 585 | 475 | 449 | 0.972622037 | 9.00E−04 |
| 2 | rs11674953 | 112730311 | 0.3282 | 0.3853 | 15.3579 | 9.07E−05 | 0.7792 | 598 | 474 | 455 | 1 | 9.00E−04 |

TABLE 2

Attempts to replicate CNVs previously linked with Autism (only NRXN1 replicates)

| Chromosome | Gene | Start (B36 Mb) | End (B36 Mb) | Cases Impacted | Cases Not Impacted | Controls Impacted | Controls Not Impacted | P-value |
|---|---|---|---|---|---|---|---|---|
| 2 | NRXN1 | 50000992 | 51109836 | 8 | 918 | 2 | 1439 | 0.0173 |
| X | NLGN3 | 70281436 | 70307776 | 1 | 925 | 0 | 1440 | 1 |
| 22 | SHANK3 | 49459936 | 49518507 | 1 | 925 | 1 | 1440 | 1 |
| 7 | AUTS2 | 68702255 | 69895790 | 1 | 925 | 0 | 1440 | 0.391 |

TABLE 3

Novel CNVs in Autism: SNP based whole genome CNV association analysis.

| Deletions Significance CNVR | P value (two-tailed) | TDT (Pval) | Cases Del | Control Del | Genes involved or nearby |
|---|---|---|---|---|---|
| chr2: 51120644-51147600 | 0.000353704 | 0.205078 | 10 | 0 | NRXN1 |
| chr3: 1915190-1915922 | 0.000783957 | 0.246094 | 9 | 0 | CNTN4 |
| chr6: 162584576-162587001 | 0.003845664 | 0.273438 | 7 | 0 | PARK2, parkin |
| chr2: 78268199-78311249 | 0.003848162 | 0.164063 | 7 | 0 | BC030125 |
| chr16: 45834321-45887745 | 0.018869244 | N/A | 5 | 0 | ITFG1 |

| Duplications Significance CNVR | P value (two-tailed) | TDT (Pval) | Cases Dupl | Control Dupl | Genes involved or nearby |
|---|---|---|---|---|---|
| chr15: 22393833-22532309 | 3.24E−05 | 0.08728 | 13 | 0 | C15orf2 |
| chr22: 19351264-19358946 | 0.001735832 | N/A | 8 | 0 | BC035867 |
| chr19: 22431189-22431397 | 0.002465764 | N/A | 14 | 0 | ZNF492 |
| chr1: 145658465-145807358 | 0.018819491 | 0.3125 | 5 | 0 | GJA5 |
| chr8: 55021047-55070134 | 0.451753431 | N/A | 5 | 0 | RGS20, TCEA1 |
| chr20: 55426961-55430874° | 0.451893774 | N/A | 3 | 0 | RBM38 |
| chr7: 32667087-32770713° | 1 | N/A | 4 | 0 | AK026768, AK057321, AK127 |
| chr1: 174500555-174543675 | 1 | N/A | 6 | 0 | RFWD2, RP11-318C24.3 |
| chr3: 122826190-122870474° | 1 | N/A | 3 | 0 | FBXO40, GOLGB1, HCLS1 |

TABLE 4

CNVs overrepresented in Autism: SNP based whole genome CNV association analysis

| Deletions Significance CNVR | P value (two-tailed) | TDT (Pval) | Cases Del | Control Del | Genes involved or nearby |
|---|---|---|---|---|---|
| chr8: 43765570-43776595 | 1.36E−11 | 6.41E−08 | 89 | 29 | POTE8 |
| chr3: 4199731-4236304 | 0.001346291 | 0.013885 | 15 | 3 | UNQ3037 |
| chr10: 87941666-87949029 | 0.002478015 | 0.022217 | 14 | 3 | GRID1 |

| Duplications Significance CNVR | P value (two-tailed) | TDT (Pval) | Cases Dupl | Control Dupl | Genes involved or nearby |
|---|---|---|---|---|---|
| chr2: 13119667-13165898 | 4.86E−06 | 0.123485 | 31 | 7 | AK123120 |
| chr12: 31300846-31302088 | 0.005659589 | 0.000211 | 32 | 17 | FAM60A |
| chr6: 69291821-69294028 | 0.006196884 | 0.002947 | 56 | 38 | CR595314 |
| chr3: 2548148-2548531 | 0.007053862 | 0.017578 | 9 | 1 | CNTN4 |
| chr3: 174754378-174771975 | 0.00744663 | 0.012402 | 110 | 92 | NLGN1 |
| chr4: 144847402-144854579 | 0.008863484 | 0.117188 | 10 | 2 | LOC441046 |

TABLE 4-continued

CNVs overrepresented in Autism: SNP based whole genome CNV association analysis

| | | | | | |
|---|---|---|---|---|---|
| chr2: 237486328-237497105 | 0.02604212 | 0.00013 | 17 | 8 | AK056246 |
| chr6: 168091860-168339100 | 0.03197763 | 0.008753 | 77 | 65 | AX747198, FLJ00181, FRM |

TABLE 5

Novel CNVs in Autism: Gene based whole genome CNV association analysis

| Gene Deleted | Chr Position | P-value | Cases Del | Control Del |
|---|---|---|---|---|
| SPANXA1 | chrX: 140505500-140506565 | 0.003156582 | 7 | 0 |
| OSBPL10 | chr3: 31677320-31998242 | 0.03730223 | 4 | 0 |
| KRT3 | chr12: 51469735-51476159 | 0.084915959 | 3 | 0 |
| CRYL1 | chr13: 19875805-19998012 | 0.084915959 | 3 | 0 |
| PLCB1 | chr20: 8061295-8813547 | 0.084915959 | 3 | 0 |
| PKIB | chr6: 122834760-123089217 | 0.084915959 | 3 | 0 |
| FAM11A | chrX: 148486014-148521375 | 0.193249464 | 2 | 0 |
| HSFX1 | chrX: 148484725-148666329 | 0.193249464 | 2 | 0 |
| LOC728269 | chrX: 148471104-148476911 | 0.193249464 | 2 | 0 |
| TMEM185A | chrX: 148486014-148521375 | 0.193249464 | 2 | 0 |

| Gene Duplicated | Chr Position | P-value | Cases Dup | Control Dup |
|---|---|---|---|---|
| SNPRN | chr15: 22652791-22774822 | 0.001385031 | 8 | 0 |
| FLJ36144 | chr15: 21237111-21243483 | 0.003156582 | 7 | 0 |
| BCL9 | chr1: 145479805-145564639 | 0.016381537 | 5 | 0 |
| ACP6 | chr1: 145585791-145609238 | 0.016381537 | 5 | 0 |
| GJA5 | chr1: 145694955-145712108 | 0.016381537 | 5 | 0 |
| BSPRY | chr9: 115151643-115173325 | 0.016381537 | 5 | 0 |
| HDHD3 | chr9: 115175518-115179080 | 0.016381537 | 5 | 0 |
| PRKAB2 | chr1: 145093308-145110753 | 0.03730223 | 4 | 0 |
| CR610404 | chr1: 145110973-145113408 | 0.03730223 | 4 | 0 |
| NR_002305 | chr1: 145116053-145118152 | 0.03730223 | 4 | 0 |
| FMO5 | chr1: 145122507-145163569 | 0.03730223 | 4 | 0 |
| CHD1L | chr1: 145180957-145234067 | 0.03730223 | 4 | 0 |
| LYG2 | chr2: 99225142-99238002 | 0.03730223 | 4 | 0 |

TABLE 6

CNVs overrepresented in Autism: Gene based whole genome CNV association analysis

| Gene Deleted | Chr Position | P-value | Cases Del | Control Del |
|---|---|---|---|---|
| MGAM | chr7: 141342147-141453016 | 4.50E-15 | 431 | 326 |
| CTDSPL | chr3: 37878672-38000964 | 3.97E-06 | 54 | 23 |
| TMLHE | chrX: 154372966-154495791 | 0.002134669 | 14 | 3 |
| AX748173 | chrX: 140418508-140565735 | 0.006704546 | 9 | 1 |
| BC042039 | chrX: 140541661-140542527 | 0.006704546 | 9 | 1 |
| GRID1 | chr10: 87349291-88116230 | 0.006913736 | 14 | 4 |
| ABCC6 | chr16: 16150922-16224838 | 0.007330262 | 10 | 2 |
| SPANXA2 | chrX: 140163261-140500526 | 0.013988147 | 9 | 2 |
| ASTN2 | chr9: 118227327-119217138 | 0.048683151 | 6 | 1 |
| ZNF675 | chr19: 23627547-23661857 | 0.048801793 | 7 | 2 |
| LCE3E | chr1: 150804753-150805872 | 0.083414958 | 14 | 8 |
| LCE3D | chr1: 150818483-150819604 | 0.083414958 | 14 | 8 |
| RDH16 | chr12: 55631485-55638370 | 0.093198702 | 5 | 1 |
| DLGAP1 | chr18: 3488836-3870135 | 0.093198702 | 5 | 1 |
| ZNF681 | chr19: 23717999-23733479 | 0.117101565 | 7 | 3 |
| NRXN1 | chr2: 50000991-51109836 | 0.182798646 | 16 | 12 |
| PSG1-11 | chr19: 47917633-48132066 | 0.552060877 | 113 | 133 |

| Gene Duplicated | Chr Position | P-value | Cases Dup | Control Dup |
|---|---|---|---|---|
| NLGN1 | chr3: 174598937-175483810 | 0.012790041 | 105 | 94 |
| HDHD1A | chrX: 6976960-7076189 | 0.326156915 | 3 | 1 |

TABLE 7

Rare CNVs that are detected in autism patients and not observed in subjects without autism from a Gene based whole genome CNV association analysis

| Gene Deleted | Chr Position | P-value | Cases Del | Control Del |
|---|---|---|---|---|
| C6orf64 | chr6: 39179817-39190843 | 0.016382 | 5 | 0 |
| PNLIPRP1 | chr10: 118340479-118358676 | 0.084916 | 3 | 0 |
| PRIMA1 | chr14: 93254396-93324519 | 0.084916 | 3 | 0 |
| PRKCA | chr17: 61729387-62237324 | 0.084916 | 3 | 0 |
| ZNF528 | chr19: 57592932-57613469 | 0.084916 | 3 | 0 |
| AK058073 | chr19: 57624251-57647380 | 0.084916 | 3 | 0 |
| AB086839 | chr19: 57626472-57634508 | 0.084916 | 3 | 0 |
| ZNF534 | chr19: 57626472-57634508 | 0.084916 | 3 | 0 |
| AB091373 | chr19: 57648570-57653219 | 0.084916 | 3 | 0 |
| AB091374 | chr19: 57648570-57653219 | 0.084916 | 3 | 0 |
| AB091376 | chr19: 57648677-57653219 | 0.084916 | 3 | 0 |
| DBH | chr9: 135491305-135514287 | 0.193249 | 2 | 0 |
| NF2 | chr22: 28329564-28424585 | 0.193249 | 2 | 0 |

| Gene Duplicated | Chr Position | P-value | Cases Dup | Control Dup |
|---|---|---|---|---|
| SH3PXD2A | chr10: 105343773-105605154 | 0.037302 | 4 | 0 |
| LGR5 | chr12: 70120079-70266353 | 0.084916 | 3 | 0 |
| KIAA1864 | chr16: 69511994-69565424 | 0.084916 | 3 | 0 |
| FLJ22167 | chr16: 74129515-74147671 | 0.084916 | 3 | 0 |
| COTL1 | chr16: 83156704-83209170 | 0.084916 | 3 | 0 |
| AK127352 | chr16: 83156708-83168203 | 0.084916 | 3 | 0 |
| MYO1D | chr17: 27843740-28228015 | 0.084916 | 3 | 0 |
| HEATR5B | chr2: 37061656-37164989 | 0.084916 | 3 | 0 |
| AK091889 | chr4: 13265900-13541950 | 0.084916 | 3 | 0 |
| COX18 | chr4: 74139279-74154336 | 0.084916 | 3 | 0 |
| COX18HS | chr4: 74139279-74154336 | 0.084916 | 3 | 0 |
| ANKRD17 | chr4: 74159365-74343366 | 0.084916 | 3 | 0 |
| xl1 | chr5: 118434798-118497772 | 0.084916 | 3 | 0 |
| DMXL1 | chr5: 118435083-118612721 | 0.084916 | 3 | 0 |
| TNFAIP8 | chr5: 118632316-118758193 | 0.084916 | 3 | 0 |
| RSPO3 | chr6: 127481740-127560603 | 0.084916 | 3 | 0 |
| AJ606314 | chr6: 135860636-136078886 | 0.084916 | 3 | 0 |
| AJ606325 | chr6: 135860636-136078886 | 0.084916 | 3 | 0 |
| KIAA1023 | chr7: 2616423-2620886 | 0.084916 | 3 | 0 |
| KIAA0716 | chr7: 111290174-111633698 | 0.193249 | 2 | 0 |

References for Example I

1. Chakrabarti, S. & Fombonne, E. Pervasive developmental disorders in preschool children. *Journal of the American Medical Association* 285, 3093-3099 (2001).
2. Chakrabarti, S. & Fombonne, E. Pervasive developmental disorders in preschool children: confirmation of high prevalence. *Am J Psychiatry* 162, 1133-41 (2005).
3. Jones, M. B. & Szatmari, P. Stoppage rules and genetic studies of autism. *J Autism Dev Disord* 18, 31-40 (1988).
4. Ritvo, E. R. et al. The UCLA-University of Utah epidemiologic survey of autism: prevalence. *Am J Psychiatry* 146, 194-9 (1989).
5. Bailey, A. et al. Autism as a strongly genetic disorder: evidence from a British twin study. *Psychol Med* 25, 63-77 (1995).
6. Klauck, S. M. Genetics of autism spectrum disorder. *Eur J Hum Genet* 14, 714-20 (2006).
7. Vorstman, J. A. et al. Identification of novel autism candidate regions through analysis of reported cytogenetic abnormalities associated with autism. *Mol Psychiatry* 11, 1, 18-28 (2006).
8. Sebat, J. et al. Strong association of de novo copy number mutations with autism. *Science* 316, 445-9 (2007).
9. Gunderson, K. L., Steemers, F. J., Lee, G., Mendoza, L. G. & Chee, M. S. A genome-wide scalable SNP genotyping assay using microarray technology. *Nat Genet* 37, 549-54 (2005).
10. Steemers, F. J. et al. Whole-genome genotyping with the single-base extension assay. *Nat Methods* 3, 31-3 (2006).
11. Hakonarson, H. et al. A genome-wide association study identifies KIAA0350 as a type 1 diabetes gene. *Nature* 448, 591-594 (2007).

Example II

Common Genetic Variation in the Intergenic Region Between CDH10 and CDH9 is Associated with Susceptibility to Autism Spectrum Disorders Epidemiologic studies have convincingly implicated genetic factors in the pathogenesis of autism, a common neuropsychiatric disorder in children, which presents with variable phenotype expression that extends into adulthood. Several genetic determinants have already been reported, including de novo copy number variations (CNVs) that may account for a small subset of autism spectrum disorder (ASD). Implicated genomic regions appear to be highly heterogeneous with variations reported in several genes, including NRXN1, NLGN3, SHANK3 and AUTS2. See Example I.

The following materials and methods are provided to facilitate the practice of Example II.

Autism Genetic Resource Exchange (AGRE)

The Autism Genetic Resource Exchange (AGRE; on the world wide web at agre.org) has a collection of DNA samples and clinical information from families with autism spectrum disorders (ASDs) (1). We have genotyped DNA samples from 943 families (4,444 individuals) from the AGRE collection (as of August 2007). These AGRE families include 917 multiplex families, 24 simplex families and 2 families without ASD diagnosis (not used in analysis).

The AGRE annotation database classifies three diagnostic categories based on the Autism Diagnostic Interview-Revised (ADI-R) (2): autism, broad spectrum (patterns of impairment along the spectrum of pervasive developmental disorders, including PDD-NOS and Asperger's syndrome) or Not Quite Autism (individuals who are no more than one point away from meeting autism criteria on any or all of the social, communication, and/or behavior domains and meet criteria for "age of onset"; or, individuals who meet criteria on all domains, but do not meet criteria for the "age of onset"). In our analysis, AGRE patients with "Autism" (n=1,684), "Broad Spectrum" (n=171) or "Not Quite Autism" (n=79) phenotype annotation were treated as a single ASD group. Among them, 11 subjects had autism diagnoses assigned by ADOS (Autism Diagnostic Observation Schedule) (3) without ADI-R (Autism Diagnostic Interview-Revised).

The age of onset and age of assessment for ASD subjects with different diagnostic categories were given in detail below. The Ravens estimated non-verbal IQ scores are available for a subset of AGRE individuals: the median score is 100 in multiplex families (708 ASD subjects) and 98 in simplex families (49 ASD subjects). 387 ASD subjects in multiplex families and 28 ASD subjects in simplex families cannot be tested on the Ravens (annotated as "Ravens-untestable" in AGRE annotation database) due to either low functioning or behavior.

other ancestry from the association test (see detailed QC procedure below).

| AGRE self-identified ancestry | Number of subjects |
|---|---|
| American Indian/Alaskan Native | 10 |
| Asian | 103 |
| Black or African American | 99 |
| More Than One Race | 262 |
| Native Hawaiian or other Pacific Islander | 28 |
| Unknown | 448 |
| White | 3,494 |

ASD and Control Subjects in (Autism Case-Control) ACC Cohort

The ASD subjects within the ACC cohort were provided by researchers from multiple collaborative projects across the US, as well as CHOP where all samples were genotyped. All ASD subjects utilized for the case-control analysis were diagnosed with the ADOS (Autism Diagnostic Observation Schedule), ADI (Autism Diagnostic Interview) or ADI-R (Autism Diagnostic Interview-Revised) diagnostic tools. The "Best Diagnosis" provided by collaborators are used to select ASD subjects for genotyping, which is a composite measure based on both ADI and ADOS. After excluding subjects who have not been genotyped, subjects without genotype data in the database (due to chip failure), subjects without phenotype annotation, and subjects with missing

|  | Number of individuals |  | Median | Mean | SD | Range |  |
|---|---|---|---|---|---|---|---|
| Multiplex |  |  |  |  |  |  |  |
| Autism | 1358 | Age of Onset | 1.25 | 1.25 | 0.68 | <1-5 | years |
|  |  | Age of Assessment | 7.12 | 8.11 | 4.68 | 2-46 | years |
| NQA | 68 | Age of Onset | 1.5 | 1.82 | 1.15 | <1-6 | years |
|  |  | Age of Assessment | 5.44 | 6.84 | 4.35 | 2-24 | years |
| BroadSpectrum | 136 | Age of Onset | 1.5 | 1.73 | 1.02 | <1-5 | years |
|  |  | Age of Assessment | 6.19 | 8.18 | 6.25 | 2-44 | years |
|  |  |  |  |  |  | 2-44 | years |
| Ravens estimated non-verbal IQ | 708 |  | 100 | 100 | 18 | 38-143 |  |
| Simplex |  |  |  |  |  |  |  |
| Autism | 105 | Age of Onset | 1.5 | 1.36 | 0.72 | <1-3.5 | years |
|  |  | Age of Assessment | 9.98 | 9.57 | 4.52 | 3-30 | years |
| NQA | 3 | Age of Onset | 2 | 1.6 | 0.57 | 1-2 | years |
|  |  | Age of Assessment | 7.49 | 9.94 | 5.78 | 5-16 | years |
| BroadSpectrum | 13 | Age of Onset | 1.5 | 1.92 | 1.25 | <1-5 | years |
|  |  | Age of Assessment | 6.88 | 10.4 | 9.38 | 3-31 | years |
| Ravens estimated non-verbal IQ | 49 |  | 98 | 96 | 22 | 38-134 |  |

The self-identified race/ethnicity information for these AGRE individuals is listed below. However, in our association analysis, we used multi-dimensional scaling on genotype data and applied stringent criteria to identify all subjects with European ancestry, and we excluded subjects of diagnosis data (when "Best diagnosis" is set as "MISSING"), we were left with 1,453 samples that met the study criteria of either positive ADI/ADI-R, ADOS or both.

The average age of the study subjects was 10.3±6.6 years, and the average age for ADI diagnosis was 8.4±4.7 years, the average age for ADOS diagnosis was 9.9±7.2 years, and the average age of IQ test is 10.9±6.7 years. Only 1,241 subjects of European ancestry were used in the study (see QC section below). The majority (83.1%) of subjects were males. Almost all (94.5%) DNA samples were extracted from whole blood, while others were from cell lines.

| Level | NVIQ | | | | VIQ | | | |
|---|---|---|---|---|---|---|---|---|
| | Number | Median | Mean | SD | Number | Median | Mean | SD |
| Autism/AUT | 572 | 89 | 85 | 27.7 | 562 | 72 | 75 | 29.8 |
| ASD/PDD-NOS/Asperger | 29 | 100 | 98 | 18.8 | 36 | 106 | 105 | 24.8 |

The control group used in the discovery phase included 7,077 children of self-reported Caucasian ancestry (average age was 8.8±5.4 SD years; 52.08% males, 47.65% females and 0.27% unknown). All control subjects had no history of ASDs, and had not demonstrated symptoms to be referred to diagnostic testing. The CHOP controls were recruited by CHOP nursing and medical assistant staff under the direction of CHOP clinicians within the CHOP Health Care Network, including four primary care clinics and several group practices and outpatient practices that included well child visits. All DNA samples were extracted from whole blood. Although these control subjects were all self-identified Caucasians, we combined these subjects with cases and used multi-dimensional scaling to infer a homogeneous group of subjects of European ancestry during our quality control procedure (see QC section below).

Genotyping Platform for Discovery Cohorts

Individuals in the AGRE cohort and the ACC cohort were genotyped utilizing the Illumina HumanHap550 SNP genotyping array, which contains more than 550,000 tag SNPs, selected on the basis of HapMap Phase I and Phase II data to capture the haplotype diversity across the human genome. Among the several cohorts used in our study, the samples from AGRE were genotyped using DNA extracted from Epstein-Barr Virus (EBV)-transformed lymphoblastoid cell lines, while almost all subjects in the other cohorts (both ASD cases and control subjects) were genotyped using DNA extracted from whole blood.

The genotyping experiments for AGRE families and the ACC subjects were performed at the Center for Applied Genomics, Children's Hospital of Philadelphia. Most of the AGRE samples (n=4,163) were genotyped on the Illumina HumanHap550 version 3 arrays, but a small subset of AGRE samples (n=291) were genotyped by the version 1 arrays. The only difference between version 1 and version 3 arrays is the replacement of ~10K SNP markers in the new version of arrays by Illumina.

Quality Control (QC) Overview for AGRE Data Set

Figure 9:
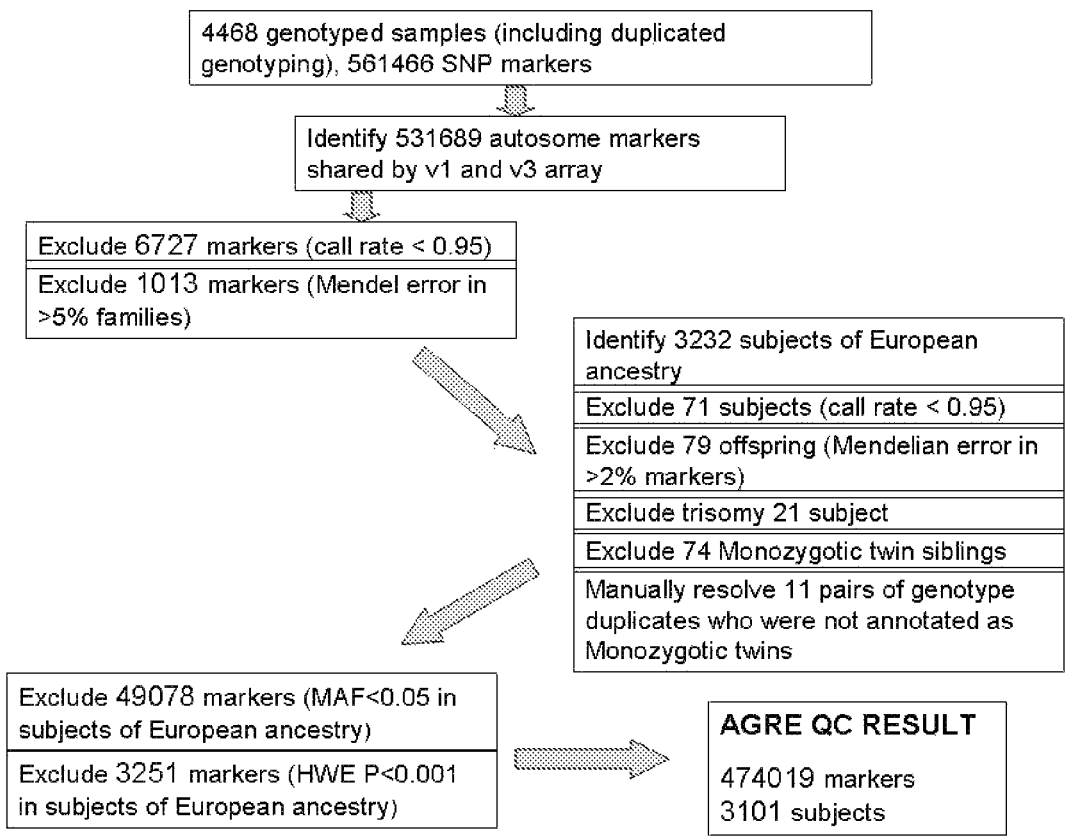
FIG. 9. An overview of the quality control (QC) procedure for the AGRE data set (autosomal markers).

An overview of the quality control (QC) procedure for the AGRE data set (autosomal markers) is given in FIG. 9. More detailed QC procedure is described in FIG. 9.

Since the PDT software cannot be used on sex chromosomes, we have applied X-APL on chromosome X markers in a separate analysis, and the QC procedure is described in section.

Quality Control for the Selection of Subjects in Association Analysis in the AGRE Cohort Stringent quality control (QC) measure was applied on the genotyped AGRE subjects for subsequent association analysis. The various aspects of QC were described in detail below:

Low Genotype Call Rate

The call rate is calculated based on the number of "No Call" genotypes with default genotyping calling algorithm as implemented in the Illumina BeadStudio software. The call rate per individual was assessed by the PLINK software (4). A total 24 samples have been genotyped twice due to the low call rate in the first batch of genotyping. Altogether, 47 unique individuals in AGRE data set were excluded from analysis due to low call rate.

Mendelian Error

Due to the availability of family data, we were able to check the familial relationships between the AGRE samples with known pedigree information. Samples with excessive Mendelian errors could indicate potential paternity problems, sample mislabeling, or sample handling problem during the genotyping experiments, and should be excluded from downstream association analysis.

This analysis was performed with respect to offspring, that is, whenever a Mendelian error is present, the offspring gets a count of Mendelian error, while the parents do not get such a count. When one offspring in a large nuclear family has Mendelian problems (for example, due to sample mislabeling for this individual), this procedure ensures that only this offspring is excluded, while other offspring and the parents are still kept in the analysis. The Mendelian error rate per individual was assessed by the PLINK software (4). A total of 79 samples (as offspring) are identified who had >2% markers with Mendelian inconsistency with respect to parental genotype data, and were excluded from our association test.

Monozygotic Twins

In the AGRE collection, 70 families contain MonoZygotic (MZ) twins, including those with triplets and quartets siblings. We have removed 74 individuals from the analysis, such that only one MZ twin sibling in each family is kept in the analysis.

Genotype Duplicates Who were not Annotated as Monozygotic Twins

We next checked genotype duplicates, that is, two subjects with almost identical genotypes, who were not annotated as monozygotic twins in the AGRE annotation, some of whom were even present in two different families. As expected, when two duplicates were present in two different families, they can be readily detected by Mendelian inconsistency and usually we can infer which sample is being mislabeled into the wrong family. The complete list of duplicated individuals who were not annotated as MZ twins is given below, and these issues were manually examined and resolved.

| individual 1 | individual 2 | Notes |
|---|---|---|
| AU026402 | AU013801 | AU013801 is singleton and not used in any analysis |
| AU001201 | AU000803 | Mendelian error for AU000803, excluded from analysis |

-continued

| individual 1 | individual 2 | Notes |
|---|---|---|
| AU043603 | AU033402 | Mendelian error for AU043603, excluded from analysis |
| AU1242302 | AU1214302 | Mendelian error for AU1214302, excluded from analysis |
| AU1364302 | AU1378304 | Mendelian error for AU1364302 and excluded from analysis; AU137804 excluded from analysis |
| AU1644304 | AU1655201 | AU1655201 is parent and this family has no children passing QC |
| AU1070301 | AU1008201 | AU1008201 is parent and this family has no children passing QC |
| AU1953302 | AU1953303 | Both individuals were excluded from analysis |
| AU1791301 | AU1791302 | family AU1791 excluded from analysis |
| AU1833302 | AU1833303 | This pair of MZ twin is NOT annotated in the AGRE phenotype database; AU1833303 is manually excluded from analysis |
| AU037803 | AU035502 | Mendelian error for AU037803, excluded from analysis; AU035502 is singleton and not used in |

Chromosome 21 Trisomy

Using the PennCNV algorithm (5), we have identified three subjects with chromosome 21 trisomy, including AU075307, AU1227303 and AU015804. The individual AU015804 was annotated as "non-idiopathic autism" in the AGRE phenotype database, and was excluded from our association analysis.

Inferring Individuals of European Ancestry

Although family-based study design protects against population stratification, it may lead to allelic heterogeneity and mask truly associated signals. We have decided to only examine individuals of European ancestry for association signals in all our discovery cohorts and replication cohorts.

We used Multi-Dimensional Scaling (MDS), as implemented in the PLINK software (Purell et al., supra), for inferring population structure in the AGRE data set. Comparing self-identified ancestry with the MDS-inferred ancestry confirmed the reliability of MDS to identify genetically inferred individuals of European ancestry. These individuals are clustered towards the right side of the triangle, as defined by that Principle component 1 is more than −10, and that Principle component 2 is between −2 and 2 (data not shown). A total of 3232 individuals were inferred as having European ancestry using the above procedure.

Final Counts of Subjects Passing QC

Applying the QC measures mentioned in all the previous sections, we were left with 3101 individuals for association analysis.

Quality Control for Selection of SNPs in Association Analysis

Overlap of the HumanHap550 v1 and v3 Arrays

Since a small portion of the individuals in the AGRE cohort are genotyped by the HumanHap550 v1 array (n=291) while others are genotyped by the v3 array, our analysis only concerns on the markers shared by the v1 and v3 array: The HumanHap550 v1 array contains 555352 markers while the v3 array contains 561466 markers, including 545080 markers that are shared by the two arrays.

Mitochondria and Sex Chromosome Markers

We have excluded markers from X, Y, XY and Mitochondria chromosomes to restrict our association analysis to autosome markers. This left us with 531689 markers from the above step.

NoCall Rate Per Marker

Markers with call rate less than 95% were excluded from analysis. The call rates were calculated by the PLINK software. A total of 6727 markers were excluded from association analysis in this step.

Mendelian Error

Markers with excessive Mendelian error (in >5% families) were excluded from analysis, since they may indicate genotyping failure, SNP clustering failure or the presence of SNPs within common copy number variation regions. Based on per-individual Mendelian error rate calculated by the PLINK software, a total of 492 markers does not meet this threshold and should be excluded.

Minor Allele Frequency (Individuals of European Ancestry)

Markers with Minor Allele Frequency (MAF) less than 5% were excluded from our analysis. This procedure is restricted on AGRE individuals passing QC and used in our association analysis, and the MAF are calculated by the PLINK software on the founders (parents) of the AGRE collection. A total of 49078 markers were excluded from association analysis in this step.

Hardy-Weinberg Equilibrium (Individuals of European Ancestry)

Markers with Hardy-Weinberg Equilibrium P-value less than 0.001 excluded from analysis, since these markers may have genotyping failure, or are located in common CNV regions. This procedure is restricted on AGRE individuals passing QC and used in our association analysis, and the MAF are calculated by the PLINK software on the founders (parents) of the AGRE collection. A total of 3251 markers were excluded from association analysis in this step.

Final Counts of SNPs Passing QC

After the above QC procedure for selection of SNPs, a total of 474019 SNPs were used in subsequent association analysis. The genome-wide significance P-value threshold (based on Bonferroni adjustment) was calculated as $1.1 \times 10^{-7}$.

Quality Control for the ACC Cohort

The quality control procedure for the ACC cohort is largely similar to those performed on the AGRE cohort. Here we describe several different aspects of QC that were applied on the ACC cohort.

Population Stratification

We applied the PLINK software for generation of genome-wide IBS estimates between all subjects (including both cases and controls), and then generated multi-dimensional scaling (MDS) plots for visual examination of population outliers. To help "boost" the signal of the population genetic analysis, we have included 112 HapMap individuals (labeled as CEU, CHB, JPT, YRI below) into the MDS analysis. The individuals of European ancestry are selected by the Principle component 1 of more than −0.01 and Principle component 2 of less than 0.03 (data not shown).

The quality of the data for ACC cohort was screened by a series of routine analyses. Individual SNPs were excluded from further analysis if they deviated from Hardy-Weinberg equilibrium with a P-value of less than 0.001, an individual SNP genotype yield of less than 95%, or a minor allele frequency of less than 5%. In addition, subjects were also removed if their genotype yield is less than 95% (excluding 26 subjects). These procedures were identical as those applied in the AGRE data set.

To further address the concerns on population stratification, we have also applied EigenStrat software (A. L. Price et al., *Nat Genet* 38, 904 (2006) to re-perform all association tests on the case and control subjects passing the QC threshold above. The P-values for the SNPs reported in Table 9 are all within 10-fold differences, further implicating the effectiveness of MDS approach in removing population outliers. Therefore, we followed previously published GWAS studies, and report the unadjusted P-values.

Detection and Elimination of Cryptic Relatedness and Duplicated Genotyping

We have calculated genome-wide IBS estimates for all pairwise comparisons among all case subjects and control subjects. To detect cryptic relatedness and potential duplicated genotyping within our data sets, we have applied a two-step procedure to calculate pairwise IBD estimates between all individuals. First, we examined MDS and only keep in our data sets those individuals of inferred European ancestry, with call rates greater than 95%; second, we re-calculate genome-wide IBS estimates and re-calculate the IBD estimates using the PLINK software. This two-step procedure ensures that allele frequency differences between populations do not lead to biases in IBD estimations. We applied a stringent threshold for detecting cryptic relatedness: any pairs of subjects with IBD>0.15 were processed such that only one of the subjects remained in the final association test.

Final Counts of Subjects Passing QC

These QC procedure resulted in the use of 1,204 cases, 6,491 controls and 480,530 SNPs in the subsequent association analysis.

Association Test

Pedigree Disequilibrium Test (PDT)

The association analysis for the AGRE cohort is performed by the PDT software version 6, which implements the Pedigree Disequilibrium Test (E. R. Martin, S. A. Monks, L. L. Warren, N. L. Kaplan, *Am J Hum Genet* 67, 146 (2000); E. R. Martin, M. P. Bass, N. L. Kaplan, *Am J Hum Genet* 68, 1065 (2001). Custom scripts were used to convert the standard genotype data into formats that can be read by the PDT software, to zero out Mendelian errors (since PDT was unable to handle Mendelian errors correctly), and to pad parental genotype data as missing data for parents whose genotype information were not available. All default parameters were used in the association analysis. The PDT needs either: (1) both parents genotypes and one or more affected offspring, or (2) a discordant (one affected, one unaffected) sibpair. Other families were not used in the analysis. The test statistic is given as Z-score, and the P-value is calculated based on the Z-score.

Family-Based Association Test (FBAT)

To cross-check the association results calculated by the PDT software, we have also applied a different algorithm as implemented in the FBAT (Family-based association test) software (S. Horvath, X. Xu, N. M. Laird, *Eur J Hum Genet* 9, 301 (2001). Similar to PDT, the FBAT software can use both nuclear family information and discordant sibpair information in the association test. We have adopted all default parameters in the FBAT software (FBAT automatically zero out Mendelian errors detected in families), with additive model, bi-allelic test.

FBAT Assuming Linkage

We also tested a different FBAT model, by taking into account of potential linkage, when testing for association. These results are largely concordant with those generated by default parameters.

Results

We did not observe genome-wide significant association ($P<5\times10^{-8}$) to ASDs in the AGRE cohort, but we hypothesized that meaningful associations were contained within the lowest P-values. To boost power for identifying these associations, we examined a second cohort (Autism Case-Control cohort, or ACC cohort), comprising 1,453 subjects with ASDs from multiple US sites and 7,070 control subjects without ASDs from the Children's Hospital of Philadelphia, who were also genotyped on the same platform. The subjects with ASDs in this cohort were diagnosed using the ADI and ADOS tools. After conducting thorough quality control measures on the genotypes, association analyses were conducted on 1,241 subjects with ASDs and 6,491 control subjects of inferred European ancestry (Supplementary Methods). We did not detect ome-wide significant association ($P<5\times10^{-8}$) to ASDs in the ACC cohort either. Therefore, we subsequently performed a combined analysis of these two independent data sets using recommended meta-analysis approaches[21]. Examining autosomes and the X chromosome, one SNP located on 5p14.1 reached genome-wide significance (rs4307059, $P=3.4\times10^{-8}$), and five additional SNPs at the same locus had P-values below $1\times10^{-4}$ (Table 8 and FIG. 1A). We additionally analyzed 10 markers on the Y chromosome in the ACC cohort, with the most significant SNP being rs2032597 ($P=1.1\times10^{-4}$) located within USP9Y (ubiquitin specific protease 9, Y-linked). See Table 9. Furthermore, we have analyzed 15 markers in pseudoautosomal regions of sex chromosomes in the two discovery cohorts, but no markers showed evidence of association. See Table 10.

To identify additional variants that associate with ASDs but were not captured by the SNP genotyping array, we analyzed the discovery cohorts using whole-genome imputed genotypes on autosomes (see Supplementary Methods). The most significant association signals were still those in the 5p14.1 region (Table 11 and FIG. 1B, 1C); however, several additional genomic loci, such as 6p11.2 (within LRRC1), 13q33.3 (near MYO16) and 14q21.1 (near FBXO33), harbor SNPs with suggestive association signals (Table 12).

To replicate our genome-wide association results at the 5p14.1 locus, we examined the association statistics for these markers in a third independently generated and analyzed cohort, including 1,537 subjects from 487 autism families genotyped with ~1 million markers on the Illumina HumanHap1M BeadChip (CAP cohort, Table 8). The association signals for all the aforementioned SNPs were replicated in this cohort (P-values ranging from 0.01 to $2.8\times10^{-5}$). To seek additional evidence of replication, we examined association statistics from a fourth independent cohort of 108 ASD cases and 540 genetically matched control subjects, genotyped on the HumanCNV370 array, a SNP genotyping array supplemented by non-polymorphic markers for copy number analysis (CART cohort, Table 8). Since rs7704909 and rs10038113 were not present in this array platform, we analyzed association on imputed genotypes. Both genotyped and imputed SNPs were replicated in the expected direction in the CART cohort (Table 8). Meta-analysis on all four data sets implicates that all six SNPs are associated with ASDs, with combined P-values ranging from $7.9\times10^{-8}$ to $2.1\times10^{-10}$. Taken together, multiple sources of converging evidence firmly established that common genetic variants on 5p14.1 confer susceptibility to ASDs.

TABLE 8

A list of the most significantly associated SNPs (P < 1 × 10⁻⁴ in the discovery phase) between CDH10 and CDH9 on 5p14.1.

| | | | | | Discovery cohorts | | | | | | Replication cohorts | | All |
|---|---|---|---|---|---|---|---|---|---|---|---|---|---|
| | | | | | | | ACC | | | | | | |
| Genotyped SNPs | Position[1] | Minor/major allele[1] | AGRE MAF[2] | AGRE P-value (PDT) | AGRE Z-score[3] | ACC case MAF | ACC control MAF | ACC P-value (allelic) | ACC odds ratio[4] | Discovery meta P-value | CAP P-value[5] (PDT) | CART P-value[5] (allelic) | cohorts combined P-value |
| rs4307059 | 26003460 | C/T | 0.38 | $1.1 \times 10^{-5}$ | 4.40 | 0.35 | 0.39 | $2.2 \times 10^{-4}$ | 1.19 | $3.4 \times 10^{-8}$ | $1.2 \times 10^{-2}$ | $1.6 \times 10^{-2}$ | $2.1 \times 10^{-10}$ |
| rs7704909 | 25934678 | C/T | 0.39 | $1.6 \times 10^{-5}$ | 4.31 | 0.36 | 0.40 | $6.2 \times 10^{-4}$ | 1.17 | $1.4 \times 10^{-7}$ | $9.1 \times 10^{-3}$ | $5.2 \times 10^{-2}$ | $1.1 \times 10^{-9}$ |
| rs12518194 | 25987318 | G/A | 0.39 | $1.3 \times 10^{-5}$ | 4.36 | 0.36 | 0.39 | $1.0 \times 10^{-3}$ | 1.16 | $2.0 \times 10^{-7}$ | $9.3 \times 10^{-3}$ | $1.8 \times 10^{-2}$ | $1.1 \times 10^{-9}$ |
| rs4327572 | 26008578 | T/C | 0.39 | $2.2 \times 10^{-5}$ | 4.24 | 0.36 | 0.39 | $2.0 \times 10^{-3}$ | 1.15 | $6.2 \times 10^{-7}$ | $7.3 \times 10^{-3}$ | $1.5 \times 10^{-2}$ | $2.7 \times 10^{-9}$ |
| rs1896731 | 25934777 | C/T | 0.34 | $1.7 \times 10^{-3}$ | −3.14 | 0.38 | 0.34 | $1.7 \times 10^{-3}$ | 0.87 | $1.7 \times 10^{-5}$ | $7.7 \times 10^{-5}$ | $9.9 \times 10^{-1}$ | $4.8 \times 10^{-8}$ |
| rs10038113 | 25938099 | C/T | 0.40 | $1.4 \times 10^{-3}$ | −3.19 | 0.43 | 0.39 | $2.4 \times 10^{-3}$ | 0.87 | $2.1 \times 10^{-5}$ | $2.8 \times 10^{-5}$ | $4.1 \times 10^{-1}$ | $7.9 \times 10^{-8}$ |

[1]The chromosome coordinates and allele designation are based on the forward strand of the NCBI 36 genome assembly.
[2]The minor allele frequencies (MAF) are calculated based on AGRE parents of European ancestry.
[3]The Z-score from PDT indicates the direction of association: positive value indicates over-transmission of major allele.
[4]The odds ratio is calculated as major allele over minor allele.
[5]Replication cohorts demonstrated associations in the same direction as the discovery cohorts.

TABLE 9

Association analysis on 10 markers in chromosome Y in the ACC cohort. The association analysis was performed on 989 subjects with ASDs and 3391 control subjects, all of whom were male subjects. The allele frequency and odds ratio were calculated with respect to A1 (allele 1).

| SNP | Position | Missing rate | A1 | Freq_A1 in cases | Freq_A1 in controls | A2 | CHISQ | P | Odds Ratio |
|---|---|---|---|---|---|---|---|---|---|
| rs2058276 | 2728456 | 0.00411 | A | 0.4823 | 0.4889 | G | 0.1324 | 0.7159 | 0.974 |
| rs1865680 | 6928118 | 0.003881 | G | 0.414 | 0.4237 | A | 0.2971 | 0.5857 | 0.9608 |
| rs2032597 | 13357186 | 0.003653 | C | 0.2053 | 0.1532 | A | 15.05 | 0.000105 | 1.428 |
| rs2032590 | 13529007 | 0.002968 | G | 0.001011 | 0.000592 | T | 0.1957 | 0.6582 | 1.709 |
| rs2032624 | 13535818 | 0.02557 | A | 0.3962 | 0.4167 | C | 1.284 | 0.2572 | 0.9186 |
| rs3848982 | 20176596 | 0.00411 | A | 0.06079 | 0.08148 | G | 4.611 | 0.03176 | 0.7296 |
| rs2032612 | 20325879 | 0.007991 | T | 0 | 0 | C | NA | NA | NA |
| rs2032621 | 20332126 | 0.003881 | C | 0 | 0 | T | NA | NA | NA |
| rs2032617 | 20355649 | 0.006164 | T | 0 | 0.000892 | G | 0.8814 | 0.3478 | 0 |
| rs2032652 | 20376701 | 0.003653 | C | 0.06275 | 0.08235 | T | 4.084 | 0.04329 | 0.7461 |

TABLE 10

Association analysis on 15 markers in pseudoautosomal regions in the discovery cohorts. These markers were analyzed in the same procedure as autosome markers. The allele frequency, OR (Odds Ratio) and the Z-score were calculated with respect to A1 (allele 1).

| SNP | HWE P-value (ACC control) | Missing rate (ACC) | A1 | A2 | A1_Freq (ACC cases) | A1_Freq (ACC controls) | P (ACC) | OR (ACC) | Missing rate (AGRE) |
|---|---|---|---|---|---|---|---|---|---|
| rs4933045 | 0.5043 | 0.03042 | A | G | 0.318 | 0.3172 | 0.9381 | 1.004 | 0.02773 |
| rs2738388 | 0.8302 | 0.00039 | T | G | 0.2107 | 0.2237 | 0.1589 | 0.9264 | 0.000645 |
| rs17792825 | 0.0681 | 0.00195 | A | G | 0.1539 | 0.1681 | 0.08583 | 0.9001 | 0.001935 |
| rs17719702 | 0.435 | 0.00221 | C | T | 0.3364 | 0.3352 | 0.9074 | 1.005 | 0.003225 |
| rs17148878 | 0.6602 | 0.05148 | T | C | 0.1453 | 0.1551 | 0.2244 | 0.9262 | 0.01999 |
| rs17148876 | 0.8627 | 0.0007799 | T | C | 0.1155 | 0.1227 | 0.3216 | 0.9337 | 0.00129 |
| rs5989732 | 0.03712 | 0.01287 | T | G | 0.135 | 0.1267 | 0.2739 | 1.075 | 0.0129 |
| rs5949188 | 0.3094 | 0.008189 | C | A | 0.261 | 0.2813 | 0.04228 | 0.9021 | 0.01129 |
| rs17842869 | 0.5463 | 0.0006499 | T | C | 0.1615 | 0.159 | 0.755 | 1.019 | 0.000967 |
| rs17842890 | 0.2685 | 0.0009099 | G | A | 0.03078 | 0.03526 | 0.2695 | 0.8689 | 0.000645 |
| rs17842893 | 0.2733 | 0.00026 | A | G | 0.03117 | 0.0354 | 0.2984 | 0.8767 | 0 |
| rs17653586 | 0.5903 | 0.00104 | T | G | 0.1635 | 0.1488 | 0.06548 | 1.118 | 0.00129 |
| rs1764581 | 0.1797 | 0.007409 | T | C | 0.4381 | 0.4377 | 0.9711 | 1.002 | 0.009029 |

TABLE 10-continued

Association analysis on 15 markers in pseudoautosomal regions in the discovery cohorts.
These markers were analyzed in the same procedure as autosome markers. The allele
frequency, OR (Odds Ratio) and the Z-score were calculated with respect to A1 (allele 1).

| rs6567787 | 0.6497 | 0.00221 | T | C | 0.2182 | 0.2072 | 0.2236 | 1.068 | 0.002257 |
| rs5983854 | 0.4633 | 0.00221 | C | A | 0.4525 | 0.4338 | 0.09087 | 1.079 | 0.003547 |

| SNP | HWE P-value (AGRE parents) | A1_Freq (AGRE parents) | P (AGRE) | Z (AGRE) | P (combined) |
|---|---|---|---|---|---|
| rs4933045 | 0.5646 | 0.3074 | 0.201089323 | 1.27845418 | 0.371141653 |
| rs2738388 | 0.3598 | 0.2342 | 0.853091955 | −0.18517482 | 0.260141926 |
| rs17792825 | 0.7545 | 0.1637 | 0.555132985 | −0.59008598 | 0.106951616 |
| rs17719702 | 1 | 0.3541 | 0.853846729 | 0.18421252 | 0.838470318 |
| rs17148878 | 0.7444 | 0.1585 | 0.4995597 | −0.67518264 | 0.190433959 |
| rs17148876 | 0.5791 | 0.1218 | 0.431525767 | 0.78658342 | 0.848849149 |
| rs5989732 | 0.2492 | 0.1486 | 1 | 0 | 0.435349662 |
| rs5949188 | 0.2286 | 0.2538 | 0.068227172 | 1.82350349 | 0.80158916 |
| rs17842869 | 0.6858 | 0.158 | 0.425153911 | 0.79751164 | 0.455788835 |
| rs17842890 | 0.2841 | 0.03504 | 0.269744635 | 1.10365081 | 0.94979848 |
| rs17842893 | 0.2947 | 0.03443 | 0.24668026 | 1.15845048 | 0.98492247 |
| rs17653586 | 0.8329 | 0.1336 | 0.937863886 | 0.07795496 | 0.172410243 |
| rs1764581 | 0.2102 | 0.4524 | 0.478890479 | −0.70808822 | 0.660776577 |
| rs6567787 | 0.3285 | 0.2105 | 0.980999172 | −0.02381628 | 0.394180792 |
| rs5983854 | 0.3929 | 0.4168 | 0.12688452 | −1.52650344 | 0.83847888 |

TABLE 11

Imputation-driven meta-analysis on four cohorts identifies additional SNPs with $P < 1 \times 10^{-4}$
on the 5p14.1 region. A1 and A2 refer to allele 1 and allele 2, respectively, and Z-scores
reflect the direction of association for the A1 allele.

| SNP | Position | A1 | A2 | P (AGRE) | Z (AGRE) | P (ACC) | Z (ACC) | P (CAP) | Z (CAP) | P (cart) | Z (cart) | P (combined) |
|---|---|---|---|---|---|---|---|---|---|---|---|---|
| (a) Imputed SNPs ||||||||||||||
| rs12521681 | 25818156 | A | G | 7.69E−03 | −2.67 | 4.07E−02 | −2.05 | 2.85E−02 | −2.19 | 3.06E−01 | −1.02 | 8.54E−05 |
| rs443439 | 25833145 | A | G | 3.00E−02 | −2.17 | 2.65E−02 | −2.22 | 7.85E−03 | −2.66 | 2.59E−01 | −1.13 | 7.54E−05 |
| rs437316 | 25833210 | A | G | 3.00E−02 | −2.17 | 2.60E−02 | −2.23 | 7.85E−03 | −2.66 | 2.59E−01 | −1.13 | 7.41E−05 |
| rs374014 | 25834849 | G | A | 2.65E−02 | −2.22 | 2.56E−02 | −2.23 | 7.85E−03 | −2.66 | 2.59E−01 | −1.13 | 6.46E−05 |
| rs10491401 | 25836846 | T | C | 2.65E−02 | −2.22 | 2.56E−02 | −2.23 | 7.85E−03 | −2.66 | 2.47E−01 | −1.16 | 6.33E−05 |
| rs2619940 | 25837489 | C | T | 2.80E−02 | −2.20 | 2.77E−02 | −2.20 | 7.85E−03 | −2.66 | 2.80E−01 | −1.08 | 7.64E−05 |
| rs2619941 | 25837528 | A | G | 2.65E−02 | −2.22 | 2.56E−02 | −2.23 | 7.85E−03 | −2.66 | 2.47E−01 | −1.16 | 6.33E−05 |
| rs2619942 | 25837575 | A | G | 2.65E−02 | −2.22 | 2.56E−02 | −2.23 | 7.85E−03 | −2.66 | 2.47E−01 | −1.16 | 6.33E−05 |
| rs367519 | 25838585 | C | T | 2.65E−02 | −2.22 | 2.56E−02 | −2.23 | 7.85E−03 | −2.66 | 2.47E−01 | −1.16 | 6.33E−05 |
| rs11740209 | 25875893 | C | T | 2.93E−03 | −2.98 | 4.91E−03 | −2.81 | 5.85E−03 | −2.76 | 1.90E−01 | −1.31 | 1.08E−06 |
| rs409649 | 25876920 | G | A | 4.69E−03 | −2.83 | 2.88E−04 | −3.63 | 4.68E−03 | −2.83 | 5.48E−01 | −0.60 | 1.82E−07 |
| rs10058083 | 25930155 | A | G | 1.63E−03 | 3.15 | 1.69E−03 | 3.14 | 7.67E−05 | 3.95 | 9.34E−01 | −0.08 | 5.23E−08 |
| rs4701511 | 25931761 | C | A | 3.27E−05 | −4.15 | 7.12E−04 | −3.39 | 9.06E−03 | −2.61 | 6.94E−02 | −1.82 | 2.63E−09 |
| rs6894102 | 25933313 | C | T | 1.63E−03 | 3.15 | 1.69E−03 | 3.14 | 7.67E−05 | 3.95 | 9.96E−01 | 0.01 | 4.81E−08 |
| rs7705715 | 25935171 | T | C | 3.27E−05 | −4.15 | 6.18E−04 | −3.42 | 1.01E−02 | −2.57 | 5.26E−02 | −1.94 | 2.20E−09 |
| rs13176113 | 25936197 | A | G | 3.27E−05 | −4.15 | 6.18E−04 | −3.42 | 1.52E−02 | −2.43 | 5.26E−02 | −1.94 | 3.16E−09 |
| rs4701259 | 25936855 | A | G | 4.08E−05 | −4.10 | 6.86E−04 | −3.40 | 9.06E−03 | −2.61 | 3.23E−02 | −2.14 | 2.16E−09 |
| rs17482975 | 25937365 | T | C | 5.43E−05 | −4.04 | 5.58E−04 | −3.45 | 6.56E−03 | −2.72 | 2.26E−02 | −2.28 | 1.45E−09 |
| rs13187934 | 25938125 | T | C | 6.50E−05 | −3.99 | 5.73E−04 | −3.44 | 6.56E−03 | −2.72 | 2.26E−02 | −2.28 | 1.74E−09 |
| rs11739167 | 25945521 | T | C | 4.92E−03 | 2.81 | 3.11E−04 | 3.61 | 1.34E−05 | 4.35 | 5.18E−01 | −0.65 | 2.02E−08 |
| rs10942147 | 25946686 | A | G | 3.30E−05 | −4.15 | 7.41E−04 | −3.37 | 8.07E−03 | −2.65 | 2.23E−02 | −2.28 | 1.54E−09 |
| rs9293194 | 25946893 | A | C | 4.92E−03 | 2.81 | 3.11E−04 | 3.61 | 5.30E−06 | 4.55 | 5.18E−01 | −0.65 | 1.26E−08 |
| rs12521388 | 25947870 | A | G | 3.30E−05 | −4.15 | 7.41E−04 | −3.37 | 7.47E−03 | −2.68 | 2.23E−02 | −2.28 | 1.44E−09 |
| rs1346536 | 25951409 | G | A | 9.36E−03 | 2.60 | 1.87E−04 | 3.73 | 5.30E−06 | 4.55 | 5.18E−01 | −0.65 | 1.61E−08 |
| rs12697669 | 25954780 | A | C | 1.85E−03 | −3.11 | 2.02E−02 | −2.32 | 2.01E−02 | −2.33 | 6.60E−03 | −2.72 | 2.53E−06 |
| rs12659830 | 25956158 | T | G | 1.80E−01 | 1.34 | 6.57E−03 | 2.72 | 3.16E−05 | 4.16 | 6.40E−01 | 0.47 | 1.73E−05 |
| rs6452304 | 25959985 | T | C | 6.39E−05 | −4.00 | 7.33E−04 | −3.38 | 8.49E−03 | −2.63 | 2.26E−02 | −2.28 | 2.78E−09 |
| rs6452305 | 25960379 | A | C | 6.39E−05 | −4.00 | 7.33E−04 | −3.38 | 8.49E−03 | −2.63 | 2.26E−02 | −2.28 | 2.78E−09 |
| rs7380139 | 25962123 | A | G | 4.15E−05 | −4.10 | 1.00E−03 | −3.29 | 8.49E−03 | −2.63 | 2.26E−02 | −2.28 | 2.72E−09 |
| rs6873221 | 25964323 | A | G | 4.45E−03 | 2.84 | 2.54E−04 | 3.66 | 6.74E−06 | 4.50 | 5.38E−01 | −0.62 | 1.01E−08 |
| rs10063934 | 25968364 | A | G | 1.38E−01 | 1.48 | 7.20E−03 | 2.69 | 4.78E−05 | 4.07 | 8.56E−01 | 0.18 | 1.92E−05 |
| rs12519594 | 25970562 | A | G | 4.15E−05 | −4.10 | 1.03E−03 | −3.28 | 8.49E−03 | −2.63 | 2.23E−02 | −2.29 | 2.78E−09 |
| rs12187724 | 25970827 | C | A | 1.09E−01 | 1.60 | 1.20E−02 | 2.51 | 4.78E−05 | 4.07 | 6.28E−01 | 0.48 | 1.85E−05 |
| rs10214380 | 25982692 | T | C | 6.58E−03 | −2.72 | 4.64E−02 | −1.99 | 3.73E−02 | −2.08 | 6.50E−04 | −3.41 | 1.84E−05 |
| rs4475231 | 25991074 | T | C | 2.76E−05 | −4.19 | 1.03E−03 | −3.28 | 9.33E−03 | −2.60 | 1.66E−02 | −2.40 | 1.92E−09 |
| rs12187661 | 25995303 | T | C | 1.90E−01 | 1.31 | 9.28E−03 | 2.60 | 2.49E−04 | 3.66 | 1.84E−02 | 2.36 | 1.55E−05 |
| rs6891206 | 26005136 | T | C | 5.81E−04 | −3.44 | 2.10E−03 | −3.08 | 1.73E−02 | −2.38 | 2.49E−03 | −3.02 | 5.04E−08 |
| rs13166776 | 26007113 | C | T | 4.08E−05 | −4.10 | 9.78E−04 | −3.30 | 1.11E−02 | −2.54 | 1.73E−02 | −2.38 | 2.95E−09 |

TABLE 11-continued

Imputation-driven meta-analysis on four cohorts identifies additional SNPs with $P < 1 \times 10^{-4}$ on the 5p14.1 region. A1 and A2 refer to allele 1 and allele 2, respectively, and Z-scores reflect the direction of association for the A1 allele.

| SNP | Position | A1 | A2 | P (AGRE) | Z (AGRE) | P (ACC) | Z (ACC) | P (CAP) | Z (CAP) | P (cart) | Z (cart) | P (combined) |
|---|---|---|---|---|---|---|---|---|---|---|---|---|
| rs6898772 | 26081809 | C | T | 6.63E−02 | 1.84 | 1.31E−03 | 3.21 | 8.55E−03 | 2.63 | 7.71E−01 | −0.29 | 3.42E−05 |
| rs12516367 | 26084181 | C | T | 6.63E−02 | 1.84 | 1.14E−03 | 3.25 | 8.55E−03 | 2.63 | 7.64E−01 | −0.30 | 3.08E−05 |
| rs7720426 | 26101159 | A | G | 6.16E−02 | 1.87 | 1.04E−03 | 3.28 | 2.26E−03 | 3.05 | 7.90E−01 | −0.27 | 1.17E−05 |
| rs12173236 | 26107233 | T | C | 6.16E−02 | 1.87 | 9.69E−04 | 3.30 | 2.71E−03 | 3.00 | 7.97E−01 | −0.26 | 1.22E−05 |
| rs1330642 | 26108995 | T | C | 6.70E−02 | 1.83 | 6.15E−04 | 3.42 | 1.44E−02 | 2.45 | 6.82E−01 | −0.41 | 2.93E−05 |
| (b) Genotyped SNPs | | | | | | | | | | | | |
| rs423116 | 25837046 | T | C | 1.69E−02 | −2.39 | 3.22E−02 | −2.14 | 7.85E−03 | −2.66 | 2.4E−01 | −1.16 | 5.30E−05 |
| rs10065041 | 25876207 | T | C | 2.72E−03 | −3.00 | 4.91E−03 | −2.81 | 5.85E−03 | −2.76 | 1.9E−01 | −1.31 | 1.01E−06 |
| rs7704909* | 25934678 | T | C | 1.60E−05 | 4.31 | 6.23E−04 | 3.42 | 9.06E−03 | −2.61 | 5.2E−02 | −1.94 | 1.12E−09 |
| rs1896731 | 25934777 | T | C | 1.67E−03 | −3.14 | 1.65E−03 | −3.15 | 7.67E−05 | 3.95 | 9.9E−01 | 0.01 | 4.80E−08 |
| rs10038113* | 25938099 | T | C | 1.43E−03 | −3.19 | 2.43E−03 | −3.03 | 2.75E−05 | 4.19 | 4.0E−01 | −0.83 | 7.90E−08 |
| rs7447989 | 25950789 | A | G | 1.44E−01 | −1.46 | 5.21E−03 | −2.79 | 3.29E−05 | 4.15 | 6.4E−01 | 0.46 | 1.03E−05 |
| rs6894838 | 25980703 | T | C | 5.05E−04 | −3.48 | 2.49E−02 | −2.24 | 1.61E−02 | −2.41 | 5.6E−03 | −2.77 | 9.06E−07 |
| rs12518194 | 25987318 | A | G | 1.32E−05 | 4.36 | 1.01E−03 | 3.29 | 9.33E−03 | −2.60 | 1.7E−02 | −2.37 | 1.07E−09 |
| rs4701260 | 25994662 | A | G | 1.03E−01 | 1.63 | 1.16E−02 | 2.52 | 1.67E−04 | 3.76 | 1.8E−02 | 2.36 | 6.79E−06 |
| rs4307059 | 26003460 | T | C | 1.07E−05 | 4.40 | 2.22E−04 | 3.69 | 1.16E−02 | −2.52 | 1.6E−02 | −2.40 | 2.07E−10 |
| rs4327572 | 26008578 | T | C | 2.20E−05 | −4.24 | 2.03E−03 | −3.09 | 7.34E−03 | −2.68 | 1.5E−02 | −2.42 | 2.71E−09 |
| rs12514304 | 26092874 | T | G | 7.57E−02 | 1.78 | 2.59E−03 | 3.01 | 3.35E−03 | 2.93 | 7.4E−01 | −0.32 | 4.14E−05 |
| rs10072518 | 26100560 | T | C | 1.23E−01 | −1.54 | 9.41E−04 | −3.31 | 4.40E−03 | 2.85 | 2.5E−01 | 1.14 | 1.29E−05 |

*Analysis on rs7704909 and rs10038113 in the CART cohort were based on imputed data.

TABLE 12

In addition to genotyped markers, whole-genome imputation identified multiple loci with suggestive association with ASDs in the combined analysis of discovery cohorts. The table below lists genotyped and imputed markers with P-values $<1 \times 10^{-5}$ (excluding 5p14.1 region). A1 and A2 refer to allele 1 and allele 2, respectively, and the allele frequencies below are calculated based on allele 1 in AGRE parents or in ACC control subjects.

| SNP | Chr | Position | marker_type | locus | closest gene | SNP-gene distance | A1 | A2 |
|---|---|---|---|---|---|---|---|---|
| rs3755827 | 3 | 62335411 | genotyped | 3p14.2 | FEZF2 | 1181 | T | C |
| rs2248535 | 3 | 110169600 | imputed | 3q13.13 | MORC1 | 0 | G | A |
| rs9395885 | 6 | 53853436 | imputed | 6p12.1 | LRRC1 | 0 | T | C |
| rs9349687 | 6 | 53868708 | imputed | 6p12.1 | LRRC1 | 0 | A | T |
| rs9349688 | 6 | 53870051 | genotyped | 6p12.1 | LRRC1 | 0 | A | G |
| rs9384952 | 6 | 116066757 | genotyped | 6q22.1 | FRK | 302629 | T | C |
| rs4877463 | 9 | 90419466 | imputed | 9q22.1 | LOC286238 | 32448 | T | C |
| rs7966486 | 12 | 89991354 | imputed | 12q21.33 | KERA | 15092 | G | T |
| rs10774538 | 12 | 118888180 | genotyped | 12q24.23 | CCDC64 | 23851 | T | C |
| rs9521337 | 13 | 108823637 | imputed | 13q33.3 | MYO16 | 165281 | T | G |
| rs943767 | 13 | 108828552 | imputed | 13q33.3 | MYO16 | 170196 | G | T |
| rs7996916 | 13 | 108855628 | imputed | 13q33.3 | MYO16 | 197272 | A | C |
| rs1328250 | 13 | 108856632 | imputed | 13q33.3 | MYO16 | 198276 | T | C |
| rs9521354 | 13 | 108865125 | genotyped | 13q33.3 | MYO16 | 206769 | A | C |
| rs9521355 | 13 | 108865183 | genotyped | 13q33.3 | MYO16 | 206827 | T | C |
| rs1328244 | 13 | 108881899 | genotyped | 13q33.3 | MYO16 | 223543 | T | C |
| rs12897470 | 14 | 39895590 | imputed | 14q21.1 | FBXO33 | 924135 | G | A |
| rs12100820 | 14 | 39899940 | imputed | 14q21.1 | FBXO33 | 928485 | T | A |
| rs12586354 | 14 | 39900960 | imputed | 14q21.1 | FBXO33 | 929505 | A | T |
| rs7143615 | 14 | 39901688 | imputed | 14q21.1 | FBXO33 | 930233 | C | G |
| rs7147817 | 14 | 39901754 | genotyped | 14q21.1 | FBXO33 | 930299 | A | G |
| rs17783432 | 14 | 76141161 | genotyped | 14q24.3 | ESRRB | 104200 | T | G |
| rs4480786 | 16 | 8412290 | imputed | 16p13.2 | C16orf68 | 210738 | G | A |
| rs7206043 | 16 | 8412954 | imputed | 16p13.2 | C16orf68 | 210074 | G | A |
| rs7206246 | 16 | 8413011 | imputed | 16p13.2 | C16orf68 | 210017 | T | A |
| rs9932538 | 16 | 19116070 | genotyped | 16p12.3 | SYT17 | 0 | A | G |
| rs6131030 | 20 | 44241393 | genotyped | 20q13.12 | CDH22 | 0 | A | G |

| SNP | A1_Freq (AGRE parents) | P (AGRE) | A1_Freq (ACC control) | P (ACC) | Odds Ratio (ACC) | P (combined) |
|---|---|---|---|---|---|---|
| rs3755827 | 0.87 | 7.47E−04 | 0.86 | 6.73E−04 | 1.27 | 3.54E−06 |
| rs2248535 | 0.39 | 1.08E−03 | 0.43 | 8.75E−04 | 0.86 | 6.28E−06 |
| rs9395885 | 0.08 | 2.34E−02 | 0.10 | 1.57E−05 | 0.70 | 4.97E−06 |
| rs9349687 | 0.08 | 3.33E−02 | 0.10 | 2.17E−05 | 0.70 | 9.69E−06 |

TABLE 12-continued

In addition to genotyped markers, whole-genome imputation identified multiple loci with suggestive association with ASDs in the combined analysis of discovery cohorts. The table below lists genotyped and imputed markers with P-values $<1 \times 10^{-5}$ (excluding 5p14.1 region). A1 and A2 refer to allele 1 and allele 2, respectively, and the allele frequencies below are calculated based on allele 1 in AGRE parents or in ACC control subjects.

| | | | | | | |
|---|---|---|---|---|---|---|
| rs9349688 | 0.91 | 3.62E−02 | 0.90 | 1.49E−05 | 1.43 | 8.08E−06 |
| rs9384952 | 0.59 | 2.00E−02 | 0.58 | 4.66E−05 | 1.20 | 9.41E−06 |
| rs4877463 | 0.33 | 5.30E−04 | 0.35 | 2.43E−03 | 0.86 | 9.18E−06 |
| rs7966486 | 0.13 | 3.21E−02 | 0.13 | 1.82E−05 | 1.31 | 8.12E−06 |
| rs10774538 | 0.13 | 1.20E−02 | 0.12 | 5.69E−05 | 1.29 | 6.22E−06 |
| rs9521337 | 0.13 | 1.58E−02 | 0.14 | 2.97E−05 | 0.75 | 5.07E−06 |
| rs943767 | 0.13 | 2.05E−02 | 0.14 | 4.09E−05 | 0.75 | 8.76E−06 |
| rs7996916 | 0.12 | 2.17E−03 | 0.15 | 4.23E−04 | 0.79 | 6.03E−06 |
| rs1328250 | 0.12 | 2.17E−03 | 0.14 | 4.74E−04 | 0.79 | 6.67E−06 |
| rs9521354 | 0.87 | 7.25E−04 | 0.86 | 1.16E−03 | 1.25 | 5.79E−06 |
| rs9521355 | 0.13 | 1.37E−03 | 0.14 | 8.00E−04 | 0.80 | 7.11E−06 |
| rs1328244 | 0.92 | 8.71E−05 | 0.90 | 9.57E−04 | 1.31 | 8.22E−07 |
| rs12897470 | 0.50 | 7.07E−04 | 0.49 | 4.21E−04 | 1.17 | 2.17E−06 |
| rs12100820 | 0.50 | 7.07E−04 | 0.49 | 4.45E−04 | 1.17 | 2.29E−06 |
| rs12586354 | 0.47 | 2.06E−03 | 0.46 | 5.04E−05 | 1.20 | 8.99E−07 |
| rs7143615 | 0.50 | 7.07E−04 | 0.49 | 4.81E−04 | 1.17 | 2.45E−06 |
| rs7147817 | 0.46 | 7.33E−04 | 0.46 | 4.11E−05 | 1.20 | 2.75E−07 |
| rs17783432 | 0.15 | 4.90E−02 | 0.15 | 1.07E−05 | 0.73 | 9.35E−06 |
| rs4480786 | 0.42 | 5.01E−03 | 0.40 | 2.99E−04 | 1.18 | 9.86E−06 |
| rs7206043 | 0.41 | 2.47E−03 | 0.39 | 1.42E−04 | 1.19 | 2.62E−06 |
| rs7206246 | 0.41 | 3.50E−03 | 0.39 | 1.72E−04 | 1.19 | 4.32E−06 |
| rs9932538 | 0.84 | 4.87E−02 | 0.83 | 4.13E−08 | 1.47 | 1.94E−07 |
| rs6131030 | 0.42 | 1.21E−03 | 0.41 | 8.15E−04 | 0.86 | 6.46E−06 |

Figure 2:
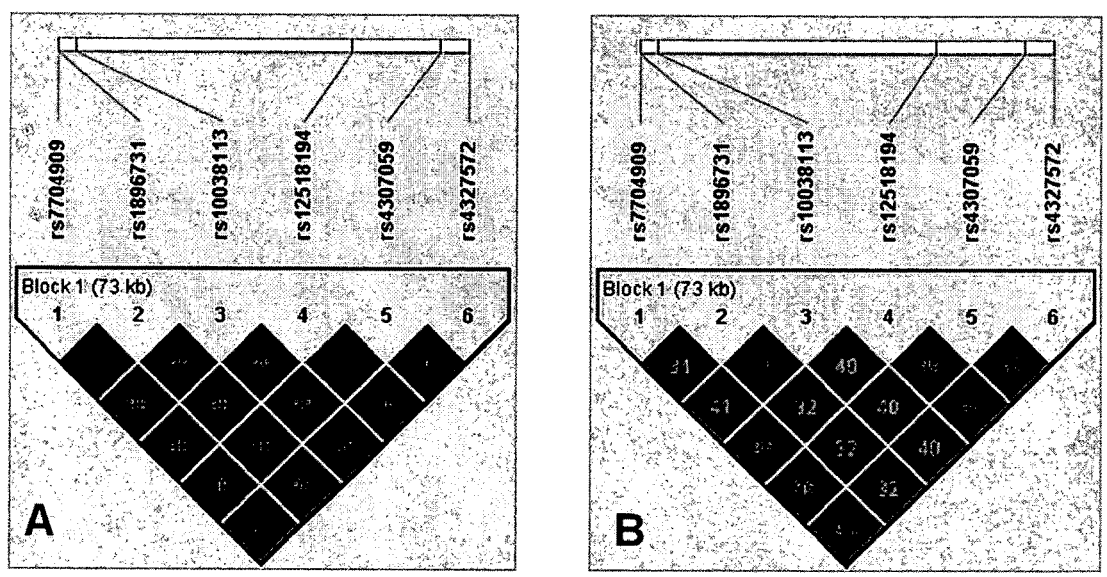
FIG. 2. The linkage disequilibrium between the six SNPs in Table 8. Both D' measure (A) and $r^2$ measure (B) are shown. The figure is generated by Haploview (27).
Figure 3:
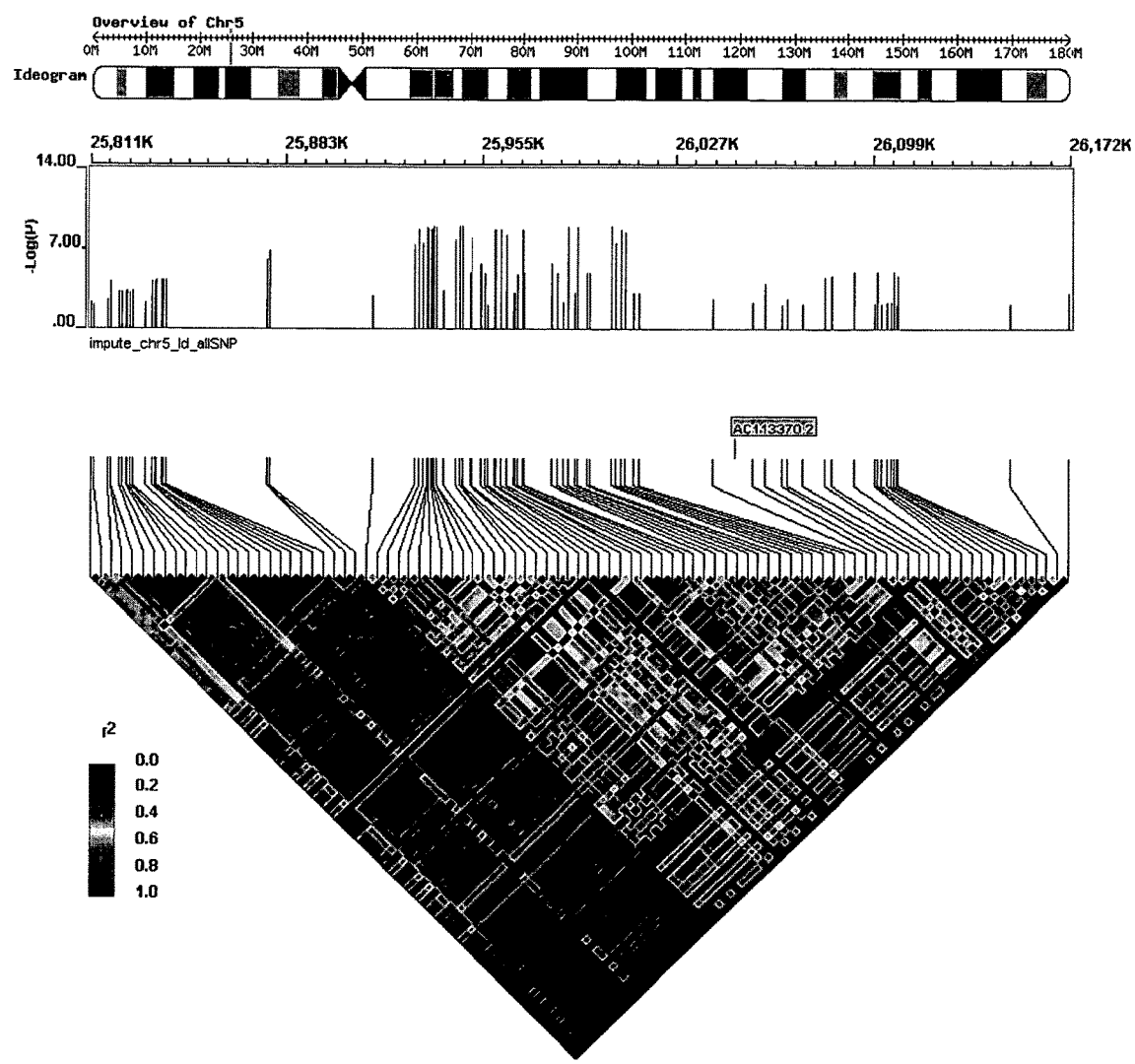
FIG. 3. The linkage disequilibrium plot for all the genotyped/imputed SNPs on 5p14.1 region, with their combined P-values (as −log 10 values) on four cohorts (markers with $P<1\times10^{-7}$ are highlighted in red color). All the most significant SNPs in this region fall within the same LD block. The figure is generated by WGAViewer (33).
Figure 4:
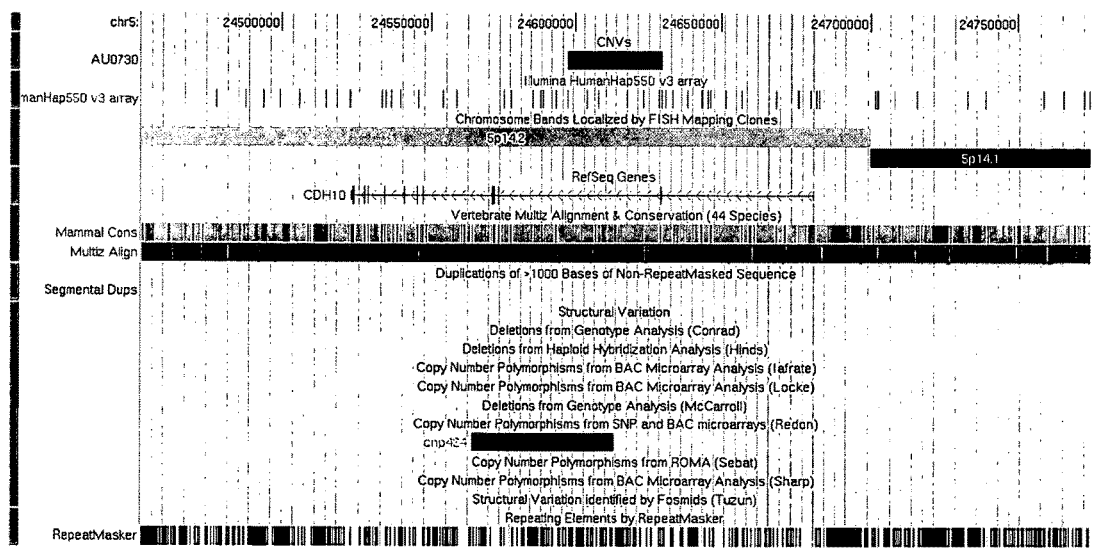
FIG. 4. CNVs between CDH10 and CDH9 in our study, as visualized in the UCSC Genome Browser. We attempted experimental validation of intergenic CNVs by quantitative PCR (QPCR) and by multiplex ligation-dependent probe amplification (MLPA) assay. Each panel below illustrates one CNV loci overlapping or between CDH10 and CDH9, and the red bar in each panel represents the location and coordinate of the CNVs.
Figure 4:
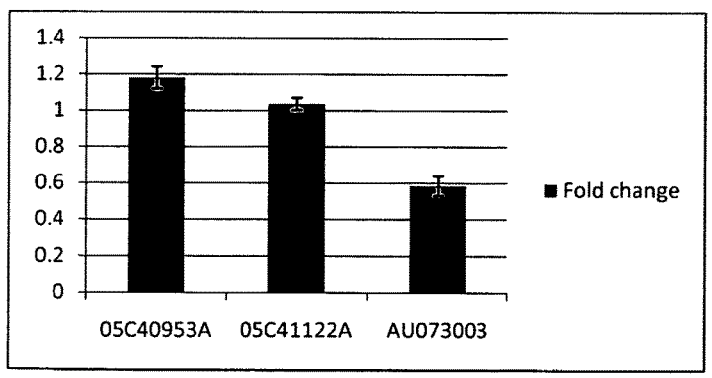
Figure 4:
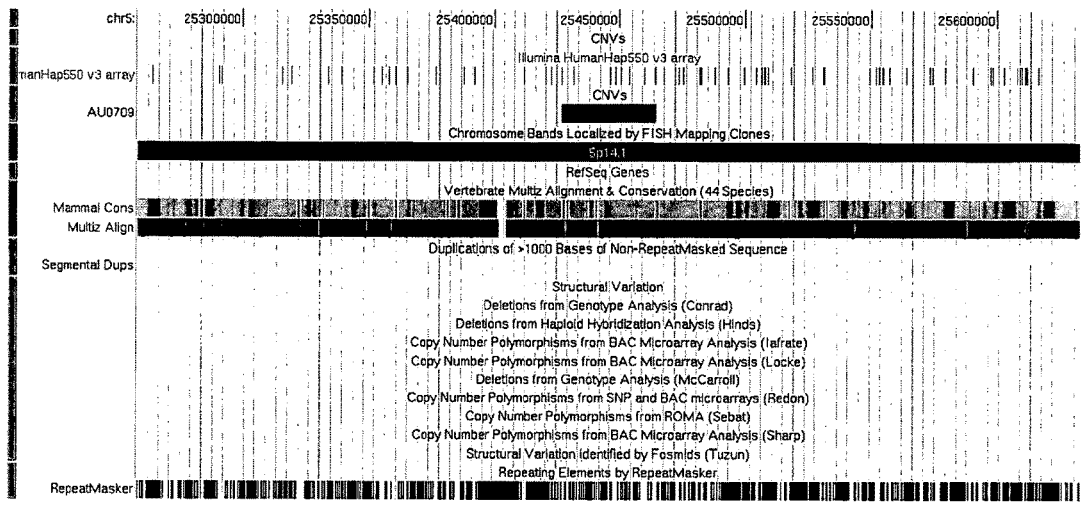
Figure 4:
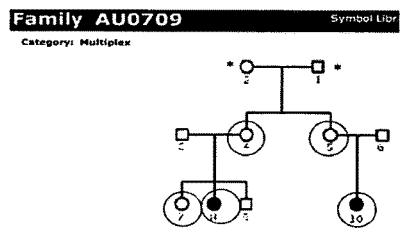
Figure 4:
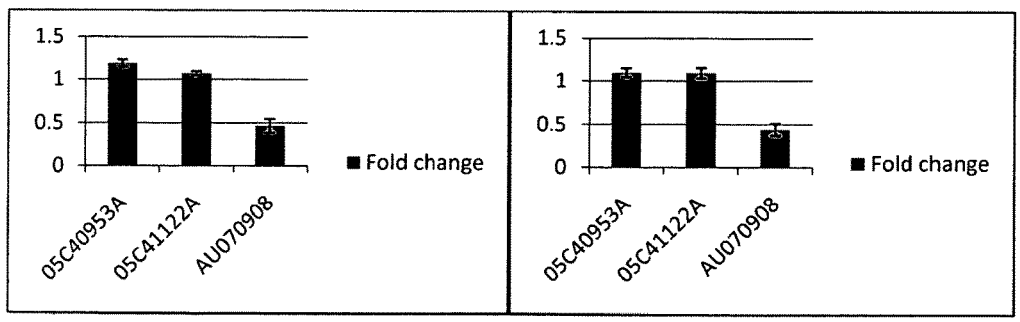
Figure 4:
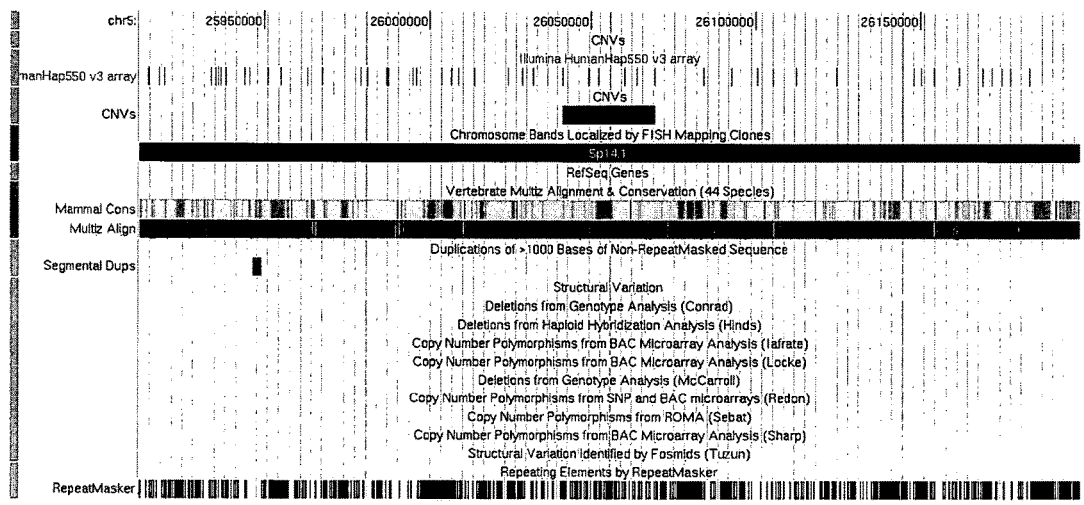
Figure 4:
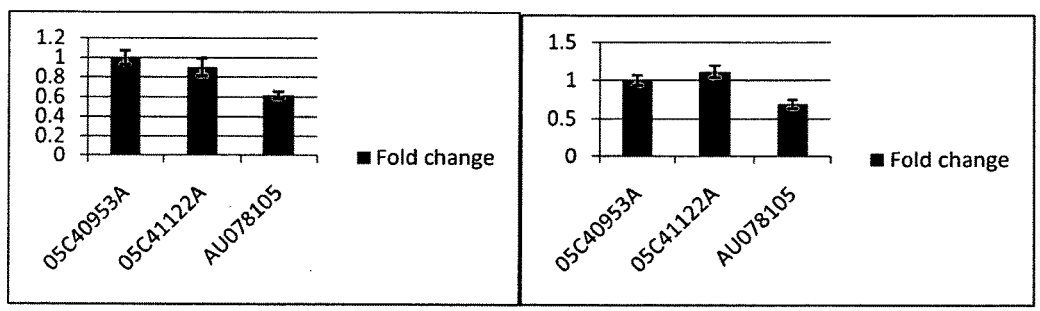
Figure 4:
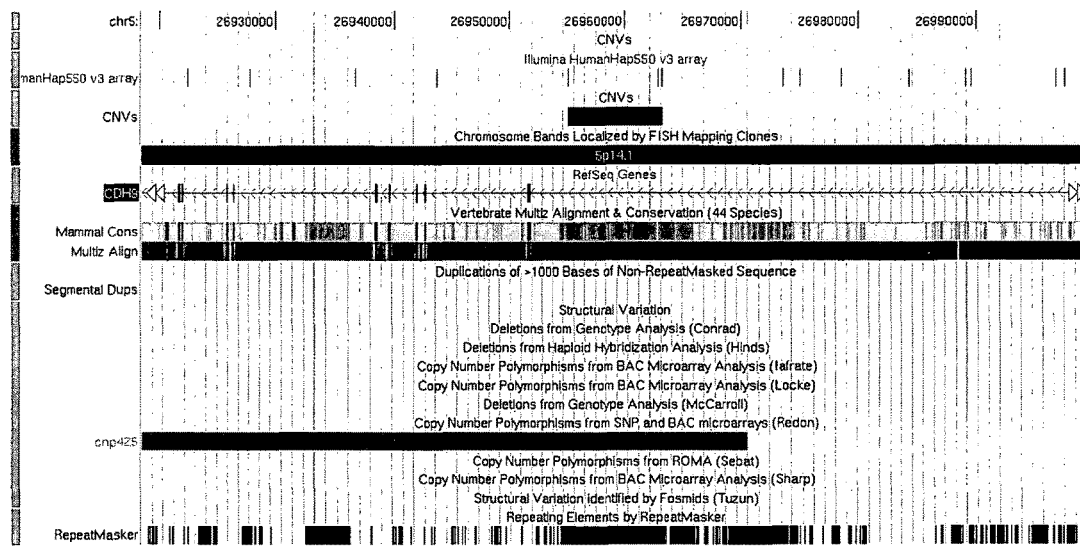
Figure 5:
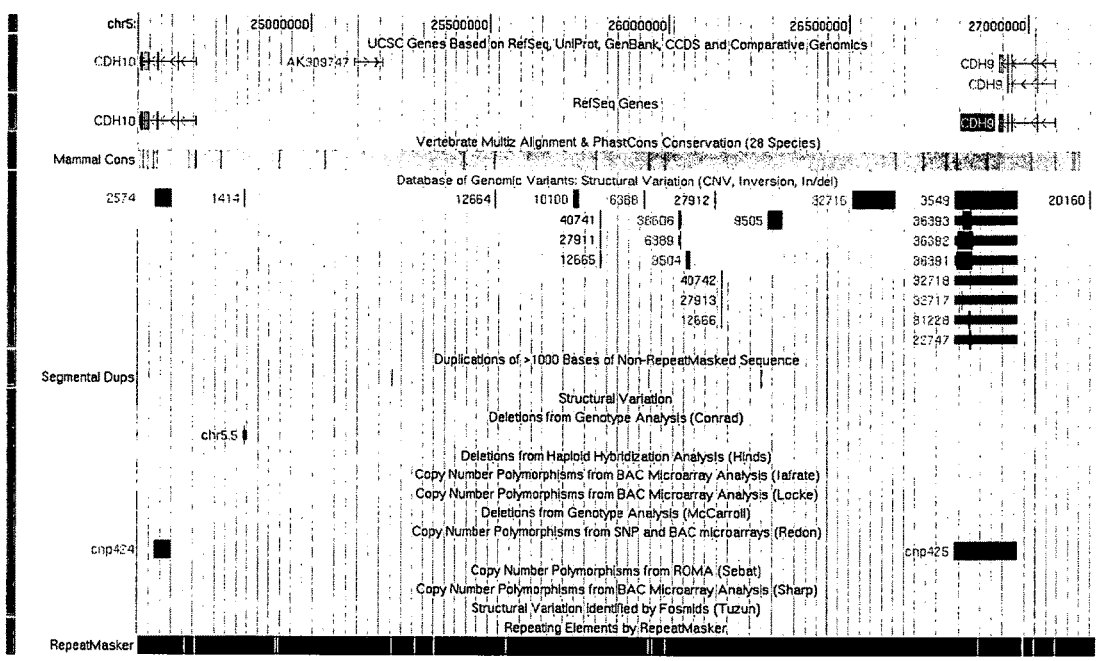
FIG. 5. Previously reported CNVs between CDH10 and CDH9, as annotated in the UCSC Genome Browser annotation databases. Two tracks were displayed in the browser, including the Database of Genomic Variants (http://projects.tcag.ca/variation/) track, as well as "Structural Variation" track compiled from nine previous publications. Both tracks indicate that no common CNVs were identified between CDH10 and CDH9, although a CNV that disrupts CDH9 3' region has been detected in multiple subjects. Therefore, unless a very small CNV exists that evades detection by current technical platforms, the top SNP association result is unlikely to be due to the linkage disequilibrium with a CNV.
Figure 6:
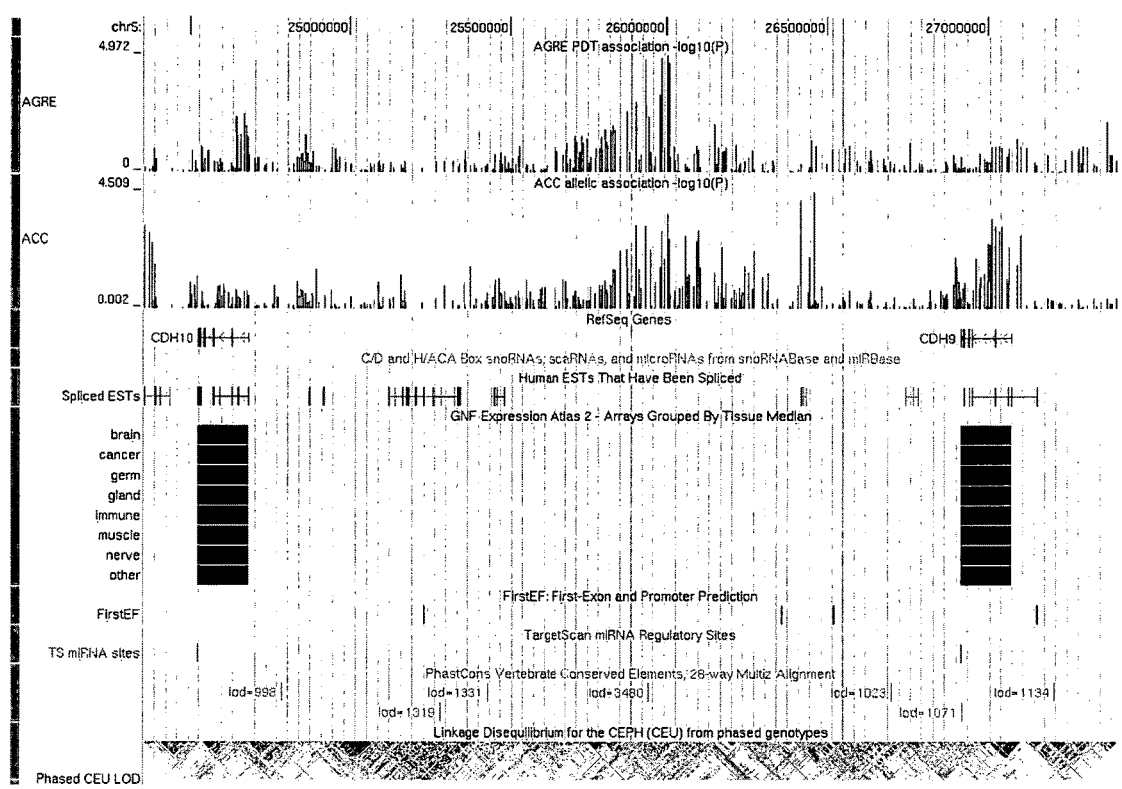
FIG. 6. Genome browser shot of the genomic region between CDH10 and CDH9. The SNP association results for the AGRE cohort and ACC cohort are displayed as vertical lines that represent $-\log_{10}(P)$ values. There are no known microRNAs or small nuclear RNA in this region, as shown in the Genome Browser track. There are no spliced human Expressed Sequence Tags (ESTs) that overlap with the LD block, as shown in the "Human EST" track (34). The expression values (color changes from red to black to green with decreasing expression) for different groups of human tissues are displayed in the "GNF Expression Atlas 2" track (26). The predicted transcription start sites are displayed in the "FirstEF" track (35), and no such sites overlap with the LD block. The predicted microRNA targets were displayed in the "TargetScan" track (36), and none of them overlap with the LD block. The conserved genomic elements are displayed in the PhastCons track (37) with LOD scores.

Closer examination of the 5p14.1 region indicated that all genotyped and imputed SNPs with P-values below $1 \times 10^{-7}$ reside within the same ~100 kb linkage disequilibrium (LD) block, suggesting that these SNPs are tagging the same variants. See FIGS. 2 and 3). The LD block is located within a 2.2 Mb intergenic region between CDH10 (cadherin 10) and CDH9 (cadherin 9) (FIG. 1B, 1C). Both CDH10 and CDH9 encode type II classical cadherins from the cadherin superfamily, which represent trans-membrane proteins that mediate calcium-dependent cell-cell adhesion. To search for other types of variants, including structural variants, within the 2.2 Mb intergenic region, we used the PennCNV software[22] on the signal intensity data and identified five CNV loci within the region (FIG. 4). All of these CNVs are present in control subjects in our study, and three of the five CNVs are also reported in the Database for Genomic Variants that annotates healthy individuals (FIG. 5), suggesting that rare CNVs in the region are unlikely to be causal variants for ASDs. We next focused on the ~100 kb LD block harboring the most significant SNPs, and determined whether other transcripts or functional elements are located within the block. By examining the UCSC Genome Browser annotations, we did not identify predicted genes, predicted transcription start sites, spliced human EST sequences, known microRNA genes or predicted microRNA targets that overlap with the LD block (FIG. 6). However, we note that the LD block contains multiple highly conserved genomic elements, including a 849-bp element that ranks as the top 0.026% most conserved elements in the entire human genome (LOD score=3,480 by PhastCons[23], FIG. 1B). Consistent with previous reports that large stable gene deserts typically contain regulatory elements for genes involved in development or transcription[24], we hypothesized that these tagging SNPs were capturing the association of functional variant(s) that regulate the expression and action of either CDH10 or CDH9.

Figure 7:
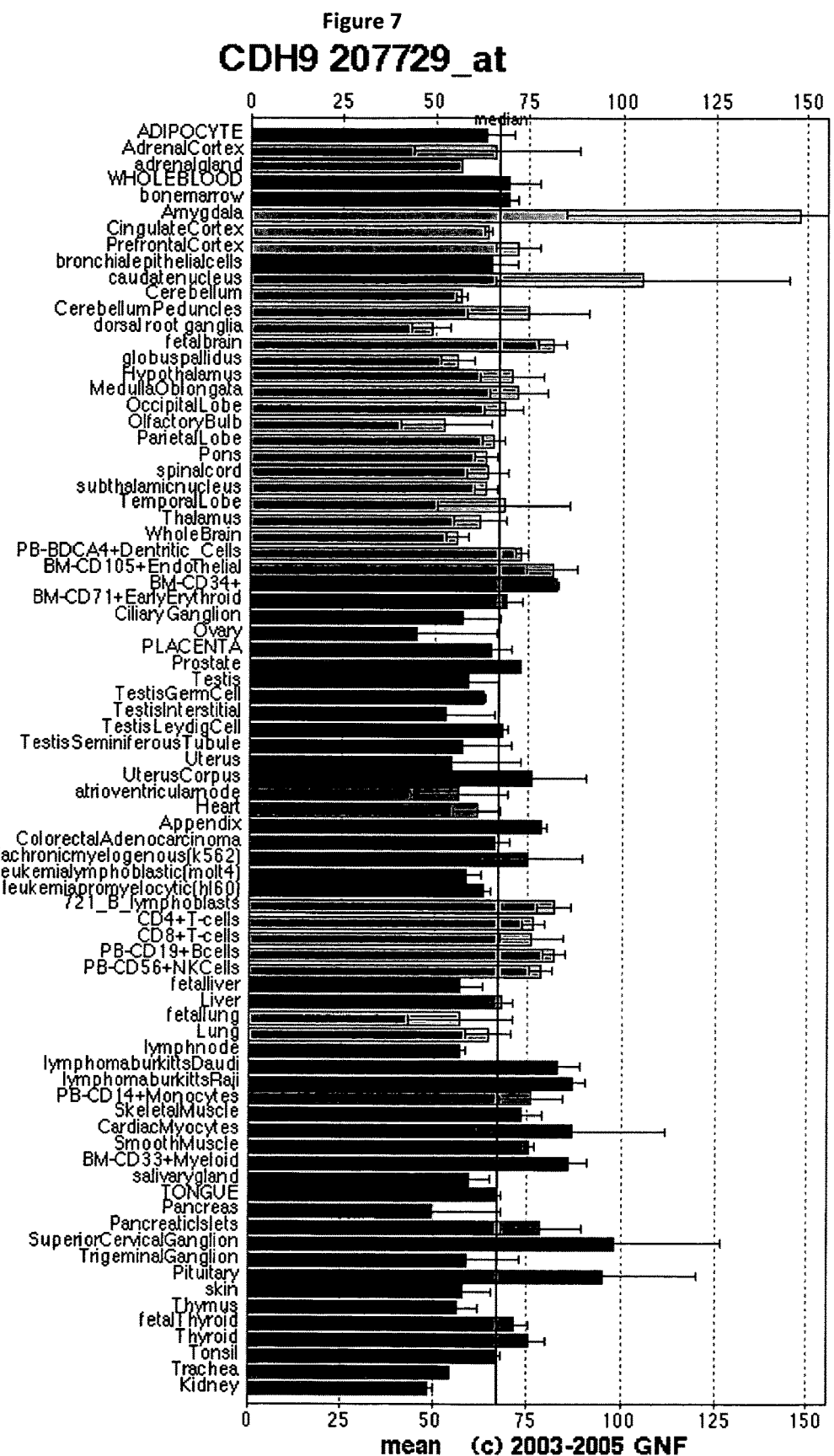
FIG. 7. The tissue-specific gene expression levels for CDH9 (probe identifier: 207729_at), based on the GNF SymAtlas database on 79 human tissues. The black line represents median value.
Figure 8:
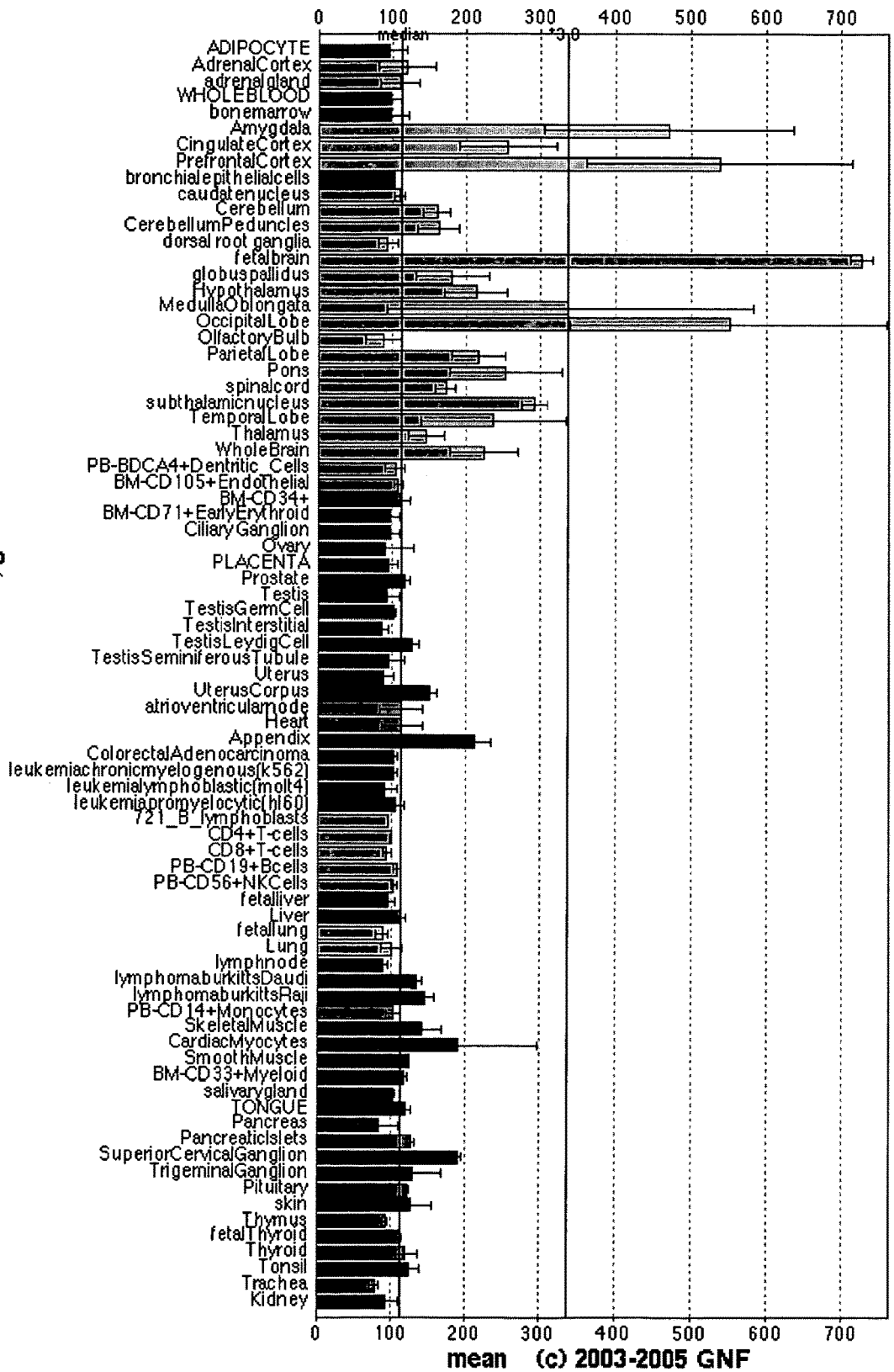
FIG. 8. The tissue-specific gene expression levels for CDH10 (probe identifier: 220115_s_at), based on the GNF SymAtlas database on 79 human tissues. The black line and blue line represent median value and its 3 fold value, respectively.

Since CDH10 and CDH9 are expressed at low levels in non-neural tissues (FIGS. 7 and 8), we evaluated their mRNA distribution in human fetal brain by in situ hybridization (Supplementary Methods). Although CDH9 showed uniformly low levels of expression, a striking pattern of enrichment in frontal cortex was observed for CDH10 (FIG. 1D). These results are consistent with previous work showing high levels of CDH10 in the human fetal brain[25] and a prominent enrichment of CDH10 mRNA in the anterior cortical plate of the developing mouse brain[26]. We next examined the SNPExpress database[27] that profiles gene expression in 93 human cortical brain tissues from genotyped subjects, but none of the SNPs in Table 8 associated with expression levels for either CDH9 (P=0.92 for rs4307059) or CDH10 (P=0.86 for rs4307059) (FIG. 1E). Although the small sample size may not have sufficient power to detect subtle effect sizes, it is also possible that the causal variants regulate gene expression only in the developing brain, or that the causal variant targets an unidentified functional element, similar to the variants reported in the intergenic region on 8q24, which has been implicated in various cancers[28,29].

Recent genetic studies have identified several neuronal cell-adhesion genes, including NRXN1 (neurexin 1)[30,31], CNTNAP2 (contactin-associated protein-like 2)[32-34] and PCDH10 (protocadherin 10)[35], as potentially disrupted in rare ASD cases. Cadherins represent a large group of trans-membrane proteins that are involved in cell adhesion and generation of synaptic complexity in the developing brain[36]. In light of the above information, we note that several other cadherin genes were also tagged by the top 1,000 most significant SNPs of the combined discovery cohorts (Table 13). In addition, SNPs surrounding several prominent ASD candidate loci[1], including CACNA1C, CNTNAP2, GRIK2, NRXN1 and NLGN4X, also show suggestive evidence of association (Table 14). To examine if cell adhesion molecules, as a gene family, associate with ASDs, we applied two pathway-based association approaches (Supplementary Methods). Firstly, we examined the distribution of Simes-adjusted P-values for each gene in the discovery cohorts, and found that a group of 25 related cadherin genes show more significant association with ASDs than all other genes (P=0.02), whereas stronger enrichment signal (P=0.004) was obtained when the 25 cadherin genes were combined with eight neurexin

TABLE 13

Association results for genotyped SNPs within/nearby cadherins and protocadherins (other than CDH9/CDH10) among the top 1000 most significant SNPs in the combined analysis of the discovery cohorts. A1 and A2 refer to allele 1 and allele 2, respectively, and the allele frequencies below are calculated based on allele 1 in AGRE parents or in ACC control subjects.

| SNP | Chr | Position | Closest gene | SNP-gene distance | A1 | A2 | A1_Freq (AGRE parents) | P (AGRE) | A1_Freq (ACC control) | P (ACC) | Odds Ratio (ACC) | P (combined) |
|---|---|---|---|---|---|---|---|---|---|---|---|---|
| rs3775330 | 4 | 30337382 | PCDH7 | 0 | A | G | 0.8639 | 0.084181 | 0.8731 | 0.001745 | 0.82 | 0.000765 |
| rs2879041 | 4 | 33041141 | PCDH7 | 2283622 | T | G | 0.91786 | 0.818546 | 0.90831 | 1.18E−05 | 1.48 | 0.001058 |
| rs17547161 | 4 | 133152254 | PCDH10 | 1137666 | A | G | 0.90241 | 0.056483 | 0.897 | 0.001865 | 0.81 | 0.000521 |
| rs3857321 | 5 | 21926009 | CDH12 | 0 | A | G | 0.8037 | 0.000854 | 0.7827 | 0.07409 | 1.10 | 0.000537 |
| rs6452027 | 5 | 21937473 | CDH12 | 0 | T | C | 0.8033 | 0.00075 | 0.7798 | 0.07461 | 1.10 | 0.000496 |
| rs13162273 | 5 | 21953276 | CDH12 | 0 | A | C | 0.7956 | 0.002102 | 0.7808 | 5.06E−02 | 1.11 | 0.000645 |
| rs2026410 | 10 | 56015517 | PCDH15 | 0 | T | C | 0.1772 | 0.252904 | 0.1699 | 0.000258 | 1.23 | 0.000793 |
| rs11647166 | 16 | 60923063 | CDH8 | 295526 | A | G | 0.05486 | 0.235271 | 0.06127 | 0.000449 | 0.69 | 0.001033 |
| rs318203 | 16 | 62807919 | CDH11 | 730265 | A | G | 0.8875 | 0.275189 | 0.9021 | 0.000135 | 0.77 | 0.000587 |
| rs11862535 | 16 | 82218967 | CDH13 | 0 | A | G | 0.4485 | 0.013527 | 0.4397 | 0.01603 | 1.11 | 0.000845 |
| rs11564334 | 18 | 23735780 | CDH2 | 49153 | A | G | 0.6663 | 0.012173 | 0.6715 | 0.01791 | 0.90 | 0.000858 |
| rs8098920 | 18 | 23755999 | CDH2 | 28934 | A | G | 0.4773 | 0.010397 | 0.4623 | 0.02113 | 1.11 | 0.000883 |
| rs11083238 | 18 | 23777488 | CDH2 | 7445 | T | C | 0.4965 | 0.015573 | 0.5134 | 0.009464 | 0.89 | 0.000587 |
| rs11564410 | 18 | 23888092 | CDH2 | 0 | A | G | 0.2794 | 0.027227 | 0.2572 | 0.009571 | 1.14 | 9.79E−04 |
| rs9965582 | 18 | 23951510 | CDH2 | 0 | A | G | 0.2533 | 0.001612 | 0.2795 | 0.08672 | 0.92 | 0.000999 |
| rs7505845 | 18 | 62637464 | CDH19 | 215268 | A | G | 0.2194 | 0.063983 | 0.2254 | 0.000639 | 0.83 | 0.000262 |
| rs6131030 | 20 | 44241393 | CDH22 | 0 | A | G | 0.4199 | 0.001213 | 0.4106 | 0.000815 | 0.86 | 6.46E−06 |
| rs1321001 | 20 | 44250143 | CDH22 | 0 | T | G | 0.8437 | 0.011272 | 0.8483 | 0.01366 | 0.86 | 0.000623 |

TABLE 14

Top association results (P < 0.01) for genotyped SNPs within or surrounding prominent ASD loci previously implicated in linkage studies, cytogenetic studies and candidate gene association studies. This list of potential ASD loci was compiled from a recent review paper (16), including 8 "promising" genes and 18 "probable" genes.

| SNP | Closest gene | SNP-gene distance | A1 | A2 | A1_freq (AGRE) | P (AGRE) | A1_freq (ACC) | P (ACC) | Odds Ratio (ACC) | P (combined) |
|---|---|---|---|---|---|---|---|---|---|---|
| (a) Significant SNPs within or surrounding ASD candidate loci on autosomes are summarized below: | | | | | | | | | | |
| rs10495983 | NRXN1 | 67954 | T | C | 0.1195 | 0.00256896 | 0.1166 | 0.02217 | 0.85 | 0.000307 |
| rs11889255 | NRXN1 | 57977 | T | G | 0.1214 | 0.005084097 | 0.1177 | 0.01489 | 0.84 | 0.000351 |
| rs10495985 | NRXN1 | 54727 | T | C | 0.8826 | 0.002420425 | 0.8865 | 0.01763 | 1.19 | 0.000231 |
| rs11891766 | NRXN1 | 21019 | A | G | 0.1198 | 0.00887239 | 0.1164 | 0.0137 | 0.83 | 0.000511 |
| rs7604754 | NRXN1 | 0 | A | T | 0.1068 | 0.071860611 | 0.1067 | 0.004754 | 0.80 | 0.001402 |
| rs17494917 | NRXN1 | 0 | A | G | 0.8646 | 0.048899829 | 0.8596 | 0.02106 | 1.17 | 0.003311 |
| rs2078232 | NRXN1 | 0 | A | C | 0.1127 | 0.15840894 | 0.1151 | 3.38E−05 | 0.72 | 0.000104 |
| rs970896 | NRXN1 | 0 | A | C | 0.2396 | 0.295821428 | 0.2527 | 0.004915 | 0.86 | 0.007117 |
| rs10490237 | NRXN1 | 0 | T | G | 0.8647 | 0.324748158 | 0.8617 | 0.000414 | 1.28 | 0.001556 |
| rs4467312 | NRXN1 | 0 | T | C | 0.7206 | 0.652554154 | 0.7424 | 0.000738 | 0.85 | 0.006898 |
| rs10183349 | NRXN1 | 0 | T | C | 0.68 | 0.350503564 | 0.655 | 0.000185 | 1.20 | 0.001043 |
| rs858937 | NRXN1 | 0 | T | C | 0.8834 | 0.008496761 | 0.8762 | 0.1482 | 1.11 | 0.005816 |
| rs12616608 | NRXN1 | 562234 | A | G | 0.832 | 0.007517517 | 0.8447 | 0.2179 | 0.93 | 0.008474 |
| rs2953300 | NRXN1 | 592699 | T | C | 0.186 | 0.007090926 | 0.1645 | 0.007533 | 1.17 | 0.00024 |
| rs952893 | NRXN1 | 616553 | A | G | 0.8207 | 0.001659334 | 0.8348 | 0.4157 | 0.95 | 0.008184 |
| rs6758434 | NRXN1 | 641162 | A | C | 0.7981 | 0.002289891 | 0.8089 | 0.04787 | 0.90 | 0.000645 |
| rs7569104 | NRXN1 | 646423 | T | C | 0.1899 | 0.002935102 | 0.1811 | 0.02541 | 1.13 | 0.000392 |
| rs4146703 | NRXN1 | 650079 | A | G | 0.7934 | 0.005581081 | 0.8029 | 0.07404 | 0.91 | 0.001986 |
| rs6714367 | NRXN1 | 654680 | T | C | 0.8305 | 0.001250982 | 0.8446 | 0.07318 | 0.90 | 0.000686 |
| rs1028145 | NRXN1 | 668368 | T | G | 0.8584 | 8.24332E−05 | 0.8632 | 0.8058 | 0.98 | 0.005797 |
| rs4971757 | NRXN1 | 675074 | A | G | 0.8664 | 0.000594437 | 0.8677 | 0.4011 | 0.95 | 0.004341 |
| rs4353689 | NRXN1 | 675652 | A | C | 0.1269 | 0.001190066 | 0.1253 | 0.2783 | 1.07 | 0.003733 |
| rs2354387 | NRXN1 | 681044 | T | C | 0.8232 | 0.003188074 | 0.822 | 0.1675 | 0.92 | 0.003508 |
| rs1516194 | NRXN1 | 684059 | T | G | 0.1665 | 0.010675669 | 0.1681 | 0.1203 | 1.09 | 0.005382 |
| rs11125373 | NRXN1 | 686489 | A | G | 0.2044 | 0.00480634 | 0.2079 | 0.1145 | 1.09 | 0.002923 |
| rs10202118 | NRXN1 | 690650 | T | C | 0.7537 | 0.054147244 | 0.763 | 0.02912 | 0.89 | 0.004811 |
| rs6712068 | NRXN1 | 824642 | A | G | 0.7824 | 0.169636846 | 0.7752 | 0.006414 | 1.16 | 0.004445 |
| rs4971785 | NRXN1 | 1006007 | T | C | 0.4665 | 0.015101492 | 0.4403 | 0.05213 | 1.09 | 0.002889 |
| rs75775 | OXTR | 9432 | T | G | 0.1317 | 0.167462647 | 0.1247 | 0.004034 | 1.20 | 0.003116 |
| rs4839797 | GRIK2 | 0 | T | C | 0.09385 | 0.026019454 | 0.1 | 0.04654 | 0.86 | 0.003978 |
| rs2782908 | GRIK2 | 0 | A | G | 0.653 | 0.217719853 | 0.6495 | 0.006077 | 1.14 | 0.005692 |
| rs9390897 | GRIK2 | 758634 | A | G | 0.6799 | 0.758075774 | 0.6897 | 7.32E−05 | 0.83 | 0.008647 |
| rs1367645 | GRIK2 | 774787 | A | G | 0.94168 | 0.137809694 | 0.93105 | 0.01327 | 1.27 | 0.006152 |
| rs2205681 | GRIK2 | 1041317 | A | G | 0.91407 | 0.005932629 | 0.91248 | 0.1318 | 1.13 | 0.003976 |

TABLE 14-continued

Top association results (P < 0.01) for genotyped SNPs within or surrounding prominent
ASD loci previously implicated in linkage studies, cytogenetic studies and candidate gene
association studies. This list of potential ASD loci was compiled from a recent review
paper (16), including 8 "promising" genes and 18 "probable" genes.

| SNP | Closest gene | SNP-gene distance | A1 | A2 | A1_freq (AGRE) | P (AGRE) | A1_freq (ACC) | P (ACC) | Odds Ratio (ACC) | P (combined) |
|---|---|---|---|---|---|---|---|---|---|---|
| rs522447 | GRIK2 | 1094701 | A | G | 0.90591 | 0.005951226 | 0.90131 | 0.03858 | 1.18 | 0.001039 |
| rs513091 | GRIK2 | 1111819 | A | C | 0.1209 | 0.000834405 | 0.1227 | 0.03655 | 0.86 | 0.00023 |
| rs9404359 | GRIK2 | 1270169 | T | C | 0.07665 | 0.008650422 | 0.07922 | 0.1336 | 0.88 | 0.005231 |
| rs2399931 | GRIK2 | 1276273 | A | G | 0.92518 | 0.004135609 | 0.92239 | 0.1228 | 1.14 | 0.002864 |
| rs1155126 | GRIK2 | 1283682 | T | G | 0.8461 | 0.011702895 | 0.8359 | 0.08919 | 1.11 | 0.004154 |
| rs10264684 | CNTNAP2 | 0 | T | C | 0.1193 | 0.070182264 | 0.1145 | 0.04229 | 1.15 | 0.008385 |
| rs17170932 | CNTNAP2 | 0 | T | C | 0.7957 | 0.063198268 | 0.7759 | 0.05066 | 1.11 | 0.008989 |
| rs11971331 | EN2 | 63597 | A | G | 0.7906 | 0.032859445 | 0.8115 | 0.07177 | 0.90 | 0.007274 |
| rs2785079 | PTEN | 53854 | A | G | 0.1792 | 0.037645042 | 0.1944 | 0.01999 | 0.87 | 0.002503 |
| rs1855970 | PTEN | 94189 | T | G | 0.8555 | 0.003603458 | 0.851 | 0.02425 | 1.16 | 0.000437 |
| rs2108636 | CACNA1C | 2823 | T | G | 0.2367 | 0.003731608 | 0.2493 | 0.1541 | 0.93 | 0.00351 |
| rs7972947 | CACNA1C | 0 | A | C | 0.2038 | 0.019070685 | 0.2189 | 0.1204 | 0.92 | 0.008154 |
| rs4765898 | CACNA1C | 0 | A | G | 0.6734 | 0.039253592 | 0.6479 | 0.002878 | 1.15 | 0.000505 |
| rs2238034 | CACNA1C | 0 | T | C | 0.7613 | 0.056032717 | 0.7385 | 0.01058 | 1.14 | 0.002094 |
| rs2370419 | CACNA1C | 0 | A | G | 0.07443 | 0.133075953 | 0.06006 | 0.002356 | 1.30 | 0.00161 |
| rs4076021 | GABRB3 | 229543 | T | C | 0.90824 | 0.297545791 | 0.8989 | 0.007551 | 1.24 | 0.009643 |
| rs751994 | GABRB3 | 0 | T | C | 0.2965 | 0.023734212 | 0.2907 | 0.1227 | 1.08 | 0.009754 |
| rs1863455 | GABRB3 | 0 | T | C | 0.8874 | 0.009559274 | 0.8865 | 0.1976 | 0.92 | 0.008815 |
| rs11652097 | ITGB3 | 14491 | T | C | 0.3902 | 0.127124429 | 0.3989 | 0.007181 | 0.88 | 0.003525 |
| rs2056131 | ITGB3 | 0 | T | C | 0.3152 | 0.229719758 | 0.3022 | 0.008369 | 1.13 | 0.007625 |
| rs10514919 | ITGB3 | 0 | T | G | 0.2525 | 0.024986625 | 0.2477 | 0.08547 | 0.91 | 0.006991 |
| rs999323 | ITGB3 | 0 | A | G | 0.6944 | 0.085578978 | 0.6883 | 0.03919 | 1.11 | 0.009361 |
| (b) Significant SNPs within or surrounding ASD candidate loci on chromosome X are summarized below: | | | | | | | | | | |
| rs11798405 | NLGN4X | 877282 | A | G | 0.907172 | 0.006729 | 0.90051 | 1.10E−05 | 1.66 | 8.96E−07 |
| rs878252 | NLGN4X | 221323 | T | C | 0.480405 | 0.030916 | 0.4949 | 0.004555 | 0.85 | 0.000584 |
| rs11094994 | NLGN4X | 0 | T | C | 0.262923 | 0.021081 | 0.2533 | 0.002878 | 0.81 | 0.000274 |
| rs4826722 | NLGN4X | 100865 | A | G | 0.234249 | 0.012679 | 0.2364 | 0.1762 | 0.91 | 0.009322 |
| rs4826723 | NLGN4X | 115449 | T | C | 0.235548 | 0.01695 | 0.2372 | 0.1188 | 0.90 | 0.007383 |
| rs5951989 | FMR1 | 411643 | T | C | 0.780632 | 0.15267 | 0.7903 | 0.004058 | 1.24 | 0.002813 | family genes (NRXN1 to NRXN3, CNTNAP1 to CNTNAP5). Secondly, we analyzed the ACC cohort using a formal pathway-association method for case-control data sets[37]. We confirmed that the set of cadherin genes is associated with ASDs (permutation P=0.02), while the combined cadherin/neurexin genes show more significant association (permutation P=0.002). Therefore, our pathway analysis suggests that neuronal cell adhesion molecules may collectively play a role in the pathogenesis of ASDs.

In conclusion, in a combined sample of more than 10,000 subjects of European ancestry, we have identified common genetic variants in the intergenic region between CDH10 and CDH9 that are associated with susceptibility to ASDs. Besides the potential roles of CDH10 and CDH9, pathway-based association analysis lends support to other neuronal cell adhesion molecules in conferring susceptibility to ASDs. Apart from highlighting the genetic complexity of ASDs and the need for very large cohorts of patients for extended studies, our study represents a successful application of genome-wide association approaches to identify common susceptibility alleles, as part of a larger effort to interrogate the complex genetic architecture of ASDs.

References for Example II

1. Abrahams, B. S. & Geschwind, D. H. Advances in autism genetics: on the threshold of a new neurobiology. *Nat Rev Genet* 9, 341-55 (2008).
2. Autism and Developmental Disabilities Monitoring Network. http://www.cdc.gov/mmwr/pdf/ss/ss5601.pdf. (2007).
3. Bailey, A. et al. Autism as a strongly genetic disorder: evidence from a British twin study. *Psychol Med* 25, 63-77 (1995).
4. Lauritsen, M. B., Pedersen, C. B. & Mortensen, P. B. Effects of familial risk factors and place of birth on the risk of autism: a nationwide register-based study. *J Child Psychol Psychiatry* 46, 963-71 (2005).
5. Sykes, N. H. & Lamb, J. A. Autism: the quest for the genes. *Expert Rev Mol Med* 9, 1-15 (2007).
6. Gupta, A. R. & State, M. W. Recent advances in the genetics of autism. *Biol Psychiatry* 61, 429-37 (2007).
7. Freitag, C. M. The genetics of autistic disorders and its clinical relevance: a review of the literature. *Mol Psychiatry* 12, 2-22 (2007).
8. Veenstra-VanderWeele, J. & Cook, E. H., Jr. Molecular genetics of autism spectrum disorder. *Mol Psychiatry* 9, 819-32 (2004).
9. Vorstman, J. A. et al. Identification of novel autism candidate regions through analysis of reported cytogenetic abnormalities associated with autism. *Mol Psychiatry* 11, 1, 18-28 (2006).
10. Sebat, J. et al. Strong association of de novo copy number mutations with autism. *Science* 316, 445-9 (2007).
11. Weiss, L. A. et al. Association between Microdeletion and Microduplication at 16p11.2 and Autism. *N Engl J Med* (2008).
12. Kumar, R. A. et al. Recurrent 16p11.2 microdeletions in autism. *Hum Mol Genet* 17, 628-38 (2008).
13. Marshall, C. R. et al. Structural variation of chromosomes in autism spectrum disorder. *Am J Hum Genet* 82, 477-88 (2008).

14. WTCCC. Genome-wide association study of 14,000 cases of seven common diseases and 3,000 shared controls. *Nature* 447, 661-78 (2007).
15. Sklar, P. et al. Whole-genome association study of bipolar disorder. *Mol Psychiatry* 13, 558-69 (2008).
16. Alkelai, A. et al. The XVth World Congress of Psychiatric Genetics, Oct. 7-11, 2007: Rapporteur summaries of oral presentations. *Am J Med Genet B Neuropsychiatr Genet* 174B, 233-277 (2008).
17. O'Donovan, M. C. et al. Identification of loci associated with schizophrenia by genome-wide association and follow-up. *Nat Genet* (2008).
18. Ferreira, M. A. et al. Collaborative genome-wide association analysis supports a role for ANK3 and CACNA1C in bipolar disorder. *Nat Genet* (2008).
19. Martin, E. R., Monks, S. A., Warren, L. L. & Kaplan, N. L. A test for linkage and association in general pedigrees: the pedigree disequilibrium test. *Am J Hum Genet* 67, 146-54 (2000).
20. Chung, R. H., Morris, R. W., Zhang, L., Li, Y. J. & Martin, E. R. X-APL: an improved family-based test of association in the presence of linkage for the X chromosome. *Am J Hum Genet* 80, 59-68 (2007).
21. de Bakker, P. I. et al. Practical aspects of imputation-driven meta-analysis of genome-wide association studies. *Hum Mol Genet* 17, R122-8 (2008).
22. Wang, K. et al. PennCNV: an integrated hidden Markov model designed for high-resolution copy number variation detection in whole-genome SNP genotyping data. *Genome Res* 17, 1665-1674 (2007).
23. Siepel, A. et al. Evolutionarily conserved elements in vertebrate, insect, worm, and yeast genomes. *Genome Res* 15, 1034-50 (2005).
24. Ovcharenko, I. et al. Evolution and functional classification of vertebrate gene deserts. *Genome Res* 15, 137-45 (2005).
25. Kools, P., Vanhalst, K., Van den Eynde, E. & van Roy, F. The human cadherin-10 gene: complete coding sequence, predominant expression in the brain, and mapping on chromosome 5p13-14. *FEBS Lett* 452, 328-34 (1999).
26. Visel, A., Thaller, C. & Eichele, G. GenePaint.org: an atlas of gene expression patterns in the mouse embryo. *Nucleic Acids Res* 32, D552-6 (2004).
27. Heinzen, E. L. et al. Tissue-Specific Genetic Control of Splicing: Implications for the Study of Complex Traits. *PLoS Biol* 6, e1000001 (2008).
28. Witte, J. S. Multiple prostate cancer risk variants on 8q24. *Nat Genet* 39, 579-80 (2007).
29. Ghoussaini, M. et al. Multiple loci with different cancer specificities within the 8q24 gene desert. *J Natl Cancer Inst* 100, 962-6 (2008).
30. Kim, H. G. et al. Disruption of neurexin 1 associated with autism spectrum disorder. *Am J Hum Genet* 82, 199-207 (2008).
31. Szatmari, P. et al. Mapping autism risk loci using genetic linkage and chromosomal rearrangements. *Nat Genet* 39, 319-28 (2007).
32. Arking, D. E. et al. A common genetic variant in the neurexin superfamily member CNTNAP2 increases familial risk of autism. *Am J Hum Genet* 82, 160-4 (2008).
33. Alarcon, M. et al. Linkage, association, and gene-expression analyses identify CNTNAP2 as an autism-susceptibility gene. *Am J Hum Genet* 82, 150-9 (2008).
34. Bakkaloglu, B. et al. Molecular cytogenetic analysis and resequencing of contactin associated protein-like 2 in autism spectrum disorders. *Am J Hum Genet* 82, 165-73 (2008).
35. Morrow, E. M. et al. Identifying autism loci and genes by tracing recent shared ancestry. *Science* 321, 218-23 (2008).
36. Redies, C. Cadherins in the central nervous system. *Prog Neurobiol* 61, 611-48 (2000).
37. Wang, K., Li, M. & Bucan, M. Pathway-Based Approaches for Analysis of Genomewide Association Studies. *Am J Hum Genet* 81 (2007).

Example III

Screening Assays for Identifying Efficacious Therapeutics for the Treatment of Autism and ASD The information herein above can be applied clinically to patients for diagnosing an increased susceptibility for developing autism or autism spectrum disorder and therapeutic intervention. A preferred embodiment of the invention comprises clinical application of the information described herein to a patient. Diagnostic compositions, including microarrays, and methods can be designed to identify the genetic alterations described herein in nucleic acids from a patient to assess susceptibility for developing autism or ASD. This can occur after a patient arrives in the clinic; the patient has blood drawn, and using the diagnostic methods described herein, a clinician can detect a CNV as described in Example I, or a SNP in the CDH10 and CDH9 regions of chromosome 5 as described in Example II. The information obtained from the patient sample, which can optionally be amplified prior to assessment, will be used to diagnose a patient with an increased or decreased susceptibility for developing autism or ASD. Kits for performing the diagnostic method of the invention are also provided herein. Such kits comprise a microarray comprising at least one of the SNPs provided herein in and the necessary reagents for assessing the patient samples as described above.

The identity of autism/ASD involved genes and the patient results will indicate which variants are present, and will identify those that possess an altered risk for developing ASD. The information provided herein allows for therapeutic intervention at earlier times in disease progression than previously possible. Also as described herein above, CHD10 and CHD9 provide a novel targets for the development of new therapeutic agents efficacious for the treatment of this neurological disease.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A solid support having affixed thereon a collection of isolated SNP-containing nucleic acids, wherein the collection includes each allele of the SNPs, and each SNP tags a copy number variation (CNV) duplication on a specified chromosome, said duplication being associated with an altered risk for autism, said SNPs consisting of
   i) rs4346352 on chromosome 2 tagging a duplication between nucleotides 13119667-13165898,
   ii) rs7497239 on chromosome 15 tagging a duplication between nucleotides 22393833-22532309,
   iii) rs617372 on chromosome 12 tagging a duplication between nucleotides 31300846-31302088,
   iv) rs9342717 on chromosome 6 tagging a duplication between nucleotides 69291821-69294028,
   v) rs17015816 on chromosome 3 tagging a duplication between nucleotides 2548148-2548531,
   vi) rs9860992 on chromosome 3 tagging a duplication between nucleotides 174754378-174771975,
   vii) rs7681914 on chromosome 4 tagging a duplication between nucleotides 144847402-144854579,
   viii) rs12408178 on chromosome 1 tagging a duplication between nucleotides 145658465-145807358,
   ix) rs1107194 on chromosome 2 tagging a duplication between nucleotides 237486328-237497105,
   x) rs9346649 on chromosome 6 tagging a duplication between nucleotides 168091860-168339100,
   xi) rs1230300 on chromosome 19 tagging a duplication between nucleotides 22431189-22431397,
   xii) rs674478 on chromosome 22 tagging a duplication between nucleotides 19351264-19358946,
   xiii) rs13225132 on chromosome 7 tagging a duplication between nucleotides 32667087-32770713,
   xiv) rs6025553 on chromosome 20 tagging a duplication between nucleotides 55426961-55430874,
   xv) rs10798450 on chromosome 1 tagging a duplication between nucleotides 174500555-174543675,
   xvi) rs10435634 on chromosome 8 tagging a duplication between nucleotides 55021047-55070134,
   xvii) rs2070180 on chromosome 3-tagging a duplication between nucleotides 122826190-122870474, and
   and optionally the collection includes each allele of rs4307059, rs7704909, rs12518194, rs4327572, rs1896731 and rs10038113 each of said optional SNPS being on chromosome 5, wherein each of said SNP-containing nucleic acids are suitable for use as probes or primers and are between 15 and 25 nucleotides in length.

2. A kit comprising the solid support of claim 1, and reagents for detecting hybridization of complementary nucleic acids thereto.

3. The solid support of claim 1, which is a solid matrix selected from the group consisting of beads, microparticles, a microarray, the surface of a microtitration well or a test tube, a dipstick and a filter.

* * * * *

SEQUENCE LISTING

<160> NUMBER OF SEQ ID NOS: 23

<210> SEQ ID NO 1

```
<211> LENGTH: 121
<212> TYPE: DNA
<213> ORGANISM: Artificial Sequence
<220> FEATURE:
<223> OTHER INFORMATION: rs4346352

<400> SEQUENCE: 1
ctcagtcact taggcaagag cttgattttg agcccacgtt tgcagtagac atagttcttc      60
ygatcctagc gtacttctgg ctaacttctc cttcttggta gccccatgtt gctggtaacc     120
c                                                                     121

<210> SEQ ID NO 2
<211> LENGTH: 121
<212> TYPE: DNA
<213> ORGANISM: Artificial Sequence
<220> FEATURE:
<223> OTHER INFORMATION: rs7497239

<400> SEQUENCE: 2
aatctacaca tgttgataga aggcatcttc tagttagata ctgaggggaa aacaagagct      60
rtaaaagtta gtcctgactt taagaagtgt acaacttagt tggggaaagg gcattcaatg     120
t                                                                     121

<210> SEQ ID NO 3
<211> LENGTH: 121
<212> TYPE: DNA
<213> ORGANISM: Artificial Sequence
<220> FEATURE:
<223> OTHER INFORMATION: rs617372

<400> SEQUENCE: 3
tatcaccaaa tagcaagcca atttctacaa tgctatttat gcaataaata gaacaatttc      60
mttctttcct gttgattggt aattattata tgttgagttg ttttaaaatc ttgtgacttt     120
c                                                                     121

<210> SEQ ID NO 4
<211> LENGTH: 121
<212> TYPE: DNA
<213> ORGANISM: Artificial Sequence
<220> FEATURE:
<223> OTHER INFORMATION: rs9342717

<400> SEQUENCE: 4
aaatgcctat ttcataaagt cggaaagagc ccaaatagac aatccagaat cacacatcat      60
rgagctagag aaataacaac aaatcaaacc gaaacccatc aaaagaaaag aaataaccaa     120
g                                                                     121

<210> SEQ ID NO 5
<211> LENGTH: 121
<212> TYPE: DNA
<213> ORGANISM: Artificial Sequence
<220> FEATURE:
<223> OTHER INFORMATION: rs17015816

<400> SEQUENCE: 5
gaagtaaaga ttccatttga tgagtggaat tatctccccc atattaatgg tgatgaatgc      60
ycttgagagg ctaatgcatg caatttaaca aattcaaact cgagtcaaaa tctgtcttaa     120
t                                                                     121
```

```
<210> SEQ ID NO 6
<211> LENGTH: 121
<212> TYPE: DNA
<213> ORGANISM: Artificial Sequence
<220> FEATURE:
<223> OTHER INFORMATION: rs9860992

<400> SEQUENCE: 6
atgaacagga agaaaatcac acttagggat acaatattca aagtgatgaa aaccaatggt      60
rtatagaaca tcttaaaaag caagcagtga aaataatat tacaattagg aaataataa      120 t                                                                    121

<210> SEQ ID NO 7
<211> LENGTH: 121
<212> TYPE: DNA
<213> ORGANISM: Artificial Sequence
<220> FEATURE:
<223> OTHER INFORMATION: rs7681914

<400> SEQUENCE: 7
ctcttcacat tgtctttcct ctatctgtgt ctgtgtgtct aaatttcacc ttttcctaag      60
raccccagta atactggatt agggcccact ttactgacct catttgaact tgataatctc     120
t                                                                    121

<210> SEQ ID NO 8
<211> LENGTH: 121
<212> TYPE: DNA
<213> ORGANISM: Artificial Sequence
<220> FEATURE:
<223> OTHER INFORMATION: rs12408178

<400> SEQUENCE: 8
aagcaccggt cacaagcatt ccaagattct gcaaagatgt ttccttaatg ggctatattt      60
ktcatgggtg aatgagctta ggatcagcaa gagggaaaag agcaaggggc tgaatttcca     120
g                                                                    121

<210> SEQ ID NO 9
<211> LENGTH: 121
<212> TYPE: DNA
<213> ORGANISM: Artificial Sequence
<220> FEATURE:
<223> OTHER INFORMATION: rs1107194

<400> SEQUENCE: 9
ctctctttca aggagcccctt atagcttcag tcatcatggg aggggctttg aagttaaaaa      60
kgttcaaatg ccagttttgc ctcttcctag ctgtgaaaca gcagctaatt cactgaacct     120
c                                                                    121

<210> SEQ ID NO 10
<211> LENGTH: 121
<212> TYPE: DNA
<213> ORGANISM: Artificial Sequence
<220> FEATURE:
<223> OTHER INFORMATION: rs9346649

<400> SEQUENCE: 10
agcagcagtg aagctgctga tggtcgatta tctgtgcaca gtgacggtaa acagtgtgcg      60
ygataaacac agctgcctgg aggcggccat tcctgcctcg gtcctcctcc acctgtgtcc     120
t                                                                    121
```

<210> SEQ ID NO 11
<211> LENGTH: 121
<212> TYPE: DNA
<213> ORGANISM: Artificial Sequence
<220> FEATURE:
<223> OTHER INFORMATION: rs1230300

<400> SEQUENCE: 11

```
agattcattg cttgttttg ctttggcaaa agtttatatt ttttgttatt agccttctaa      60
rgtagacaca gatttgttta gataaatgtc attttaagtg cacacaaaag tttggcacca    120
a                                                                    121
```

<210> SEQ ID NO 12
<211> LENGTH: 121
<212> TYPE: DNA
<213> ORGANISM: Artificial Sequence
<220> FEATURE:
<223> OTHER INFORMATION: rs674478

<400> SEQUENCE: 12

```
gcagtatttg ggaacccatt atttcttgat tcatgctctt attttcatat aagagaagcg     60
ytgataccc aaaatcaact taaattttaa ttaaccaaat ataaaatttt taaagacaaa    120
a                                                                    121
```

<210> SEQ ID NO 13
<211> LENGTH: 121
<212> TYPE: DNA
<213> ORGANISM: Artificial Sequence
<220> FEATURE:
<223> OTHER INFORMATION: rs13225132

<400> SEQUENCE: 13

```
acaagcaacg gtttgtgggt gcctagtagc aaataatagc aaggtccgag tagaaagcag     60
ytggccaaag atcttgccat tgaaccaggg gagagagatg gggagtatat tggtttgaag    120
g                                                                    121
```

<210> SEQ ID NO 14
<211> LENGTH: 121
<212> TYPE: DNA
<213> ORGANISM: Artificial Sequence
<220> FEATURE:
<223> OTHER INFORMATION: rs6025553

<400> SEQUENCE: 14

```
gtccccaaag tctccacttg gcaggaatac tgggttggag gtgaccaggg gcaggcgcat     60
yccgaagcag ggagtgagcc acccggcggt gcccccaggc tacactagaa gccttgactt    120
c                                                                    121
```

<210> SEQ ID NO 15
<211> LENGTH: 121
<212> TYPE: DNA
<213> ORGANISM: Artificial Sequence
<220> FEATURE:
<223> OTHER INFORMATION: rs10798450

<400> SEQUENCE: 15

```
tattacatag gtctgactga tttattcttc ctaaaatccc actgactact ctctggcact     60
ygtgatcatt tagcatttta taaatgaaat gattaatgag tttggtcttt tcaggtatca    120
a                                                                    121
```

<210> SEQ ID NO 16
<211> LENGTH: 121
<212> TYPE: DNA
<213> ORGANISM: Artificial Sequence
<220> FEATURE:
<223> OTHER INFORMATION: rs1043564

<400> SEQUENCE: 16
ttttgagcat tgacatgaca ctcaaaggaa atgctcattg gaataatttg aagttttgga      60
yttgggatgt tcaactggta agtataatgc aaatattccg aaatctgaaa aaatctgaaa     120
t                                                                    121

<210> SEQ ID NO 17
<211> LENGTH: 121
<212> TYPE: DNA
<213> ORGANISM: Artificial Sequence
<220> FEATURE:
<223> OTHER INFORMATION: rs2070180

<400> SEQUENCE: 17
cccccagctc tgcccctag gactctggaa ggcctccagg tggaggaaga gccagtgtac       60
raagcagagc ctgagcctga gcccgagcct gagcccgagc ctgagaatga ctatgaggac     120
g                                                                    121

<210> SEQ ID NO 18
<211> LENGTH: 121
<212> TYPE: DNA
<213> ORGANISM: Artificial Sequence
<220> FEATURE:
<223> OTHER INFORMATION: rs4307059

<400> SEQUENCE: 18 tgttttctc caatataact cagttctgta cacatagctt tcactgatgt gtccgaattg       60
yttcatgtaa ccaggatatt ttccatgctt tctgtccgta gtaagagcca tgtattcccc     120
t                                                                    121

<210> SEQ ID NO 19
<211> LENGTH: 121
<212> TYPE: DNA
<213> ORGANISM: Artificial Sequence
<220> FEATURE:
<223> OTHER INFORMATION: rs7704909

<400> SEQUENCE: 19
tgtaaaaagc tcactctttg gtactggtgg catgaaatgt ccttctggtt gattgattat      60
rtttacatat agatagataa atatatataa tagataacat gtaatagacg aaaacttatg     120
g                                                                    121

<210> SEQ ID NO 20
<211> LENGTH: 121
<212> TYPE: DNA
<213> ORGANISM: Artificial Sequence
<220> FEATURE:
<223> OTHER INFORMATION: rs12518194

<400> SEQUENCE: 20
gcccaattta ttttccttc cattatcttc tatgtggcat ataaacagag gatctggggc       60
rtacaacttg atttcaactt tttacactgg ttaatgccct tggcttattg tatctggtgt     120

```
<210> SEQ ID NO 21
<211> LENGTH: 121
<212> TYPE: DNA
<213> ORGANISM: Artificial Sequence
<220> FEATURE:
<223> OTHER INFORMATION: rs4327572

<400> SEQUENCE: 21
ttagtatata gtagcatata gtagcatgct tatcctgtct ttttcatatt ttgctgtttt        60
rtttgcttta taagtattta taaaataaat aattttatca aattacttat tcagcaactt       120
c                                                                      121

<210> SEQ ID NO 22
<211> LENGTH: 121
<212> TYPE: DNA
<213> ORGANISM: Artificial Sequence
<220> FEATURE:
<223> OTHER INFORMATION: rs1896731

<400> SEQUENCE: 22
ttctgacatt actaatgctt ctcttggtca gttaagtatt ttaagttcat cctcctcagt        60
rgtaatgttg ggtcaaattt ttattttgaa ccaagaactt gtaaaaagct cactctttgg       120
t                                                                      121

<210> SEQ ID NO 23
<211> LENGTH: 121
<212> TYPE: DNA
<213> ORGANISM: Artificial Sequence
<220> FEATURE:
<223> OTHER INFORMATION: rs10038113

<400> SEQUENCE: 23
taggcaaaat tagaggcaga tgttgaaggg aaaggcagca atctaggttt ggccatgtag        60
yggaagacaa ggtcatgggg catcaactgt gggacgtaaa ccacgggcct ctatgaaagc       120
a                                                                      121
```